(12) United States Patent
Lee et al.

(10) Patent No.: US 7,902,154 B2
(45) Date of Patent: Mar. 8, 2011

(54) PHARMACEUTICAL COMPOSITION FOR ALLEVIATION AND TREATMENT OF ISCHEMIC CONDITIONS AND METHOD FOR DELIVERING THE SAME

(75) Inventors: Sang-Kyou Lee, Seoul (KR); Seung-Kyou Lee, Kyeunnggi-Do (KR); Yang-Soo Jang, Seoul (KR); Ki-Chul Hwang, Seoul (KR)

(73) Assignee: ForHumanTech. Co., Ltd., Suwon (KR)

( * ) Notice: Subject to any disclaimer, the term of this patent is extended or adjusted under 35 U.S.C. 154(b) by 493 days.

(21) Appl. No.: 11/878,431

(22) Filed: Jul. 24, 2007

(65) Prior Publication Data

US 2009/0087422 A1  Apr. 2, 2009

Related U.S. Application Data

(60) Provisional application No. 60/832,584, filed on Jul. 24, 2006.

(51) Int. Cl.
*A61K 38/00* (2006.01)
*A61K 38/16* (2006.01)

(52) U.S. Cl. .................. 514/15.1; 514/1.1; 514/13.5

(58) Field of Classification Search .................. None
See application file for complete search history.

(56) References Cited

U.S. PATENT DOCUMENTS

| | | | |
|---|---|---|---|
| 6,166,191 | A | 12/2000 | Randazzo |
| 2003/0104622 | A1 | 6/2003 | Robbins et al. |
| 2003/0229202 | A1 | 12/2003 | Guo et al. |
| 2005/0090646 | A1 | 4/2005 | Sullivan |
| 2005/0158373 | A1 | 7/2005 | Szeto et al. |
| 2006/0148060 | A1 | 7/2006 | Lee et al. |
| 2007/0105775 | A1 | 5/2007 | Lee et al. |
| 2008/0132450 | A1 | 6/2008 | Lee et al. |

FOREIGN PATENT DOCUMENTS

| | | |
|---|---|---|
| WO | WO 98/07858 A1 | 2/1998 |
| WO | WO 98/07860 A1 | 2/1998 |
| WO | WO 03/059940 A1 | 7/2003 |
| WO | WO 03/059941 A1 | 7/2003 |
| WO | WO 2004/044008 A1 | 5/2004 |
| WO | WO 2004/078933 A2 | 9/2004 |

OTHER PUBLICATIONS

Definition of hypoxia from http://dictionary.reference.com/browse/hypoxia, pp. 1-2, Accessed Aug. 13, 2009.*
Alzheimer's disease from http://www.alz.org/alzheimers_disease_what_is_alzheimers.asp, pp. 1-4. Accessed Aug. 13, 2009.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendesen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Frostbite from Merk manual, pp. 1-3. Accessed Feb. 18, 2010.*
Hypothermia from Merck manual, pp. 1-4. Accessed Feb. 16, 2010.*
Shock from Merck manual, pp. 1-7. Accessed Feb. 18, 2010.*
Alkema, M.J., et al., "Identification of Bmi1-interacting proteins as constituents of a multimeric mammalian Polycomb complex," *Genes & Dev.* 11:226-240, Cold Spring Harbor Laboratory Press (1997).
Asemu, G., et al., "Identification of the changes in phospholipase C isozymes in ischemic-reperfused rat heart," *Arch. Biochem. Biophys.* 411:174-182, Elsevier Science (Mar. 2003).
Choi, H.S., et al., "Transduced Tat-α-Synuclein Protects against Oxidative Stress In vitro and In vivo," *J. Biochem. Mol. Biol.* 39:253-262, Korean Society for Biochemistry and Molecular Biology (May 2006).
Dent, M.R., et al., "Phospholipase C gene expression, protein content, and activities in cardiac hypertrophy and heart failure due to volume overload," *Am. J. Physiol. Heart Circ. Physiol.* 287:H719-H727, The American Physiological Society (Apr. 2004).
Dietz, G.P.H., et al., "Inhibition of Neuronal Apoptosis in Vitro and in Vivo Using TAT-Mediated Protein Transduction," *Mol. Cell. Neurosci.* 21:29-37, Elsevier Science (Sep. 2002).
Gunster, M.J., et al., "Identification and Characterization of Interactions between the Vertebrate Polycomb-Group Protein BMI1 and Human Homologs of Polyhomeotic," *Mol. Cell. Biol* 17:2326-2335, American Society for Microbiology (1997).
Krief, S., et al., "Identification and Characterization of cvHSP," *J. Biol. Chem.* 274:36592-36600, The American Society for Biochemistry and Molecular Biology, Inc. (1999).
Kühnel, F., et al., "Protein Transduction Domains Fused to Virus Receptors Improve Cellular Virus Uptake and Enhance Oncolysis by Tumor-Specific Replicating Vectors," *J. Virol.* 78:13743-13754, American Society for Microbiology (Dec. 2004).
Lai, Y., et al., "Selectively increasing inducible heat shock protein 70 via TAT-protein transduction protects neurons from nitrosative stress excitotoxicity," *J. Neurochem.* 94:360-366, International Society for Neurochemistry (Jul. 2005).

(Continued)

*Primary Examiner* — Julie Ha
(74) *Attorney, Agent, or Firm* — Sterne Kessler Goldstetin & Fox, P.L.L.C.

(57) ABSTRACT

The present invention relates to pharmaceutical compositions for treating diseases and conditions caused by ischemia. The pharmaceutical compositions contain a conjugate of a phospholipase (PL) polypeptide and a protein transduction domain (PTD). PLC-δ plays a major role in the regulation of cytosolic calcium levels. During myocardial ischemia, cytosolic calcium accumulation mediates pathogenic changes. According to the present invention, ischemic diseases or conditions leading to hypoxia in tissues, such as the heart and the brain, can be prevented or alleviated by administration of a PTD-PL conjugate.

26 Claims, 6 Drawing Sheets

OTHER PUBLICATIONS

Figure 1:
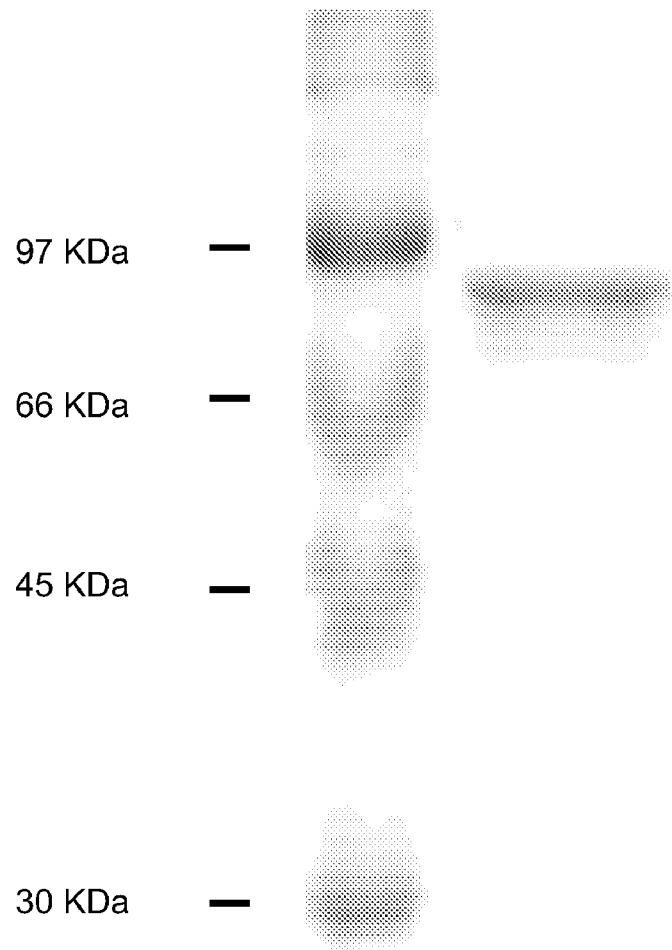

Lee, K-M., et al., "Molecular Basis of T Cell Inactivation by CTLA-4," *Science* 282:2263-2266, American Association for the Advancement of Science (1998).

Mangat, R., et al., "Inhibition of phospholipase C-$\gamma_1$ augments the decrease in cardiomyocyte viability by $H_2O_2$," *Am. J. Physiol. Heart Circ. Physiol.* 291:H854-H860, The American Physiological Society (Feb. 2006).

Noguchi, H., et al., "A new cell-permeable peptide allows successful allogenic islet transplantation in mice," *Nat. Med.* 10:305-309, Nature Publishing Company (Feb. 2004).

Ohta, H., et al., "Structure and Chromosomal Localization of the *RAE28/HPH1* Gene, A Human Homologue of the *Polyhomeotic* Gene," *DNA Seq.* 11:61-73, (OPA) Overseas Publishers Association N.V. (2000).

Wheeler, D.S., et al., "Intracellular delivery of HSP70 using HIV-1 Tat protein transduction domain," *Biochem. Biophys. Res. Commun.* 301:54-59, Elsevier Science (Jan. 2003).

Yagisawa, H., "Nucleocytoplasmic Shuttling of Phospholipase C-$\delta_1$: A Link to $Ca^{2+}$," *J. Cell. Biochem.* 97:233-243, Wiley-Liss, Inc. (Oct. 2005).

International Search Report for International Application No. PCT/IB2006/003971, Korean Intellectual Property Office, Republic of Korea, mailed on Sep. 19, 2007.

International Search Report for International Application No. PCT/IB2007/003404, Korean Patent Office, Republic of Korea, mailed on May 2, 2008.

International Search Report for International Application No. PCT/IB2007/004189, Korean Patent Office, Republic of Korea, mailed on Jun. 9, 2008.

Hwang, K.-C., et al., "Phospholipase C-$\delta$1 rescues intracellular $Ca^{2+}$ overload in ischemic heart and hypoxic neonatal cardiomyocotes," *Journal of Steroid Biochemistry and Molecular Biology*, 91:131-138, Elsevier Ltd., Holland (2004).

Nalefski, E.A. & Falke, J.J., "The C2 domain calcium-binding motif: Structural and functional diversity," *Protein Science*, 5:2375-2390, Cambridge University Press, United Kingdom (1996).

Rebecchi, M.J. & Pentyala, S.N., "Structure, Function, and Control of Phosphoinositide-Specific Phospholipase C," *Physiological Reviews*, 80:1291-1335, American Physiological Society, United States (2000).

Written Opinion of the International Searching Authority for International Application No. PCT/IB2007/003404, United States Patent and Trademark Office, Alexandria, Virginia, mailed on May 2, 2008.

* cited by examiner

I/R          I/R + PTD-PLCδ1

SEQUENCE LISTING

```
<160> NUMBER OF SEQ ID NOS: 37

<210> SEQ ID NO 1
<211> LENGTH: 11
<212> TYPE: PRT
<213> ORGANISM: Homo sapiens

<400> SEQUENCE: 1

Tyr Ala Arg Val Arg Arg Arg Gly Pro Arg Arg
1               5                   10

<210> SEQ ID NO 2
<211> LENGTH: 9
<212> TYPE: PRT
<213> ORGANISM: Homo sapiens

<400> SEQUENCE: 2

Ala Lys Ala Ala Arg Gln Ala Ala Arg
1               5
```

-continued

```
<210> SEQ ID NO 3
<211> LENGTH: 11
<212> TYPE: PRT
<213> ORGANISM: HIV viral

<400> SEQUENCE: 3

Tyr Gly Arg Lys Lys Arg Arg Gln Arg Arg Arg
1               5                   10

<210> SEQ ID NO 4
<211> LENGTH: 16
<212> TYPE: PRT
<213> ORGANISM: Drosophila

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 34
<212> TYPE: PRT
<213> ORGANISM: virus HSV-1

<400> SEQUENCE: 5

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 6
<211> LENGTH: 7
<212> TYPE: PRT
<213> ORGANISM: Homo sapiens

<400> SEQUENCE: 6

Arg Arg Arg Arg Arg Arg Arg
1               5

<210> SEQ ID NO 7
<211> LENGTH: 26
<212> TYPE: PRT
<213> ORGANISM: Homo sapiens

<400> SEQUENCE: 7

Ala Ala Val Ala Leu Leu Pro Ala Val Leu Leu Ala Leu Leu Ala Pro
1               5                   10                  15

Ala Ala Ala Asp Gln Asn Gln Leu Met Pro
            20                  25

<210> SEQ ID NO 8
<211> LENGTH: 21
<212> TYPE: PRT
<213> ORGANISM: Homo sapiens

<400> SEQUENCE: 8

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 9
<211> LENGTH: 21
<212> TYPE: PRT
```

<213> ORGANISM: Homo sapiens

<400> SEQUENCE: 9

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 10
<211> LENGTH: 2271
<212> TYPE: DNA
<213> ORGANISM: Homo sapiens

<400> SEQUENCE: 10

| | | | | | |
|---|---|---|---|---|---|
| atggactcgg | gccgggactt | cctgaccctg | cacggcctac | aggatgatga ggatctacag | 60 |
| gcgctgctga | agggcagcca | gctcctgaag | gtgaagtcca | gctcatggag gagagagcgc | 120 |
| ttctacaagt | tgcaggagga | ctgcaagacc | atctggcagg | agtcccgcaa ggtcatgcgg | 180 |
| accccggagt | cccagctgtt | ctccatcgag | gacattcagg | aggtgcgaat ggggcaccgc | 240 |
| acggagggtc | tggagaagtt | cgcccgtgat | gtgcccgagg | accgctgctt ctccattgtc | 300 |
| ttcaaggacc | agcgcaatac | actagacctc | atcgccccat | cgccagctga tgcccagcac | 360 |
| tgggtgctgg | gctgcacaa | gatcatccac | cactcaggct | ccatggacca gcgtcagaag | 420 |
| ctacagcact | ggattcactc | ctgcttgcga | aaagctgaca | aaaacaagga caacaagatg | 480 |
| agcttcaagg | agctgcagaa | cttcctgaag | gagctcaaca | tccaggtgga cgacagctat | 540 |
| gcccggaaga | tcttcaggga | gtgtgaccac | tcccagacag | actccctgga ggacgaggag | 600 |
| attgaggcct | tctacaagat | gctgacccag | cgggtggaga | tcgaccgcac cttcgccgag | 660 |
| gccgcgggct | caggggagac | tctgtcggtg | gatcagttag | tgacgttcct gcagcaccag | 720 |
| cagcgggagg | aggcggcagg | gcctgcgctg | gccctctccc | tcattgagcg ctacgagccc | 780 |
| agcgagactg | ccaaggcgca | gcggcagatg | accaaggacg | gcttcctcat gtacttactg | 840 |
| tcggctgacg | gcagcgcctt | cagcctggca | caccgccgtg | tctaccagga catgggccag | 900 |
| ccacttagcc | actacctggt | gtcctcttca | cacaacacct | acctgctgga ggaccagcta | 960 |
| gccgggccca | gcagcactga | agcctacatc | cgggcactgt | gcaaaggctg ccgatgcctg | 1020 |
| gagcttgact | gctgggacgg | gcccaaccag | gaaccaatca | tctaccacgg ctatactttc | 1080 |
| acttccaaga | tcctcttctg | cgatgtgctc | agggccatcc | gggactatgc cttcaaggcg | 1140 |
| tccccctacc | ctgtcatcct | atccctggag | aaccactgca | cactggagca gcagcgcgtg | 1200 |
| atggcgcggc | acctgcatgc | catcctgggc | cccatgctgt | tgaaccgacc actggatggg | 1260 |
| gtcaccaaca | gcctgccctc | ccctgagcaa | ctgaagggga | gatcctgct gaaggggaag | 1320 |
| aagctcgggg | ggctcctgcc | ccctggaggg | gagggtggcc | ctgaggccac tgtggtgtca | 1380 |
| gacgaagacg | aggctgctga | gatggaggat | gaggcagtga | ggagccgtgt gcagcacaag | 1440 |
| cccaaggagg | acaagctcag | gctagcacag | gagctctctg | acatggtcat ttactgcaag | 1500 |
| agtgtccact | tgggggcttc | ttccagtcct | ggcaccctg | acaggcctt ctacgagatg | 1560 |
| gcgtccttct | ctgagaaccg | tgcccttcga | ctgctccaag | aatcaggaaa cggctttgtc | 1620 |
| cgccacaacg | tggggcacct | gagcagaatc | tacccggctg | gatggagaac agactcctcc | 1680 |
| aactacagcc | ccgtggagat | gtggaatggg | ggctgccaga | tcgtggccct gaatttccag | 1740 |
| acacctgggc | cagagatgga | cgtgtaccag | ggccgcttcc | aggacaacgg ggcctgtgg | 1800 |
| tacgtgctga | agcccgcctt | cctgcgagac | cccaacggca | cctttaaccc ccgcgccctg | 1860 |

-continued

```
gctcaggggc cctggtgggc acggaagcgg ctcaacatca gggtcatttc ggggcagcag    1920
ctgccaaaag tcaacaagaa taagaattca attgtggacc ccaaagtgac agtggagatc    1980
catggcgtga gccgggacgt ggccagccgc cagactgctg tcatcaccaa caatggtttc    2040
aacccatggt gggacacgga gtttgcgttt gaggtagttg tgcctgacct tgccctcatc    2100
cgcttcttgg tggaagatta tgatgcctcc tccaagaatg acttcattgg ccagagtacc    2160
atccccttga acagcctcaa gcaaggatac cgccatgtcc acctcatgtc taagaacggg    2220
gaccagcatc catcagccac cctctttgtg aagatctccc tccaggacta g             2271
```

<210> SEQ ID NO 11
<211> LENGTH: 756
<212> TYPE: PRT
<213> ORGANISM: Homo sapiens

<400> SEQUENCE: 11

```
Met Asp Ser Gly Arg Asp Phe Leu Thr Leu His Gly Leu Gln Asp Asp
1               5                   10                  15

Glu Asp Leu Gln Ala Leu Leu Lys Gly Ser Gln Leu Leu Lys Val Lys
            20                  25                  30

Ser Ser Ser Trp Arg Arg Glu Arg Phe Tyr Lys Leu Gln Glu Asp Cys
        35                  40                  45

Lys Thr Ile Trp Gln Glu Ser Arg Lys Val Met Arg Thr Pro Glu Ser
    50                  55                  60

Gln Leu Phe Ser Ile Glu Asp Ile Gln Glu Val Arg Met Gly His Arg
65                  70                  75                  80

Thr Glu Gly Leu Glu Lys Phe Ala Arg Asp Val Pro Glu Asp Arg Cys
                85                  90                  95

Phe Ser Ile Val Phe Lys Asp Gln Arg Asn Thr Leu Asp Leu Ile Ala
            100                 105                 110

Pro Ser Pro Ala Asp Ala Gln His Trp Val Leu Gly Leu His Lys Ile
        115                 120                 125

Ile His Ser Gly Ser Met Asp Gln Arg Gln Lys Leu Gln His Trp
    130                 135                 140

Ile His Ser Cys Leu Arg Lys Ala Asp Lys Asn Lys Asp Asn Lys Met
145                 150                 155                 160

Ser Phe Lys Glu Leu Gln Asn Phe Leu Lys Glu Leu Asn Ile Gln Val
                165                 170                 175

Asp Asp Ser Tyr Ala Arg Lys Ile Phe Arg Glu Cys Asp His Ser Gln
            180                 185                 190

Thr Asp Ser Leu Glu Asp Glu Glu Ile Glu Ala Phe Tyr Lys Met Leu
        195                 200                 205

Thr Gln Arg Val Glu Ile Asp Arg Thr Phe Ala Glu Ala Ala Gly Ser
    210                 215                 220

Gly Glu Thr Leu Ser Val Asp Gln Leu Val Thr Phe Leu Gln His Gln
225                 230                 235                 240

Gln Arg Glu Glu Ala Ala Gly Pro Ala Leu Ala Leu Ser Leu Ile Glu
                245                 250                 255

Arg Tyr Glu Pro Ser Glu Thr Ala Lys Ala Gln Arg Gln Met Thr Lys
            260                 265                 270

Asp Gly Phe Leu Met Tyr Leu Leu Ser Ala Asp Gly Ser Ala Phe Ser
        275                 280                 285

Leu Ala His Arg Arg Val Tyr Gln Asp Met Gly Gln Pro Leu Ser His
    290                 295                 300

Tyr Leu Val Ser Ser Ser His Asn Thr Tyr Leu Leu Glu Asp Gln Leu
```

```
              305                 310                 315                 320
        Ala Gly Pro Ser Ser Thr Glu Ala Tyr Ile Arg Ala Leu Cys Lys Gly
                        325                 330                 335

Cys Arg Cys Leu Glu Leu Asp Cys Trp Asp Gly Pro Asn Gln Glu Pro
                        340                 345                 350

Ile Ile Tyr His Gly Tyr Thr Phe Thr Ser Lys Ile Leu Phe Cys Asp
                        355                 360                 365

Val Leu Arg Ala Ile Arg Asp Tyr Ala Phe Lys Ala Ser Pro Tyr Pro
        370                 375                 380

Val Ile Leu Ser Leu Glu Asn His Cys Thr Leu Glu Gln Gln Arg Val
        385                 390                 395                 400

Met Ala Arg His Leu His Ala Ile Leu Gly Pro Met Leu Leu Asn Arg
                        405                 410                 415

Pro Leu Asp Gly Val Thr Asn Ser Leu Pro Ser Pro Glu Gln Leu Lys
                        420                 425                 430

Gly Lys Ile Leu Leu Lys Gly Lys Lys Leu Gly Gly Leu Leu Pro Pro
                        435                 440                 445

Gly Gly Glu Gly Gly Pro Glu Ala Thr Val Val Ser Asp Glu Asp Glu
        450                 455                 460

Ala Ala Glu Met Glu Asp Glu Ala Val Arg Ser Arg Val Gln His Lys
        465                 470                 475                 480

Pro Lys Glu Asp Lys Leu Arg Leu Ala Gln Glu Leu Ser Asp Met Val
                        485                 490                 495

Ile Tyr Cys Lys Ser Val His Phe Gly Gly Phe Ser Ser Pro Gly Thr
                        500                 505                 510

Pro Gly Gln Ala Phe Tyr Glu Met Ala Ser Phe Ser Glu Asn Arg Ala
                        515                 520                 525

Leu Arg Leu Leu Gln Glu Ser Gly Asn Gly Phe Val Arg His Asn Val
        530                 535                 540

Gly His Leu Ser Arg Ile Tyr Pro Ala Gly Trp Arg Thr Asp Ser Ser
        545                 550                 555                 560

Asn Tyr Ser Pro Val Glu Met Trp Asn Gly Gly Cys Gln Ile Val Ala
                        565                 570                 575

Leu Asn Phe Gln Thr Pro Gly Pro Glu Met Asp Val Tyr Gln Gly Arg
                        580                 585                 590

Phe Gln Asp Asn Gly Ala Cys Gly Tyr Val Leu Lys Pro Ala Phe Leu
                        595                 600                 605

Arg Asp Pro Asn Gly Thr Phe Asn Pro Arg Ala Leu Ala Gln Gly Pro
        610                 615                 620

Trp Trp Ala Arg Lys Arg Leu Asn Ile Arg Val Ile Ser Gly Gln Gln
        625                 630                 635                 640

Leu Pro Lys Val Asn Lys Asn Lys Asn Ser Ile Val Asp Pro Lys Val
                        645                 650                 655

Thr Val Glu Ile His Gly Val Ser Arg Asp Val Ala Ser Arg Gln Thr
                        660                 665                 670

Ala Val Ile Thr Asn Asn Gly Phe Asn Pro Trp Trp Asp Thr Glu Phe
                        675                 680                 685

Ala Phe Glu Val Val Val Pro Asp Leu Ala Leu Ile Arg Phe Leu Val
                        690                 695                 700

Glu Asp Tyr Asp Ala Ser Ser Lys Asn Asp Phe Ile Gly Gln Ser Thr
        705                 710                 715                 720

Ile Pro Leu Asn Ser Leu Lys Gln Gly Tyr Arg His Val His Leu Met
                        725                 730                 735
```

-continued

Ser Lys Asn Gly Asp Gln His Pro Ser Ala Thr Leu Phe Val Lys Ile
            740                 745                 750

Ser Leu Gln Asp
        755

<210> SEQ ID NO 12
<211> LENGTH: 2370
<212> TYPE: DNA
<213> ORGANISM: Homo sapiens

<400> SEQUENCE: 12

| | | | | | |
|---|---|---|---|---|---|
| atgctgtgcg | gccgctggag | gcgttgccgc | cgcccgcccg | aggagccccc | ggtggccgcc   60 |
| caggtcgcag | cccaagtcgc | ggcgccggtc | gctctcccgt | ccccgccgac | tccctccgat  120 |
| ggcggcacca | agaggcccgg | gctgcgggcg | ctgaagaaga | tgggcctgac | ggaggacgag  180 |
| gacgtgcgcg | ccatgctgcg | gggctcccgg | ctccgcaaga | tccgctcgcg | cacgtggcac  240 |
| aaggagcggc | tgtaccggct | gcaggaggac | ggcctgagcg | tgtggttcca | gcggcgcatc  300 |
| ccgcgtgcgc | catcgcagca | catcttcttc | gtgcagcaca | tcgaggcggt | ccgcgagggc  360 |
| caccagtccg | agggcctgcg | cgcttcgggg | ggtgccttcg | cgccagcgcg | ctgcctcacc  420 |
| atcgccttca | agggccgccg | caagaacctg | gacctggcgg | cgcccacggc | tgaggaagcg  480 |
| cagcgctggg | tgcgcggtct | gaccaagctc | gcgcgcgcgcc | tggacgccat | gagccagcgc  540 |
| gagcggctag | accactggat | ccactcctat | ctgcaccggg | ctgactccaa | ccaggacagc  600 |
| aagatgagct | tcaaggagat | caagagcctg | ctgagaatgg | tcaacgtgga | catgaacgac  660 |
| atgtacgcct | acctcctctt | caaggagtgt | gaccactcca | caacgaccg | tctagagggg  720 |
| gctgagatcg | aggagttcct | gcggcggctg | ctgaagcggc | cggagctgga | ggagatcttc  780 |
| catcagtact | cgggcgagga | ccgcgtgctg | agtgcccctg | agctgctgga | gttcctggag  840 |
| gaccagggcg | aggagggcgc | cacactggcc | cgcgcccagc | agctcattca | gacctatgag  900 |
| ctcaacgaga | cagccaagca | gcatgagctg | atgacactgg | atggcttcat | gatgtacctg  960 |
| ttgtcgccgg | aggggctgc | cttggacaac | acccacacgt | gtgtgttcca | ggacatgaac 1020 |
| cagcccttg | cccactactt | catctcttcc | tcccacaaca | cctatctgac | tgactcccag 1080 |
| atcgggggc | ccagcagcac | cgaggcctat | gttagggcct | ttgcccaggg | atgccgctgc 1140 |
| gtggagctgg | actgctggga | ggggccagga | ggggagcccg | tcatctatca | tggccatacc 1200 |
| ctcacctcca | agattctctct | ccgggacgtg | gtccaagccg | tgcgcgacca | tgccttcacg 1260 |
| ctgtcccctt | accctgtcat | cctatccctg | gagaaccact | gcgggctgga | gcagcaggct 1320 |
| gccatggccc | gccacctctg | caccatcctg | ggggacatgc | tggtgacaca | ggcgctggac 1380 |
| tccccaaatc | ccgaggagct | gccatcccca | gagcagctga | agggccgggt | cctggtgaag 1440 |
| ggaaagaagc | tgcccgctgc | tcggagcgag | gatggccggg | ctctgtcgga | tcgggaggag 1500 |
| gaggaggagg | atgacgagga | ggaagaagag | gaggtggagg | ctgcagcgca | gaggcggctg 1560 |
| gccaagcaga | tctccccgga | gctgtcggcc | ctggctgtgt | actgccacgc | cacccgcctg 1620 |
| cggacccctgc | accctgcccc | caacgcccca | caacccctgcc | aggtcagctc | cctcagcgag 1680 |
| cgcaaagcca | agaaactcat | tcgggaggca | gggaacagct | ttgtcaggca | caatgcccgc 1740 |
| cagctgaccc | gcgtgtaccc | gctggggctg | cggatgaact | cagccaacta | cagtccccag 1800 |
| gagatgtgga | actcgggctg | tcagctggtg | gccttgaact | tccagacgcc | aggctacgag 1860 |
| atggaccctca | atgccgggcg | cttcctagtc | aatgggcagt | gtggctacgt | cctaaaacct 1920 |
| gcctgcctgc | ggcaacctga | ctcgaccttt | gaccccgagt | acccaggacc | tcccagaacc 1980 |

```
actctcagca tccaggtgct gactgcacag cagctgccca agctgaatgc cgagaagcca    2040
cactccattg tggaccccct ggtgcgcatt gagatccatg gggtgcccgc agactgtgcc    2100
cggcaggaga ctgactacgt gctcaacaat ggcttcaacc cccgctgggg gcagaccctg    2160
cagttccagc tgcgggctcc ggagctggca ctggtccggt ttgtggtgga agattatgac    2220
gccacctccc ccaatgactt tgtgggccag tttacactgc ctcttagcag cctaaagcaa    2280
gggtaccgcc acatacacct gctttccaag gacggggcct cactgtcacc agccacgctc    2340
ttcatccaaa tccgcatcca gcgctcctga                                     2370
```

<210> SEQ ID NO 13
<211> LENGTH: 789
<212> TYPE: PRT
<213> ORGANISM: Homo sapiens

<400> SEQUENCE: 13

```
Met Leu Cys Gly Arg Trp Arg Arg Cys Arg Arg Pro Glu Glu Pro
1               5                   10                  15

Pro Val Ala Ala Gln Val Ala Ala Gln Val Ala Pro Val Ala Leu
                20                  25                  30

Pro Ser Pro Thr Pro Ser Asp Gly Gly Thr Lys Arg Pro Gly Leu
            35                  40                  45

Arg Ala Leu Lys Lys Met Gly Leu Thr Glu Asp Glu Val Arg Ala
        50                  55                  60

Met Leu Arg Gly Ser Arg Leu Arg Lys Ile Arg Ser Arg Thr Trp His
65                  70                  75                  80

Lys Glu Arg Leu Tyr Arg Leu Gln Glu Asp Gly Leu Ser Val Trp Phe
                85                  90                  95

Gln Arg Arg Ile Pro Arg Ala Pro Ser Gln His Ile Phe Phe Val Gln
                100                 105                 110

His Ile Glu Ala Val Arg Glu Gly His Gln Ser Glu Gly Leu Arg Arg
            115                 120                 125

Phe Gly Gly Ala Phe Ala Pro Ala Arg Cys Leu Thr Ile Ala Phe Lys
    130                 135                 140

Gly Arg Arg Lys Asn Leu Asp Leu Ala Ala Pro Thr Ala Glu Glu Ala
145                 150                 155                 160

Gln Arg Trp Val Arg Gly Leu Thr Lys Leu Arg Ala Arg Leu Asp Ala
                165                 170                 175

Met Ser Gln Arg Glu Arg Leu Asp His Trp Ile His Ser Tyr Leu His
            180                 185                 190

Arg Ala Asp Ser Asn Gln Asp Ser Lys Met Ser Phe Lys Glu Ile Lys
        195                 200                 205

Ser Leu Leu Arg Met Val Asn Val Asp Met Asn Asp Met Tyr Ala Tyr
    210                 215                 220

Leu Leu Phe Lys Glu Cys Asp His Ser Asn Asn Asp Arg Leu Glu Gly
225                 230                 235                 240

Ala Glu Ile Glu Glu Phe Leu Arg Arg Leu Leu Lys Arg Pro Glu Leu
                245                 250                 255

Glu Glu Ile Phe His Gln Tyr Ser Gly Glu Asp Arg Val Leu Ser Ala
            260                 265                 270

Pro Glu Leu Leu Glu Phe Leu Glu Asp Gln Gly Glu Glu Gly Ala Thr
        275                 280                 285

Leu Ala Arg Ala Gln Gln Leu Ile Gln Thr Tyr Glu Leu Asn Glu Thr
    290                 295                 300

Ala Lys Gln His Glu Leu Met Thr Leu Asp Gly Phe Met Met Tyr Leu
```

```
              305                 310                 315                 320
        Leu Ser Pro Glu Gly Ala Ala Leu Asp Asn Thr His Thr Cys Val Phe
                        325                 330                 335

Gln Asp Met Asn Gln Pro Leu Ala His Tyr Phe Ile Ser Ser Ser His
                        340                 345                 350

Asn Thr Tyr Leu Thr Asp Ser Gln Ile Gly Gly Pro Ser Ser Thr Glu
                        355                 360                 365

Ala Tyr Val Arg Ala Phe Ala Gln Gly Cys Arg Cys Val Glu Leu Asp
                370                 375                 380

Cys Trp Glu Gly Pro Gly Glu Pro Val Ile Tyr His Gly His Thr
        385                 390                 395                 400

Leu Thr Ser Lys Ile Leu Phe Arg Asp Val Val Gln Ala Val Arg Asp
                        405                 410                 415

His Ala Phe Thr Leu Ser Pro Tyr Pro Val Ile Leu Ser Leu Glu Asn
                        420                 425                 430

His Cys Gly Leu Glu Gln Gln Ala Ala Met Ala Arg His Leu Cys Thr
                        435                 440                 445

Ile Leu Gly Asp Met Leu Val Thr Gln Ala Leu Asp Ser Pro Asn Pro
        450                 455                 460

Glu Glu Leu Pro Ser Pro Glu Gln Leu Lys Gly Arg Val Leu Val Lys
        465                 470                 475                 480

Gly Lys Lys Leu Pro Ala Ala Arg Ser Glu Asp Gly Arg Ala Leu Ser
                        485                 490                 495

Asp Arg Glu Glu Glu Glu Asp Glu Glu Glu Glu Glu Val
                        500                 505                 510

Glu Ala Ala Ala Gln Arg Arg Leu Ala Lys Gln Ile Ser Pro Glu Leu
                        515                 520                 525

Ser Ala Leu Ala Val Tyr Cys His Ala Thr Arg Leu Arg Thr Leu His
                        530                 535                 540

Pro Ala Pro Asn Ala Pro Gln Pro Cys Gln Val Ser Ser Leu Ser Glu
        545                 550                 555                 560

Arg Lys Ala Lys Lys Leu Ile Arg Glu Ala Gly Asn Ser Phe Val Arg
                        565                 570                 575

His Asn Ala Arg Gln Leu Thr Arg Val Tyr Pro Leu Gly Leu Arg Met
                        580                 585                 590

Asn Ser Ala Asn Tyr Ser Pro Gln Glu Met Trp Asn Ser Gly Cys Gln
                        595                 600                 605

Leu Val Ala Leu Asn Phe Gln Thr Pro Gly Tyr Glu Met Asp Leu Asn
                        610                 615                 620

Ala Gly Arg Phe Leu Val Asn Gly Gln Cys Gly Tyr Val Leu Lys Pro
        625                 630                 635                 640

Ala Cys Leu Arg Gln Pro Asp Ser Thr Phe Asp Pro Glu Tyr Pro Gly
                        645                 650                 655

Pro Pro Arg Thr Thr Leu Ser Ile Gln Val Leu Thr Ala Gln Gln Leu
                        660                 665                 670

Pro Lys Leu Asn Ala Glu Lys Pro His Ser Ile Val Asp Pro Leu Val
                        675                 680                 685

Arg Ile Glu Ile His Gly Val Pro Ala Asp Cys Ala Arg Gln Glu Thr
                        690                 695                 700

Asp Tyr Val Leu Asn Asn Gly Phe Asn Pro Arg Trp Gly Gln Thr Leu
        705                 710                 715                 720

Gln Phe Gln Leu Arg Ala Pro Glu Leu Ala Leu Val Arg Phe Val Val
                        725                 730                 735
```

```
Glu Asp Tyr Asp Ala Thr Ser Pro Asn Asp Phe Val Gly Gln Phe Thr
                740                 745                 750

Leu Pro Leu Ser Ser Leu Lys Gln Gly Tyr Arg His Ile His Leu Leu
            755                 760                 765

Ser Lys Asp Gly Ala Ser Leu Ser Pro Ala Thr Leu Phe Ile Gln Ile
    770                 775                 780

Arg Ile Gln Arg Ser
785

<210> SEQ ID NO 14
<211> LENGTH: 2289
<212> TYPE: DNA
<213> ORGANISM: Homo sapiens

<400> SEQUENCE: 14
```

| | | | | | |
|---|---|---|---|---|---|
| atggcgtccc | tgctgcaaga | ccagctgacc | actgatcagg | acttgctgct | gatgcaggaa | 60 |
| ggcatgccga | tgcgcaaggt | gaggtccaaa | agctggaaga | agctaagata | cttcagactt | 120 |
| cagaatgacg | gcatgacagt | ctggcatgca | cggcaggcca | ggggcagtgc | caagcccagc | 180 |
| ttctcaatct | ctgatgtgga | gacaatacgt | aatggccatg | attccgagtt | gctgcgtagc | 240 |
| ctggcagagg | agctcccct | ggagcagggc | ttcaccattg | tcttccatgg | ccgccgctcc | 300 |
| aacctggacc | tgatggccaa | cagtgttgag | gaggcccaga | tatggatgcg | agggctccag | 360 |
| ctgttggtgg | atcttgtcac | cagcatggac | catcaggagc | gcctggacca | atggctgagc | 420 |
| gattggtttc | aacgtggaga | caaaaatcag | gatggtaaga | tgagtttcca | agaagttcag | 480 |
| cggttattgc | acctaatgaa | tgtggaaatg | gaccaagaat | atgccttcag | tcttttttcag | 540 |
| gcagcagaca | cgtcccagtc | tggaaccctg | aaggagaag | aattcgtaca | gttctataag | 600 |
| gcattgacta | acgtgctga | ggtgcaggaa | ctgttgaaa | gttttttcagc | tgatgggcag | 660 |
| aagctgactc | tgctggaatt | tttggatttc | ctccaagagg | agcagaagga | gagagactgc | 720 |
| acctctgagc | ttgctctgga | actcattgac | cgctatgaac | cttcagacag | tggcaaactg | 780 |
| cggcatgtgc | tgagtatgga | tggcttcctc | agctacctct | gctctaagga | tggagacatc | 840 |
| ttcaacccag | cctgcctccc | catctatcag | gatatgactc | aacccctgaa | ccactacttc | 900 |
| atctgctctt | tcataacac | ctacctagtg | ggggaccagc | tttgcggcca | gagcagcgtc | 960 |
| gagggatata | tacgggccct | gaagcgggg | tgccgctgcg | tggaggtgga | tgtatgggat | 1020 |
| ggacctagcg | gggaacctgt | cgtttaccac | ggacacaccc | tgacctcccg | catcctgttc | 1080 |
| aaagatgtcg | tggccacagt | agcacagtat | gccttccaga | catcagacta | cccagtcatc | 1140 |
| ttgtccctgg | agaccactg | cagctgggag | cagcagcaga | ccatggcccg | tcatctgact | 1200 |
| gagatcctgg | gggagcagct | gctgagcacc | accttggatg | gggtgctgcc | cactcagctg | 1260 |
| ccctcgcctg | aggagcttcg | gaggaagatc | ctggtgaagg | ggaagaagtt | aacacttgag | 1320 |
| gaagacctgg | aatatgagga | agaggaagca | gaacctgagt | tggaagagtc | agaattggcg | 1380 |
| ctggagtccc | agtttgagac | tgagcctgag | ccccaggagc | agaaccttca | gaataaggac | 1440 |
| aaaaagaaga | aatccaagcc | catcttgtgt | ccagccctct | cttccctggt | tatctacttg | 1500 |
| aagtctgtct | cattccgcag | cttcacacat | tcaaaggagc | actaccactt | ctacgagata | 1560 |
| tcatctttct | ctgaaaccaa | ggccaagcgc | ctcatcaagg | aggctggcaa | tgagtttgtg | 1620 |
| cagcacaata | cttggcagtt | aagccgtgtg | tatcccagcg | gcctgaggac | agactcttcc | 1680 |
| aactacaacc | cccaggaact | ctggaatgca | ggctgccaga | tggtggccat | gaatatgcag | 1740 |
| actgcagggc | ttgaaatgga | catctgtgat | gggcatttcc | gccagaatgg | cggctgtggc | 1800 |

-continued

```
tatgtgctga agccagactt cctgcgtgat atccagagtt ctttccaccc tgagaagccc    1860
atcagccctt tcaaagccca gactctctta atccaggtga tcagcggtca gcaactcccc    1920
aaagtggaca agaccaaaga ggggtccatt gtggatccac tggtgaaagt gcagatcttt    1980
ggcgttcgtc tagacacagc acggcaggag accaactatg tggagaacaa tggttttaat    2040
ccatactggg ggcagacact atgtttccgg gtgctggtgc ctgaacttgc catgctgcgt    2100
tttgtggtaa tggattatga ctggaaatcc cgaaatgact ttattggtca gtacaccctg    2160
ccttggacct gcatgcaaca aggttaccgc cacattcacc tgctgtccaa agatggcatc    2220
agcctccgcc cagcttccat ctttgtgtat atctgcatcc aggaaggcct ggaggggat    2280 gagtcctga                                                            2289
```

<210> SEQ ID NO 15
<211> LENGTH: 762
<212> TYPE: PRT
<213> ORGANISM: Homo sapiens

<400> SEQUENCE: 15

```
Met Ala Ser Leu Leu Gln Asp Gln Leu Thr Thr Asp Gln Asp Leu Leu
1               5                   10                  15

Leu Met Gln Glu Gly Met Pro Met Arg Lys Val Arg Ser Lys Ser Trp
            20                  25                  30

Lys Lys Leu Arg Tyr Phe Arg Leu Gln Asn Asp Gly Met Thr Val Trp
        35                  40                  45

His Ala Arg Gln Ala Arg Gly Ser Ala Lys Pro Ser Phe Ser Ile Ser
    50                  55                  60

Asp Val Glu Thr Ile Arg Asn Gly His Asp Ser Glu Leu Leu Arg Ser
65                  70                  75                  80

Leu Ala Glu Glu Leu Pro Leu Glu Gln Gly Phe Thr Ile Val Phe His
                85                  90                  95

Gly Arg Arg Ser Asn Leu Asp Leu Met Ala Asn Ser Val Glu Glu Ala
            100                 105                 110

Gln Ile Trp Met Arg Gly Leu Gln Leu Leu Val Asp Leu Val Thr Ser
        115                 120                 125

Met Asp His Gln Glu Arg Leu Asp Gln Trp Leu Ser Asp Trp Phe Gln
    130                 135                 140

Arg Gly Asp Lys Asn Gln Asp Gly Lys Met Ser Phe Gln Glu Val Gln
145                 150                 155                 160

Arg Leu Leu His Leu Met Asn Val Glu Met Asp Gln Glu Tyr Ala Phe
                165                 170                 175

Ser Leu Phe Gln Ala Ala Asp Thr Ser Gln Ser Gly Thr Leu Glu Gly
            180                 185                 190

Glu Glu Phe Val Gln Phe Tyr Lys Ala Leu Thr Lys Arg Ala Glu Val
        195                 200                 205

Gln Glu Leu Phe Glu Ser Phe Ser Ala Asp Gly Gln Lys Leu Thr Leu
    210                 215                 220

Leu Glu Phe Leu Asp Phe Leu Gln Glu Glu Gln Lys Glu Arg Asp Cys
225                 230                 235                 240

Thr Ser Glu Leu Ala Leu Glu Leu Ile Asp Arg Tyr Glu Pro Ser Asp
                245                 250                 255

Ser Gly Lys Leu Arg His Val Leu Ser Met Asp Gly Phe Leu Ser Tyr
            260                 265                 270

Leu Cys Ser Lys Asp Gly Asp Ile Phe Asn Pro Ala Cys Leu Pro Ile
        275                 280                 285
```

```
Tyr Gln Asp Met Thr Gln Pro Leu Asn His Tyr Phe Ile Cys Ser Ser
    290                 295                 300

His Asn Thr Tyr Leu Val Gly Asp Gln Leu Cys Gly Gln Ser Ser Val
305                 310                 315                 320

Glu Gly Tyr Ile Arg Ala Leu Lys Arg Gly Cys Arg Cys Val Glu Val
                325                 330                 335

Asp Val Trp Asp Gly Pro Ser Gly Glu Pro Val Val Tyr His Gly His
            340                 345                 350

Thr Leu Thr Ser Arg Ile Leu Phe Lys Asp Val Val Ala Thr Val Ala
        355                 360                 365

Gln Tyr Ala Phe Gln Thr Ser Asp Tyr Pro Val Ile Leu Ser Leu Glu
370                 375                 380

Thr His Cys Ser Trp Glu Gln Gln Thr Met Ala Arg His Leu Thr
385                 390                 395                 400

Glu Ile Leu Gly Glu Gln Leu Leu Ser Thr Thr Leu Asp Gly Val Leu
                405                 410                 415

Pro Thr Gln Leu Pro Ser Pro Glu Glu Leu Arg Arg Lys Ile Leu Val
            420                 425                 430

Lys Gly Lys Lys Leu Thr Leu Glu Glu Asp Leu Glu Tyr Glu Glu Glu
        435                 440                 445

Glu Ala Glu Pro Glu Leu Glu Glu Ser Glu Leu Ala Leu Glu Ser Gln
450                 455                 460

Phe Glu Thr Glu Pro Glu Pro Gln Glu Gln Asn Leu Gln Asn Lys Asp
465                 470                 475                 480

Lys Lys Lys Lys Ser Lys Pro Ile Leu Cys Pro Ala Leu Ser Ser Leu
                485                 490                 495

Val Ile Tyr Leu Lys Ser Val Ser Phe Arg Ser Phe Thr His Ser Lys
            500                 505                 510

Glu His Tyr His Phe Tyr Glu Ile Ser Ser Phe Ser Glu Thr Lys Ala
        515                 520                 525

Lys Arg Leu Ile Lys Glu Ala Gly Asn Glu Phe Val Gln His Asn Thr
530                 535                 540

Trp Gln Leu Ser Arg Val Tyr Pro Ser Gly Leu Arg Thr Asp Ser Ser
545                 550                 555                 560

Asn Tyr Asn Pro Gln Glu Leu Trp Asn Ala Gly Cys Gln Met Val Ala
                565                 570                 575

Met Asn Met Gln Thr Ala Gly Leu Glu Met Asp Ile Cys Asp Gly His
            580                 585                 590

Phe Arg Gln Asn Gly Gly Cys Gly Tyr Val Leu Lys Pro Asp Phe Leu
        595                 600                 605

Arg Asp Ile Gln Ser Ser Phe His Pro Glu Lys Pro Ile Ser Pro Phe
610                 615                 620

Lys Ala Gln Thr Leu Leu Ile Gln Val Ile Ser Gly Gln Gln Leu Pro
625                 630                 635                 640

Lys Val Asp Lys Thr Lys Glu Gly Ser Ile Val Asp Pro Leu Val Lys
                645                 650                 655

Val Gln Ile Phe Gly Val Arg Leu Asp Thr Ala Arg Gln Glu Thr Asn
            660                 665                 670

Tyr Val Glu Asn Asn Gly Phe Asn Pro Tyr Trp Gly Gln Thr Leu Cys
        675                 680                 685

Phe Arg Val Leu Val Pro Glu Leu Ala Met Leu Arg Phe Val Val Met
690                 695                 700

Asp Tyr Asp Trp Lys Ser Arg Asn Asp Phe Ile Gly Gln Tyr Thr Leu
705                 710                 715                 720
```

```
Pro Trp Thr Cys Met Gln Gln Gly Tyr Arg His Ile His Leu Leu Ser
            725                 730                 735

Lys Asp Gly Ile Ser Leu Arg Pro Ala Ser Ile Phe Val Tyr Ile Cys
            740                 745                 750

Ile Gln Glu Gly Leu Glu Gly Asp Glu Ser
            755                 760

<210> SEQ ID NO 16
<211> LENGTH: 1216
<212> TYPE: PRT
<213> ORGANISM: Homo sapiens

<400> SEQUENCE: 16

Met Ala Gly Ala Gln Pro Gly Val His Ala Leu Gln Leu Lys Pro Val
1               5                   10                  15

Cys Val Ser Asp Ser Leu Lys Lys Gly Thr Lys Phe Val Lys Trp Asp
            20                  25                  30

Asp Asp Ser Thr Ile Val Thr Pro Ile Ile Leu Arg Thr Asp Pro Gln
            35                  40                  45

Gly Phe Phe Tyr Trp Thr Asp Gln Asn Lys Glu Thr Glu Leu Leu
    50                  55                  60

Asp Leu Ser Leu Val Lys Asp Ala Arg Cys Gly Arg His Ala Lys Ala
65              70                  75                  80

Pro Lys Asp Pro Lys Leu Arg Glu Leu Leu Asp Val Gly Asn Ile Gly
            85                  90                  95

Arg Leu Glu Gln Arg Met Ile Thr Val Val Tyr Gly Pro Asp Leu Val
            100                 105                 110

Asn Ile Ser His Leu Asn Leu Val Ala Phe Gln Glu Glu Val Ala Lys
            115                 120                 125

Glu Trp Thr Asn Glu Val Phe Ser Leu Ala Thr Asn Leu Leu Ala Gln
            130                 135                 140

Asn Met Ser Arg Asp Ala Phe Leu Glu Lys Ala Tyr Thr Lys Leu Lys
145             150                 155                 160

Leu Gln Val Thr Pro Glu Gly Arg Ile Pro Leu Lys Asn Ile Tyr Arg
            165                 170                 175

Leu Phe Ser Ala Asp Arg Lys Arg Val Glu Thr Ala Leu Glu Ala Cys
            180                 185                 190

Ser Leu Pro Ser Ser Arg Asn Asp Ser Ile Pro Gln Glu Asp Phe Thr
            195                 200                 205

Pro Glu Val Tyr Arg Val Phe Leu Asn Asn Leu Cys Pro Arg Pro Glu
            210                 215                 220

Ile Asp Asn Ile Phe Ser Glu Phe Gly Ala Lys Ser Lys Pro Tyr Leu
225             230                 235                 240

Thr Val Asp Gln Met Met Asp Phe Ile Asn Leu Lys Gln Arg Asp Pro
            245                 250                 255

Arg Leu Asn Glu Ile Leu Tyr Pro Pro Leu Lys Gln Glu Gln Val Gln
            260                 265                 270

Val Leu Ile Glu Lys Tyr Glu Pro Asn Asn Ser Leu Ala Arg Lys Gly
            275                 280                 285

Gln Ile Ser Val Asp Gly Phe Met Arg Tyr Leu Ser Gly Glu Glu Asn
            290                 295                 300

Gly Val Val Ser Pro Glu Lys Leu Asp Leu Asn Glu Asp Met Ser Gln
305             310                 315                 320

Pro Leu Ser His Tyr Phe Ile Asn Ser Ser His Asn Thr Tyr Leu Thr
            325                 330                 335
```

```
Ala Gly Gln Leu Ala Gly Asn Ser Ser Val Glu Met Tyr Arg Gln Val
            340                 345                 350

Leu Leu Ser Gly Cys Arg Cys Val Glu Leu Asp Cys Trp Lys Gly Arg
            355                 360                 365

Thr Ala Glu Glu Glu Pro Val Ile Thr His Gly Phe Thr Met Thr Thr
            370                 375                 380

Glu Ile Ser Phe Lys Glu Val Ile Glu Ala Ile Ala Glu Cys Ala Phe
385                 390                 395                 400

Lys Thr Ser Pro Phe Pro Ile Leu Leu Ser Phe Glu Asn His Val Asp
            405                 410                 415

Ser Pro Lys Gln Gln Ala Lys Met Ala Glu Tyr Cys Arg Leu Ile Phe
            420                 425                 430

Gly Asp Ala Leu Leu Met Glu Pro Leu Glu Lys Tyr Pro Leu Glu Ser
            435                 440                 445

Gly Val Pro Leu Pro Ser Pro Met Asp Leu Met Tyr Lys Ile Leu Val
            450                 455                 460

Lys Asn Lys Lys Lys Ser His Lys Ser Ser Glu Gly Ser Gly Lys Lys
465                 470                 475                 480

Lys Leu Ser Glu Gln Ala Ser Asn Thr Tyr Ser Asp Ser Ser Ser Met
            485                 490                 495

Phe Glu Pro Ser Ser Pro Gly Ala Gly Glu Ala Asp Thr Glu Ser Asp
            500                 505                 510

Asp Asp Asp Asp Asp Asp Cys Lys Lys Ser Ser Met Asp Glu Gly
            515                 520                 525

Thr Ala Gly Ser Glu Ala Met Ala Thr Glu Glu Met Ser Asn Leu Val
            530                 535                 540

Asn Tyr Ile Gln Pro Val Lys Phe Glu Ser Phe Glu Ile Ser Lys Lys
545                 550                 555                 560

Arg Asn Lys Ser Phe Glu Met Ser Ser Phe Val Glu Thr Lys Gly Leu
            565                 570                 575

Glu Gln Leu Thr Lys Ser Pro Val Glu Phe Val Glu Tyr Asn Lys Met
            580                 585                 590

Gln Leu Ser Arg Ile Tyr Pro Lys Gly Thr Arg Val Asp Ser Ser Asn
            595                 600                 605

Tyr Met Pro Gln Leu Phe Trp Asn Ala Gly Cys Gln Met Val Ala Leu
            610                 615                 620

Asn Phe Gln Thr Met Asp Leu Ala Met Gln Ile Asn Met Gly Met Tyr
625                 630                 635                 640

Glu Tyr Asn Gly Lys Ser Gly Tyr Arg Leu Lys Pro Glu Phe Met Arg
            645                 650                 655

Arg Pro Asp Lys His Phe Asp Pro Phe Thr Glu Gly Ile Val Asp Gly
            660                 665                 670

Ile Val Ala Asn Thr Leu Ser Val Lys Ile Ile Ser Gly Gln Phe Leu
            675                 680                 685

Ser Asp Lys Lys Val Gly Thr Tyr Val Glu Val Asp Met Phe Gly Leu
            690                 695                 700

Pro Val Asp Thr Arg Arg Lys Ala Phe Lys Thr Lys Thr Ser Gln Gly
705                 710                 715                 720

Asn Ala Val Asn Pro Val Trp Glu Glu Pro Ile Val Phe Lys Lys
            725                 730                 735

Val Val Leu Pro Thr Leu Ala Cys Leu Arg Ile Ala Val Tyr Glu Glu
            740                 745                 750

Gly Gly Lys Phe Ile Gly His Arg Ile Leu Pro Val Gln Ala Ile Arg
```

```
            755                 760                 765
Pro Gly Tyr His Tyr Ile Cys Leu Arg Asn Glu Arg Asn Gln Pro Leu
770                 775                 780
Thr Leu Pro Ala Val Phe Val Tyr Ile Glu Val Lys Asp Tyr Val Pro
785                 790                 795                 800
Asp Thr Tyr Ala Asp Val Ile Glu Ala Leu Ser Asn Pro Ile Arg Tyr
        805                 810                 815
Val Asn Leu Met Glu Gln Arg Ala Lys Gln Leu Ala Ala Leu Thr Leu
            820                 825                 830
Glu Asp Glu Glu Val Lys Lys Glu Ala Asp Pro Gly Glu Thr Pro
        835                 840                 845
Ser Glu Ala Pro Ser Glu Ala Arg Thr Thr Pro Ala Glu Asn Gly Val
850                 855                 860
Asn His Thr Thr Thr Leu Thr Pro Lys Pro Ser Gln Ala Leu His
865                 870                 875                 880
Ser Gln Pro Ala Pro Gly Ser Val Lys Ala Pro Ala Lys Thr Glu Asp
                885                 890                 895
Leu Ile Gln Ser Val Leu Thr Glu Val Glu Ala Gln Thr Ile Glu Glu
            900                 905                 910
Leu Lys Gln Gln Lys Ser Phe Val Lys Leu Gln Lys His Tyr Lys
        915                 920                 925
Glu Met Lys Asp Leu Val Lys Arg His His Lys Lys Thr Thr Asp Leu
930                 935                 940
Ile Lys Glu His Thr Thr Lys Tyr Asn Glu Ile Gln Asn Asp Tyr Leu
945                 950                 955                 960
Arg Arg Arg Ala Ala Leu Glu Lys Ser Ala Lys Lys Asp Ser Lys Lys
            965                 970                 975
Lys Ser Glu Pro Ser Ser Pro Asp His Gly Ser Ser Thr Ile Glu Gln
        980                 985                 990
Asp Leu Ala Ala Leu Asp Ala Glu Met Thr Gln Lys Leu Ile Asp Leu
            995                 1000                1005
Lys Asp Lys Gln Gln Gln Gln Leu Leu Asn Leu Arg Gln Glu Gln
    1010                1015                1020
Tyr Tyr Ser Glu Lys Tyr Gln Lys Arg Glu His Ile Lys Leu Leu
    1025                1030                1035
Ile Gln Lys Leu Thr Asp Val Ala Glu Glu Cys Gln Asn Asn Gln
    1040                1045                1050
Leu Lys Lys Leu Lys Glu Ile Cys Glu Lys Glu Lys Lys Glu Leu
    1055                1060                1065
Lys Lys Lys Met Asp Lys Lys Arg Gln Glu Lys Ile Thr Glu Ala
    1070                1075                1080
Lys Ser Lys Asp Lys Ser Gln Met Glu Glu Glu Lys Thr Glu Met
    1085                1090                1095
Ile Arg Ser Tyr Ile Gln Glu Val Val Gly Tyr Ile Lys Arg Leu
    1100                1105                1110
Glu Glu Ala Gln Ser Lys Arg Gln Glu Lys Leu Val Glu Lys His
    1115                1120                1125
Lys Glu Ile Arg Gln Gln Ile Leu Asp Glu Lys Pro Lys Leu Gln
    1130                1135                1140
Val Glu Leu Glu Gln Glu Tyr Gln Asp Lys Phe Lys Arg Leu Pro
    1145                1150                1155
Leu Glu Ile Leu Glu Phe Val Gln Glu Ala Met Lys Gly Lys Ile
    1160                1165                1170
```

```
Ser Glu Asp Ser Asn His Gly Ser Ala Pro Leu Ser Leu Ser Ser
    1175                1180                1185

Asp Pro Gly Lys Val Asn His Lys Thr Pro Ser Ser Glu Glu Leu
    1190                1195                1200

Gly Gly Asp Ile Pro Gly Lys Glu Phe Asp Thr Pro Leu
    1205                1210                1215

<210> SEQ ID NO 17
<211> LENGTH: 1181
<212> TYPE: PRT
<213> ORGANISM: Homo sapiens

<400> SEQUENCE: 17

Met Ser Leu Leu Asn Pro Val Leu Leu Pro Pro Lys Val Lys Ala Tyr
1               5                   10                  15

Leu Ser Gln Gly Glu Arg Phe Ile Lys Trp Asp Asp Glu Thr Thr Val
                20                  25                  30

Ala Ser Pro Val Ile Leu Arg Val Asp Pro Lys Gly Tyr Tyr Leu Tyr
            35                  40                  45

Trp Thr Tyr Gln Ser Lys Glu Met Glu Phe Leu Asp Ile Thr Ser Ile
50                  55                  60

Arg Asp Thr Arg Phe Gly Lys Phe Ala Lys Met Pro Lys Ser Gln Lys
65                  70                  75                  80

Leu Arg Asp Val Phe Asn Met Asp Phe Pro Asp Asn Ser Phe Leu Leu
                85                  90                  95

Lys Thr Leu Thr Val Val Ser Gly Pro Asp Met Val Asp Leu Thr Phe
            100                 105                 110

His Asn Phe Val Ser Tyr Lys Glu Asn Val Gly Lys Ala Trp Ala Glu
        115                 120                 125

Asp Val Leu Ala Leu Val Lys His Pro Leu Thr Ala Asn Ala Ser Arg
130                 135                 140

Ser Thr Phe Leu Asp Lys Ile Leu Val Lys Leu Lys Met Gln Leu Asn
145                 150                 155                 160

Ser Glu Gly Lys Ile Pro Val Lys Asn Phe Phe Gln Met Phe Pro Ala
                165                 170                 175

Asp Arg Lys Arg Val Glu Ala Ala Leu Ser Ala Cys His Leu Pro Lys
            180                 185                 190

Gly Lys Asn Asp Ala Ile Asn Pro Glu Asp Phe Pro Glu Pro Val Tyr
        195                 200                 205

Lys Ser Phe Leu Met Ser Leu Cys Pro Arg Pro Glu Ile Asp Glu Ile
210                 215                 220

Phe Thr Ser Tyr His Ala Lys Ala Lys Pro Tyr Met Thr Lys Glu His
225                 230                 235                 240

Leu Thr Lys Phe Ile Asn Gln Lys Gln Arg Asp Ser Arg Leu Asn Ser
                245                 250                 255

Leu Leu Phe Pro Pro Ala Arg Pro Asp Gln Val Gln Gly Leu Ile Asp
            260                 265                 270

Lys Tyr Glu Pro Ser Gly Ile Asn Ala Gln Arg Gly Gln Leu Ser Pro
        275                 280                 285

Glu Gly Met Val Trp Phe Leu Cys Gly Pro Glu Asn Ser Val Leu Ala
290                 295                 300

Gln Asp Lys Leu Leu Leu His His Asp Met Thr Gln Pro Leu Asn His
305                 310                 315                 320

Tyr Phe Ile Asn Ser Ser His Asn Thr Tyr Leu Thr Ala Gly Gln Phe
                325                 330                 335
```

-continued

```
Ser Gly Leu Ser Ser Ala Glu Met Tyr Arg Gln Val Leu Leu Ser Gly
            340                 345                 350

Cys Arg Cys Val Glu Leu Asp Cys Trp Lys Gly Lys Pro Asp Glu
        355                 360                 365

Glu Pro Ile Ile Thr His Gly Phe Thr Met Thr Thr Asp Ile Phe Phe
        370                 375                 380

Lys Glu Ala Ile Glu Ala Ile Ala Glu Ser Ala Phe Lys Thr Ser Pro
385                 390                 395                 400

Tyr Pro Ile Ile Leu Ser Phe Glu Asn His Val Asp Ser Pro Arg Gln
                405                 410                 415

Gln Ala Lys Met Ala Glu Tyr Cys Arg Thr Ile Phe Gly Asp Met Leu
            420                 425                 430

Leu Thr Glu Pro Leu Glu Lys Phe Pro Leu Lys Pro Gly Val Pro Leu
        435                 440                 445

Pro Ser Pro Glu Asp Leu Arg Gly Lys Ile Leu Ile Lys Asn Lys Lys
        450                 455                 460

Asn Gln Phe Ser Gly Pro Thr Ser Ser Ser Lys Asp Thr Gly Gly Glu
465                 470                 475                 480

Ala Glu Gly Ser Ser Pro Pro Ser Ala Pro Ala Val Trp Ala Gly Glu
                485                 490                 495

Glu Gly Thr Glu Leu Glu Glu Glu Val Glu Glu Glu Glu Glu
        500                 505                 510

Glu Ser Gly Asn Leu Asp Glu Glu Ile Lys Lys Met Gln Ser Asp
        515                 520                 525

Glu Gly Thr Ala Gly Leu Glu Val Thr Ala Tyr Glu Glu Met Ser Ser
        530                 535                 540

Leu Val Asn Tyr Ile Gln Pro Thr Lys Phe Val Ser Phe Glu Phe Ser
545                 550                 555                 560

Ala Gln Lys Asn Arg Ser Tyr Val Ile Ser Ser Phe Thr Glu Leu Lys
                565                 570                 575

Ala Tyr Asp Leu Leu Ser Lys Ala Ser Val Gln Phe Val Asp Tyr Asn
            580                 585                 590

Lys Arg Gln Met Ser Arg Ile Tyr Pro Lys Gly Thr Arg Met Asp Ser
        595                 600                 605

Ser Asn Tyr Met Pro Gln Met Phe Trp Asn Ala Gly Cys Gln Met Val
        610                 615                 620

Ala Leu Asn Phe Gln Thr Met Asp Leu Pro Met Gln Gln Asn Met Ala
625                 630                 635                 640

Val Phe Glu Phe Asn Gly Gln Ser Gly Tyr Leu Leu Lys His Glu Phe
                645                 650                 655

Met Arg Arg Pro Asp Lys Gln Phe Asn Pro Phe Ser Val Asp Arg Ile
            660                 665                 670

Asp Val Val Val Ala Thr Thr Leu Ser Ile Thr Val Ile Ser Gly Gln
        675                 680                 685

Phe Leu Ser Glu Arg Ser Val Arg Thr Tyr Val Glu Val Glu Leu Phe
        690                 695                 700

Gly Leu Pro Gly Asp Pro Lys Arg Arg Tyr Arg Thr Lys Leu Ser Pro
705                 710                 715                 720

Ser Thr Asn Ser Ile Asn Pro Val Trp Lys Glu Glu Pro Phe Val Phe
                725                 730                 735

Glu Lys Ile Leu Met Pro Glu Leu Ala Ser Leu Arg Val Ala Val Met
            740                 745                 750

Glu Glu Gly Asn Lys Phe Leu Gly His Arg Ile Ile Pro Ile Asn Ala
        755                 760                 765
```

-continued

```
Leu Asn Ser Gly Tyr His His Leu Cys Leu His Ser Glu Ser Asn Met
    770             775             780

Pro Leu Thr Met Pro Ala Leu Phe Ile Phe Leu Glu Met Lys Asp Tyr
785             790             795             800

Ile Pro Gly Ala Trp Ala Asp Leu Thr Val Ala Leu Ala Asn Pro Ile
            805             810             815

Lys Phe Phe Ser Ala His Asp Thr Lys Ser Val Lys Leu Lys Glu Ala
        820             825             830

Met Gly Gly Leu Pro Glu Lys Pro Phe Pro Leu Ala Ser Pro Val Ala
            835             840             845

Ser Gln Val Asn Gly Ala Leu Ala Pro Thr Ser Asn Gly Ser Pro Ala
    850             855             860

Ala Arg Ala Gly Ala Arg Glu Glu Ala Met Lys Glu Ala Ala Glu Pro
865             870             875             880

Arg Thr Ala Ser Leu Glu Glu Leu Arg Glu Leu Lys Gly Val Val Lys
                885             890             895

Leu Gln Arg Arg His Glu Lys Glu Leu Arg Glu Leu Glu Arg Arg Gly
            900             905             910

Ala Arg Arg Trp Glu Leu Leu Gln Arg Gly Ala Ala Gln Leu Ala
        915             920             925

Glu Leu Gly Pro Pro Gly Val Gly Gly Val Gly Ala Cys Lys Leu Gly
930             935             940

Pro Gly Lys Gly Ser Arg Lys Lys Arg Ser Leu Pro Arg Glu Glu Ser
945             950             955             960

Ala Gly Ala Ala Pro Gly Glu Gly Pro Glu Gly Val Asp Gly Arg Val
            965             970             975

Arg Glu Leu Lys Asp Arg Leu Glu Leu Glu Leu Arg Gln Gly Glu
        980             985             990

Glu Gln Tyr Glu Cys Val Leu Lys Arg Lys Glu Gln His Val Ala Glu
            995            1000            1005

Gln Ile Ser Lys Met Met Glu Leu Ala Arg Glu Lys Gln Ala Ala
       1010            1015            1020

Glu Leu Lys Ala Leu Lys Glu Thr Ser Glu Asn Asp Thr Lys Glu
       1025            1030            1035

Met Lys Lys Lys Leu Glu Thr Lys Arg Leu Glu Arg Ile Gln Gly
       1040            1045            1050

Met Thr Lys Val Thr Thr Asp Lys Met Ala Gln Glu Arg Leu Lys
       1055            1060            1065

Arg Glu Ile Asn Asn Ser His Ile Gln Glu Val Val Gln Val Ile
       1070            1075            1080

Lys Gln Met Thr Glu Asn Leu Glu Arg His Gln Glu Lys Leu Glu
       1085            1090            1095

Glu Lys Gln Ala Ala Cys Leu Glu Gln Ile Arg Glu Met Glu Lys
       1100            1105            1110

Gln Phe Gln Lys Glu Ala Leu Ala Glu Tyr Glu Ala Arg Met Lys
       1115            1120            1125

Gly Leu Glu Ala Glu Val Lys Glu Ser Val Arg Ala Cys Leu Arg
       1130            1135            1140

Thr Cys Phe Pro Ser Glu Ala Lys Asp Lys Pro Glu Arg Ala Cys
       1145            1150            1155

Glu Cys Pro Pro Glu Leu Cys Glu Gln Asp Pro Leu Ile Ala Lys
       1160            1165            1170

Ala Asp Ala Gln Glu Ser Arg Leu
```

-continued

```
             1175                1180

<210> SEQ ID NO 18
<211> LENGTH: 1234
<212> TYPE: PRT
<213> ORGANISM: Homo sapiens

<400> SEQUENCE: 18

Met Ala Gly Ala Gln Pro Gly Val His Ala Leu Gln Leu Pro Pro
1               5                   10                  15

Thr Val Val Glu Thr Leu Arg Arg Gly Ser Lys Phe Ile Lys Trp Asp
            20                  25                  30

Glu Glu Thr Ser Ser Arg Asn Leu Val Thr Leu Arg Val Asp Pro Asn
        35                  40                  45

Gly Phe Phe Leu Tyr Trp Thr Gly Pro Asn Met Glu Val Asp Thr Leu
    50                  55                  60

Asp Ile Ser Ser Ile Arg Asp Thr Arg Thr Gly Arg Tyr Ala Arg Leu
65                  70                  75                  80

Pro Lys Asp Pro Lys Ile Arg Glu Val Leu Gly Phe Gly Gly Pro Asp
                85                  90                  95

Ala Arg Leu Glu Glu Lys Leu Met Thr Val Val Ser Gly Pro Asp Pro
            100                 105                 110

Val Asn Thr Val Phe Leu Asn Phe Met Ala Val Gln Asp Asp Thr Ala
        115                 120                 125

Lys Val Trp Ser Glu Glu Leu Phe Lys Leu Ala Met Asn Ile Leu Ala
    130                 135                 140

Gln Asn Ala Ser Arg Asn Thr Phe Leu Arg Lys Ala Tyr Thr Lys Leu
145                 150                 155                 160

Lys Leu Gln Val Asn Gln Asp Gly Arg Ile Pro Val Lys Asn Ile Leu
                165                 170                 175

Lys Met Phe Ser Ala Asp Lys Lys Arg Val Glu Thr Ala Leu Glu Ser
            180                 185                 190

Cys Gly Leu Lys Phe Asn Arg Ser Glu Ser Ile Arg Pro Asp Glu Phe
        195                 200                 205

Ser Leu Glu Ile Phe Glu Arg Phe Leu Asn Lys Leu Cys Leu Arg Pro
    210                 215                 220

Asp Ile Asp Lys Ile Leu Leu Glu Ile Gly Ala Lys Gly Lys Pro Tyr
225                 230                 235                 240

Leu Thr Leu Glu Gln Leu Met Asp Phe Ile Asn Gln Lys Gln Arg Asp
                245                 250                 255

Pro Arg Leu Asn Glu Val Leu Tyr Pro Pro Leu Arg Pro Ser Gln Ala
            260                 265                 270

Arg Leu Leu Ile Glu Lys Tyr Glu Pro Asn Gln Gln Phe Leu Glu Arg
        275                 280                 285

Asp Gln Met Ser Met Glu Gly Phe Ser Arg Tyr Leu Gly Gly Glu Glu
    290                 295                 300

Asn Gly Ile Leu Pro Leu Glu Ala Leu Asp Leu Ser Thr Asp Met Thr
305                 310                 315                 320

Gln Pro Leu Ser Ala Tyr Phe Ile Asn Ser Ser His Asn Thr Tyr Leu
                325                 330                 335

Thr Ala Gly Gln Leu Ala Gly Thr Ser Ser Val Glu Met Tyr Arg Gln
            340                 345                 350

Ala Leu Leu Trp Gly Cys Arg Cys Val Glu Leu Asp Val Trp Lys Gly
        355                 360                 365

Arg Pro Pro Glu Glu Glu Pro Phe Ile Thr His Gly Phe Thr Met Thr
```

```
            370                 375                 380
Thr Glu Val Pro Leu Arg Asp Val Leu Glu Ala Ile Ala Glu Thr Ala
385                 390                 395                 400

Phe Lys Thr Ser Pro Tyr Pro Val Ile Leu Ser Phe Glu Asn His Val
                405                 410                 415

Asp Ser Ala Lys Gln Gln Ala Lys Met Ala Glu Tyr Cys Arg Ser Ile
                420                 425                 430

Phe Gly Asp Ala Leu Leu Ile Glu Pro Leu Asp Lys Tyr Pro Leu Ala
                435                 440                 445

Pro Gly Val Pro Leu Pro Ser Pro Gln Asp Leu Met Gly Arg Ile Leu
450                 455                 460

Val Lys Asn Lys Lys Arg His Arg Pro Ser Ala Gly Gly Pro Asp Ser
465                 470                 475                 480

Ala Gly Arg Lys Arg Pro Leu Glu Gln Ser Asn Ser Ala Leu Ser Glu
                485                 490                 495

Ser Ser Ala Ala Thr Glu Pro Ser Ser Pro Gln Leu Gly Ser Pro Ser
                500                 505                 510

Ser Asp Ser Cys Pro Gly Leu Ser Asn Gly Glu Glu Val Gly Leu Glu
                515                 520                 525

Lys Pro Ser Leu Glu Pro Gln Lys Ser Leu Gly Asp Glu Gly Leu Asn
530                 535                 540

Arg Gly Pro Tyr Val Leu Gly Pro Ala Asp Arg Glu Asp Glu Glu
545                 550                 555                 560

Asp Glu Glu Glu Glu Gln Thr Asp Pro Lys Lys Pro Thr Thr Asp
                565                 570                 575

Glu Gly Thr Ala Ser Ser Glu Val Asn Ala Thr Glu Glu Met Ser Thr
                580                 585                 590

Leu Val Asn Tyr Ile Glu Pro Val Lys Phe Lys Ser Phe Glu Ala Ala
                595                 600                 605

Arg Lys Arg Asn Lys Cys Phe Glu Met Ser Ser Phe Val Glu Thr Lys
610                 615                 620

Ala Met Glu Gln Leu Thr Lys Ser Pro Met Glu Phe Val Glu Tyr Asn
625                 630                 635                 640

Lys Gln Gln Leu Ser Arg Ile Tyr Pro Lys Gly Thr Arg Val Asp Ser
                645                 650                 655

Ser Asn Tyr Met Pro Gln Leu Phe Trp Asn Val Gly Cys Gln Leu Val
                660                 665                 670

Ala Leu Asn Phe Gln Thr Leu Asp Val Ala Met Gln Leu Asn Ala Gly
                675                 680                 685

Val Phe Glu Tyr Asn Gly Arg Ser Gly Tyr Leu Leu Lys Pro Glu Phe
                690                 695                 700

Met Arg Arg Pro Asp Lys Ser Phe Asp Pro Phe Thr Glu Val Ile Val
705                 710                 715                 720

Asp Gly Ile Val Ala Asn Ala Leu Arg Val Lys Val Ile Ser Gly Gln
                725                 730                 735

Phe Leu Ser Asp Arg Lys Val Gly Ile Tyr Val Glu Val Asp Met Phe
                740                 745                 750

Gly Leu Pro Val Asp Thr Arg Arg Lys Tyr Arg Thr Arg Thr Ser Gln
                755                 760                 765

Gly Asn Ser Phe Asn Pro Val Trp Asp Glu Glu Pro Phe Asp Phe Pro
                770                 775                 780

Lys Val Val Leu Pro Thr Leu Ala Ser Leu Arg Ile Ala Ala Phe Glu
785                 790                 795                 800
```

-continued

Glu Gly Gly Lys Phe Val Gly His Arg Ile Leu Pro Val Ser Ala Ile
            805                 810                 815

Arg Ser Gly Tyr His Tyr Val Cys Leu Arg Asn Glu Ala Asn Gln Pro
        820                 825                 830

Leu Cys Leu Pro Ala Leu Leu Ile Tyr Thr Glu Ala Ser Asp Tyr Ile
        835                 840                 845

Pro Asp Asp His Gln Asp Tyr Ala Glu Ala Leu Ile Asn Pro Ile Lys
        850                 855                 860

His Val Ser Leu Met Asp Gln Arg Ala Arg Gln Leu Ala Ala Leu Ile
865                 870                 875                 880

Gly Glu Ser Glu Ala Gln Ala Gly Gln Glu Thr Cys Gln Asp Thr Gln
            885                 890                 895

Ser Gln Gln Leu Gly Ser Gln Pro Ser Ser Asn Pro Thr Pro Ser Pro
        900                 905                 910

Leu Asp Ala Ser Pro Arg Arg Pro Pro Gly Pro Thr Thr Ser Pro Ala
        915                 920                 925

Ser Thr Ser Leu Ser Ser Pro Gly Gln Arg Asp Asp Leu Ile Ala Ser
        930                 935                 940

Ile Leu Ser Glu Val Ala Pro Thr Pro Leu Asp Glu Leu Arg Gly His
945                 950                 955                 960

Lys Ala Leu Val Lys Leu Arg Ser Arg Gln Glu Arg Asp Leu Arg Glu
            965                 970                 975

Leu Arg Lys Lys His Gln Arg Lys Ala Val Thr Leu Thr Arg Arg Leu
        980                 985                 990

Leu Asp Gly Leu Ala Gln Ala Gln Ala Glu Gly Arg Cys Arg Leu Arg
        995                 1000                1005

Pro Gly Ala Leu Gly Gly Ala Ala Asp Val Glu Asp Thr Lys Glu
   1010                1015                1020

Gly Glu Asp Glu Ala Lys Arg Tyr Gln Glu Phe Gln Asn Arg Gln
   1025                1030                1035

Val Gln Ser Leu Leu Glu Leu Arg Glu Ala Gln Val Asp Ala Glu
   1040                1045                1050

Ala Gln Arg Arg Leu Glu His Leu Arg Gln Ala Leu Gln Arg Leu
   1055                1060                1065

Arg Glu Val Val Leu Asp Ala Asn Thr Thr Gln Phe Lys Arg Leu
   1070                1075                1080

Lys Glu Met Asn Glu Arg Glu Lys Lys Glu Leu Gln Lys Ile Leu
   1085                1090                1095

Asp Arg Lys Arg His Asn Ser Ile Ser Glu Ala Lys Met Arg Asp
   1100                1105                1110

Lys His Lys Lys Glu Ala Glu Leu Thr Glu Ile Asn Arg Arg His
   1115                1120                1125

Ile Thr Glu Ser Val Asn Ser Ile Arg Arg Leu Glu Glu Ala Gln
   1130                1135                1140

Lys Gln Arg His Asp Arg Leu Val Ala Gly Gln Gln Gln Val Leu
   1145                1150                1155

Gln Gln Leu Ala Glu Glu Glu Pro Lys Leu Leu Ala Gln Leu Ala
   1160                1165                1170

Gln Glu Cys Gln Glu Gln Arg Ala Arg Leu Pro Gln Glu Ile Arg
   1175                1180                1185

Arg Ser Leu Leu Gly Glu Met Pro Glu Gly Leu Gly Asp Gly Pro
   1190                1195                1200

Leu Val Ala Cys Ala Ser Asn Gly His Ala Pro Gly Ser Ser Gly
   1205                1210                1215

His Leu Ser Gly Ala Asp Ser Glu Ser Gln Glu Glu Asn Thr Gln
    1220            1225            1230

Leu

<210> SEQ ID NO 19
<211> LENGTH: 1194
<212> TYPE: PRT
<213> ORGANISM: Homo sapiens

<400> SEQUENCE: 19

Met Ala Lys Pro Tyr Glu Phe Asn Trp Gln Lys Glu Val Pro Ser Phe
1               5                   10                  15

Leu Gln Glu Gly Thr Val Phe Asp Arg Tyr Glu Glu Glu Ser Phe Val
            20                  25                  30

Phe Glu Pro Asn Cys Leu Phe Lys Val Asp Glu Phe Gly Phe Phe Leu
        35                  40                  45

Thr Trp Arg Ser Glu Gly Lys Glu Gly Gln Val Leu Glu Cys Ser Leu
50                  55                  60

Ile Asn Ser Ile Arg Ser Gly Ala Ile Pro Lys Asp Pro Lys Ile Leu
65                  70                  75                  80

Ala Ala Leu Glu Ala Val Gly Lys Ser Glu Asn Asp Leu Glu Gly Arg
                85                  90                  95

Ile Val Cys Val Cys Ser Gly Thr Asp Leu Val Asn Ile Ser Phe Thr
            100                 105                 110

Tyr Met Val Ala Glu Asn Pro Glu Val Thr Lys Gln Trp Val Glu Gly
        115                 120                 125

Leu Arg Ser Ile Ile His Asn Phe Arg Ala Asn Asn Val Ser Pro Met
130                 135                 140

Thr Cys Leu Lys Lys His Trp Met Lys Leu Ala Phe Met Thr Asn Thr
145                 150                 155                 160

Asn Gly Lys Ile Pro Val Arg Ser Ile Thr Arg Thr Phe Ala Ser Gly
                165                 170                 175

Lys Thr Glu Lys Val Ile Phe Gln Ala Leu Lys Glu Leu Gly Leu Pro
            180                 185                 190

Ser Gly Lys Asn Asp Glu Ile Glu Pro Thr Ala Phe Ser Tyr Glu Lys
        195                 200                 205

Phe Tyr Glu Leu Thr Gln Lys Ile Cys Pro Arg Thr Asp Ile Glu Asp
210                 215                 220

Leu Phe Lys Lys Ile Asn Gly Asp Lys Thr Asp Tyr Leu Thr Val Asp
225                 230                 235                 240

Gln Leu Val Ser Phe Leu Asn Glu His Gln Arg Asp Pro Arg Leu Asn
                245                 250                 255

Glu Ile Leu Phe Pro Phe Tyr Asp Ala Lys Arg Ala Met Gln Ile Ile
            260                 265                 270

Glu Met Tyr Glu Pro Asp Glu Asp Leu Lys Lys Lys Gly Leu Ile Ser
        275                 280                 285

Ser Asp Gly Phe Cys Arg Tyr Leu Met Ser Asp Glu Asn Ala Pro Val
290                 295                 300

Phe Leu Asp Arg Leu Glu Leu Tyr Gln Glu Met Asp His Pro Leu Ala
305                 310                 315                 320

His Tyr Phe Ile Ser Ser Ser His Asn Thr Tyr Leu Thr Gly Arg Gln
                325                 330                 335

Phe Gly Gly Lys Ser Ser Val Glu Met Tyr Arg Gln Val Leu Leu Ala
            340                 345                 350

-continued

```
Gly Cys Arg Cys Val Glu Leu Asp Cys Trp Asp Gly Lys Gly Glu Asp
            355                 360                 365

Gln Glu Pro Ile Ile Thr His Gly Lys Ala Met Cys Thr Asp Ile Leu
    370                 375                 380

Phe Lys Asp Val Ile Gln Ala Ile Lys Glu Thr Ala Phe Val Thr Ser
385                 390                 395                 400

Glu Tyr Pro Val Ile Leu Ser Phe Glu Asn His Cys Ser Lys Tyr Gln
                405                 410                 415

Gln Tyr Lys Met Ser Lys Tyr Cys Glu Asp Leu Phe Gly Asp Leu Leu
            420                 425                 430

Leu Lys Gln Ala Leu Glu Ser His Pro Leu Glu Pro Gly Arg Ala Leu
        435                 440                 445

Pro Ser Pro Asn Asp Leu Lys Arg Lys Ile Leu Ile Lys Asn Lys Arg
    450                 455                 460

Leu Lys Pro Glu Val Glu Lys Lys Gln Leu Glu Ala Leu Arg Ser Met
465                 470                 475                 480

Met Glu Ala Gly Glu Ser Ala Ser Pro Ala Asn Ile Leu Glu Asp Asp
                485                 490                 495

Asn Glu Glu Glu Ile Glu Ser Ala Asp Gln Glu Glu Glu Ala His Pro
            500                 505                 510

Glu Phe Lys Phe Gly Asn Glu Leu Ser Ala Asp Asp Leu Gly His Lys
        515                 520                 525

Glu Ala Val Ala Asn Ser Val Lys Lys Gly Leu Val Thr Val Glu Asp
    530                 535                 540

Glu Gln Ala Trp Met Ala Ser Tyr Lys Tyr Val Gly Ala Thr Thr Asn
545                 550                 555                 560

Ile His Pro Tyr Leu Ser Thr Met Ile Asn Tyr Ala Gln Pro Val Lys
                565                 570                 575

Phe Gln Gly Phe His Val Ala Glu Glu Arg Asn Ile His Tyr Asn Met
            580                 585                 590

Ser Ser Phe Asn Glu Ser Val Gly Leu Gly Tyr Leu Lys Thr His Ala
        595                 600                 605

Ile Glu Phe Val Asn Tyr Asn Lys Arg Gln Met Ser Arg Ile Tyr Pro
    610                 615                 620

Lys Gly Gly Arg Val Asp Ser Ser Asn Tyr Met Pro Gln Ile Phe Trp
625                 630                 635                 640

Asn Ala Gly Cys Gln Met Val Ser Leu Asn Tyr Gln Thr Pro Asp Leu
                645                 650                 655

Ala Met Gln Leu Asn Gln Gly Lys Phe Glu Tyr Asn Gly Ser Cys Gly
            660                 665                 670

Tyr Leu Leu Lys Pro Asp Phe Met Arg Arg Pro Asp Arg Thr Phe Asp
        675                 680                 685

Pro Phe Ser Glu Thr Pro Val Asp Gly Val Ile Ala Ala Thr Cys Ser
    690                 695                 700

Val Gln Val Ile Ser Gly Gln Phe Leu Ser Asp Lys Lys Ile Gly Thr
705                 710                 715                 720

Tyr Val Glu Val Asp Met Tyr Gly Leu Pro Thr Asp Thr Ile Arg Lys
                725                 730                 735

Glu Phe Arg Thr Arg Met Val Met Asn Asn Gly Leu Asn Pro Val Tyr
            740                 745                 750

Asn Glu Glu Ser Phe Val Phe Arg Lys Val Ile Leu Pro Asp Leu Ala
        755                 760                 765

Val Leu Arg Ile Ala Val Tyr Asp Asp Asn Asn Lys Leu Ile Gly Gln
    770                 775                 780
```

```
Arg Ile Leu Pro Leu Asp Gly Leu Gln Ala Gly Tyr Arg His Ile Ser
785                 790                 795                 800

Leu Arg Asn Glu Gly Asn Lys Pro Leu Ser Leu Pro Thr Ile Phe Cys
            805                 810                 815

Asn Ile Val Leu Lys Thr Tyr Val Pro Asp Gly Phe Gly Asp Ile Val
            820                 825                 830

Asp Ala Leu Ser Asp Pro Lys Lys Phe Leu Ser Ile Thr Glu Lys Arg
            835                 840                 845

Ala Asp Gln Met Arg Ala Met Gly Ile Glu Thr Ser Asp Ile Ala Asp
850                 855                 860

Val Pro Ser Asp Thr Ser Lys Asn Asp Lys Lys Gly Lys Ala Asn Thr
865                 870                 875                 880

Ala Lys Ala Asn Val Thr Pro Gln Ser Ser Glu Leu Arg Pro Thr
                885                 890                 895

Thr Thr Ala Ala Leu Ala Ser Gly Val Glu Ala Lys Lys Gly Ile Glu
            900                 905                 910

Leu Ile Pro Gln Val Arg Ile Glu Asp Leu Lys Gln Met Lys Ala Tyr
            915                 920                 925

Leu Lys His Leu Lys Lys Gln Gln Lys Glu Leu Asn Ser Leu Lys Lys
            930                 935                 940

Lys His Ala Lys Glu His Ser Thr Met Gln Lys Leu His Cys Thr Gln
945                 950                 955                 960

Val Asp Lys Ile Val Ala Gln Tyr Asp Lys Glu Lys Ser Thr His Glu
            965                 970                 975

Lys Ile Leu Glu Lys Ala Met Lys Lys Gly Gly Ser Asn Cys Leu
            980                 985                 990

Glu Met Lys Lys Glu Thr Glu Ile Lys Ile Gln Thr Leu Thr Ser Asp
            995                 1000                1005

His Lys Ser Lys Val Lys Glu Ile Val Ala Gln His Thr Lys Glu
    1010                1015                1020

Trp Ser Glu Met Ile Asn Thr His Ser Ala Glu Glu Gln Glu Ile
    1025                1030                1035

Arg Asp Leu His Leu Ser Gln Gln Cys Glu Leu Leu Lys Lys Leu
    1040                1045                1050

Leu Ile Asn Ala His Glu Gln Gln Thr Gln Gln Leu Lys Leu Ser
    1055                1060                1065

His Asp Arg Glu Ser Lys Glu Met Arg Ala His Gln Ala Lys Ile
    1070                1075                1080

Ser Met Glu Asn Ser Lys Ala Ile Ser Gln Asp Lys Ser Ile Lys
    1085                1090                1095

Asn Lys Ala Glu Arg Glu Arg Arg Val Arg Glu Leu Asn Ser Ser
    1100                1105                1110

Asn Thr Lys Lys Phe Leu Glu Arg Lys Arg Leu Ala Met Lys
    1115                1120                1125

Gln Ser Lys Glu Met Asp Gln Leu Lys Lys Val Gln Leu Glu His
    1130                1135                1140

Leu Glu Phe Leu Glu Lys Gln Asn Glu Gln Leu Leu Lys Ser Cys
    1145                1150                1155

His Ala Val Ser Gln Thr Gln Gly Glu Gly Asp Ala Ala Asp Gly
    1160                1165                1170

Glu Ile Gly Ser Arg Asp Gly Pro Gln Thr Ser Asn Ser Ser Met
    1175                1180                1185

Lys Leu Gln Asn Ala Asn
```

-continued

1190

<210> SEQ ID NO 20
<211> LENGTH: 1290
<212> TYPE: PRT
<213> ORGANISM: Homo sapiens

<400> SEQUENCE: 20

Met Ala Gly Ala Ala Ser Pro Cys Ala Asn Gly Cys Gly Pro Gly Ala
1               5                   10                  15

Pro Ser Asp Ala Glu Val Leu His Leu Cys Arg Ser Leu Glu Val Gly
            20                  25                  30

Thr Val Met Thr Leu Phe Tyr Ser Lys Lys Ser Gln Arg Pro Glu Arg
        35                  40                  45

Lys Thr Phe Gln Val Lys Leu Glu Thr Arg Gln Ile Thr Trp Ser Arg
50                  55                  60

Gly Ala Asp Lys Ile Glu Gly Ala Ile Asp Ile Arg Glu Ile Lys Glu
65                  70                  75                  80

Ile Arg Pro Gly Lys Thr Ser Arg Asp Phe Asp Arg Tyr Gln Glu Asp
                85                  90                  95

Pro Ala Phe Arg Pro Asp Gln Ser His Cys Phe Val Ile Leu Tyr Gly
            100                 105                 110

Met Glu Phe Arg Leu Lys Thr Leu Ser Leu Gln Ala Thr Ser Glu Asp
        115                 120                 125

Glu Val Asn Met Trp Ile Lys Gly Leu Thr Trp Leu Met Glu Asp Thr
130                 135                 140

Leu Gln Ala Pro Thr Pro Leu Gln Ile Glu Arg Trp Leu Arg Lys Gln
145                 150                 155                 160

Phe Tyr Ser Val Asp Arg Asn Arg Glu Asp Arg Ile Ser Ala Lys Asp
                165                 170                 175

Leu Lys Asn Met Leu Ser Gln Val Asn Tyr Arg Val Pro Asn Met Arg
            180                 185                 190

Phe Leu Arg Glu Arg Leu Thr Asp Leu Glu Gln Arg Ser Gly Asp Ile
        195                 200                 205

Thr Tyr Gly Gln Phe Ala Gln Leu Tyr Arg Ser Leu Met Tyr Ser Ala
210                 215                 220

Gln Lys Thr Met Asp Leu Pro Phe Leu Glu Ala Ser Thr Leu Arg Ala
225                 230                 235                 240

Gly Glu Arg Pro Glu Leu Cys Arg Val Ser Leu Pro Glu Phe Gln Gln
                245                 250                 255

Phe Leu Leu Asp Tyr Gln Gly Glu Leu Trp Ala Val Asp Arg Leu Gln
            260                 265                 270

Val Gln Glu Phe Met Leu Ser Phe Leu Arg Asp Pro Leu Arg Glu Ile
        275                 280                 285

Glu Glu Pro Tyr Phe Phe Leu Asp Glu Phe Val Thr Phe Leu Phe Ser
290                 295                 300

Lys Glu Asn Ser Val Trp Asn Ser Gln Leu Asp Ala Val Cys Pro Asp
305                 310                 315                 320

Thr Met Asn Asn Pro Leu Ser His Tyr Trp Ile Ser Ser Ser His Asn
                325                 330                 335

Thr Tyr Leu Thr Gly Asp Gln Phe Ser Ser Glu Ser Ser Leu Glu Ala
            340                 345                 350

Tyr Ala Arg Cys Leu Arg Met Gly Cys Arg Cys Ile Glu Leu Asp Cys
        355                 360                 365

Trp Asp Gly Pro Asp Gly Met Pro Val Ile Tyr His Gly His Thr Leu

-continued

```
                370                 375                 380
Thr Thr Lys Ile Lys Phe Ser Asp Val Leu His Thr Ile Lys Glu His
385                 390                 395                 400

Ala Phe Val Ala Ser Glu Tyr Pro Val Ile Leu Ser Ile Glu Asp His
                405                 410                 415

Cys Ser Ile Ala Gln Gln Arg Asn Met Ala Gln Tyr Phe Lys Lys Val
                420                 425                 430

Leu Gly Asp Thr Leu Leu Thr Lys Pro Val Glu Ile Ser Ala Asp Gly
                435                 440                 445

Leu Pro Ser Pro Asn Gln Leu Lys Arg Lys Ile Leu Ile Lys His Lys
450                 455                 460

Lys Leu Ala Glu Gly Ser Ala Tyr Glu Glu Val Pro Thr Ser Met Met
465                 470                 475                 480

Tyr Ser Glu Asn Asp Ile Ser Asn Ser Ile Lys Asn Gly Ile Leu Tyr
                485                 490                 495

Leu Glu Asp Pro Val Asn His Glu Trp Tyr Pro His Tyr Phe Val Leu
                500                 505                 510

Thr Ser Ser Lys Ile Tyr Tyr Ser Glu Glu Thr Ser Ser Asp Gln Gly
                515                 520                 525

Asn Glu Asp Glu Glu Pro Lys Glu Val Ser Ser Thr Glu Leu
530                 535                 540

His Ser Asn Glu Lys Trp Phe His Gly Lys Leu Gly Ala Gly Arg Asp
545                 550                 555                 560

Gly Arg His Ile Ala Glu Arg Leu Leu Thr Glu Tyr Cys Ile Glu Thr
                565                 570                 575

Gly Ala Pro Asp Gly Ser Phe Leu Val Arg Glu Ser Glu Thr Phe Val
                580                 585                 590

Gly Asp Tyr Thr Leu Ser Phe Trp Arg Asn Gly Lys Val Gln His Cys
                595                 600                 605

Arg Ile His Ser Arg Gln Asp Ala Gly Thr Pro Lys Phe Phe Leu Thr
                610                 615                 620

Asp Asn Leu Val Phe Asp Ser Leu Tyr Asp Leu Ile Thr His Tyr Gln
625                 630                 635                 640

Gln Val Pro Leu Arg Cys Asn Glu Phe Glu Met Arg Leu Ser Glu Pro
                645                 650                 655

Val Pro Gln Thr Asn Ala His Glu Ser Lys Glu Trp Tyr His Ala Ser
                660                 665                 670

Leu Thr Arg Ala Gln Ala Glu His Met Leu Met Arg Val Pro Arg Asp
                675                 680                 685

Gly Ala Phe Leu Val Arg Lys Arg Asn Glu Pro Asn Ser Tyr Ala Ile
                690                 695                 700

Ser Phe Arg Ala Glu Gly Lys Ile Lys His Cys Arg Val Gln Gln Glu
705                 710                 715                 720

Gly Gln Thr Val Met Leu Gly Asn Ser Glu Phe Asp Ser Leu Val Asp
                725                 730                 735

Leu Ile Ser Tyr Tyr Glu Lys His Pro Leu Tyr Arg Lys Met Lys Leu
                740                 745                 750

Arg Tyr Pro Ile Asn Glu Glu Ala Leu Glu Lys Ile Gly Thr Ala Glu
                755                 760                 765

Pro Asp Tyr Gly Ala Leu Tyr Glu Gly Arg Asn Pro Gly Phe Tyr Val
                770                 775                 780

Glu Ala Asn Pro Met Pro Thr Phe Lys Cys Ala Val Lys Ala Leu Phe
785                 790                 795                 800
```

-continued

```
Asp Tyr Lys Ala Gln Arg Glu Asp Glu Leu Thr Phe Ile Lys Ser Ala
            805                 810                 815

Ile Ile Gln Asn Val Glu Lys Gln Glu Gly Gly Trp Trp Arg Gly Asp
        820                 825                 830

Tyr Gly Gly Lys Lys Gln Leu Trp Phe Pro Ser Asn Tyr Val Glu Glu
        835                 840                 845

Met Val Asn Pro Val Ala Leu Glu Pro Glu Arg Glu His Leu Asp Glu
    850                 855                 860

Asn Ser Pro Leu Gly Asp Leu Leu Arg Gly Val Leu Asp Val Pro Ala
865                 870                 875                 880

Cys Gln Ile Ala Ile Arg Pro Glu Gly Lys Asn Asn Arg Leu Phe Val
            885                 890                 895

Phe Ser Ile Ser Met Ala Ser Val Ala His Trp Ser Leu Asp Val Ala
            900                 905                 910

Ala Asp Ser Gln Glu Glu Leu Gln Asp Trp Val Lys Lys Ile Arg Glu
        915                 920                 925

Val Ala Gln Thr Ala Asp Ala Arg Leu Thr Glu Gly Lys Ile Met Glu
    930                 935                 940

Arg Arg Lys Lys Ile Ala Leu Glu Leu Ser Glu Leu Val Val Tyr Cys
945                 950                 955                 960

Arg Pro Val Pro Phe Asp Glu Glu Lys Ile Gly Thr Glu Arg Ala Cys
            965                 970                 975

Tyr Arg Asp Met Ser Ser Phe Pro Glu Thr Lys Ala Glu Lys Tyr Val
        980                 985                 990

Asn Lys Ala Lys Gly Lys Lys Phe Leu Gln Tyr Asn Arg Leu Gln Leu
        995                 1000                1005

Ser Arg Ile Tyr Pro Lys Gly Gln Arg Leu Asp Ser Ser Asn Tyr
    1010                1015                1020

Asp Pro Leu Pro Met Trp Ile Cys Gly Ser Gln Leu Val Ala Leu
    1025                1030                1035

Asn Phe Gln Thr Pro Asp Lys Pro Met Gln Met Asn Gln Ala Leu
    1040                1045                1050

Phe Met Thr Gly Arg His Cys Gly Tyr Val Leu Gln Pro Ser Thr
    1055                1060                1065

Met Arg Asp Glu Ala Phe Asp Pro Phe Asp Lys Ser Ser Leu Arg
    1070                1075                1080

Gly Leu Glu Pro Cys Ala Ile Ser Ile Glu Val Leu Gly Ala Arg
    1085                1090                1095

His Leu Pro Lys Asn Gly Arg Gly Ile Val Cys Pro Phe Val Glu
    1100                1105                1110

Ile Glu Val Ala Gly Ala Glu Tyr Asp Ser Thr Lys Gln Lys Thr
    1115                1120                1125

Glu Phe Val Val Asp Asn Gly Leu Asn Pro Val Trp Pro Ala Lys
    1130                1135                1140

Pro Phe His Phe Gln Ile Ser Asn Pro Glu Phe Ala Phe Leu Arg
    1145                1150                1155

Phe Val Val Tyr Glu Glu Asp Met Phe Ser Asp Gln Asn Phe Leu
    1160                1165                1170

Ala Gln Ala Thr Phe Pro Val Lys Gly Leu Lys Thr Gly Tyr Arg
    1175                1180                1185

Ala Val Pro Leu Lys Asn Asn Tyr Ser Glu Asp Leu Glu Leu Ala
    1190                1195                1200

Ser Leu Leu Ile Lys Ile Asp Ile Phe Pro Ala Lys Glu Asn Gly
    1205                1210                1215
```

```
Asp Leu Ser Pro Phe Ser Gly Thr Ser Leu Arg Glu Arg Gly Ser
    1220                1225                1230

Asp Ala Ser Gly Gln Leu Phe His Gly Arg Ala Arg Glu Gly Ser
    1235                1240                1245

Phe Glu Ser Arg Tyr Gln Gln Pro Phe Glu Asp Phe Arg Ile Ser
    1250                1255                1260

Gln Glu His Leu Ala Asp His Phe Asp Ser Arg Glu Arg Arg Ala
    1265                1270                1275

Pro Arg Arg Thr Arg Val Asn Gly Asp Asn Arg Leu
    1280                1285                1290

<210> SEQ ID NO 21
<211> LENGTH: 1265
<212> TYPE: PRT
<213> ORGANISM: Homo sapiens

<400> SEQUENCE: 21

Met Ser Thr Thr Val Asn Val Asp Ser Leu Ala Glu Tyr Glu Lys Ser
1               5                   10                  15

Gln Ile Lys Arg Ala Leu Glu Leu Gly Thr Val Met Thr Val Phe Ser
            20                  25                  30

Phe Arg Lys Ser Thr Pro Glu Arg Arg Thr Val Gln Val Ile Met Glu
        35                  40                  45

Thr Arg Gln Val Ala Trp Ser Lys Thr Ala Asp Lys Ile Glu Gly Phe
    50                  55                  60

Leu Asp Ile Met Glu Ile Lys Glu Ile Arg Pro Gly Lys Asn Ser Lys
65                  70                  75                  80

Asp Phe Glu Arg Ala Lys Ala Val Arg Gln Lys Glu Asp Cys Cys Phe
                85                  90                  95

Thr Ile Leu Tyr Gly Thr Gln Phe Val Leu Ser Thr Leu Ser Leu Ala
            100                 105                 110

Ala Asp Ser Lys Glu Asp Ala Val Asn Trp Leu Ser Gly Leu Lys Ile
        115                 120                 125

Leu His Gln Glu Ala Met Asn Ala Ser Thr Pro Thr Ile Ile Glu Ser
    130                 135                 140

Trp Leu Arg Lys Gln Ile Tyr Ser Val Asp Gln Thr Arg Arg Asn Ser
145                 150                 155                 160

Ile Ser Leu Arg Glu Leu Lys Thr Ile Leu Pro Leu Ile Asn Phe Lys
                165                 170                 175

Val Ser Ser Ala Lys Phe Leu Lys Asp Lys Phe Val Glu Ile Gly Ala
            180                 185                 190

His Lys Asp Glu Leu Ser Phe Glu Gln Phe His Leu Phe Tyr Lys Lys
        195                 200                 205

Leu Met Phe Glu Gln Gln Lys Ser Ile Leu Asp Glu Phe Lys Lys Asp
    210                 215                 220

Ser Ser Val Phe Ile Leu Gly Asn Thr Asp Arg Pro Asp Ala Ser Ala
225                 230                 235                 240

Val Tyr Leu Arg Asp Phe Gln Arg Phe Leu Ile His Glu Gln Gln Glu
                245                 250                 255

His Trp Ala Gln Asp Leu Asn Lys Val Arg Glu Arg Met Thr Lys Phe
            260                 265                 270

Ile Asp Asp Thr Met Arg Glu Thr Ala Glu Pro Phe Leu Phe Val Asp
        275                 280                 285

Glu Phe Leu Thr Tyr Leu Phe Ser Arg Glu Asn Ser Ile Trp Asp Glu
    290                 295                 300
```

```
Lys Tyr Asp Ala Val Asp Met Gln Asp Met Asn Asn Pro Leu Ser His
305                 310                 315                 320

Tyr Trp Ile Ser Ser Ser His Asn Thr Tyr Leu Thr Gly Asp Gln Leu
            325                 330                 335

Arg Ser Glu Ser Ser Pro Glu Ala Tyr Ile Arg Cys Leu Arg Met Gly
            340                 345                 350

Cys Arg Cys Ile Glu Leu Asp Cys Trp Asp Gly Pro Asp Gly Lys Pro
            355                 360                 365

Val Ile Tyr His Gly Trp Thr Arg Thr Thr Lys Ile Lys Phe Asp Asp
370                 375                 380

Val Val Gln Ala Ile Lys Asp His Ala Phe Val Thr Ser Ser Phe Pro
385                 390                 395                 400

Val Ile Leu Ser Ile Glu Glu His Cys Ser Val Glu Gln Gln Arg His
                405                 410                 415

Met Ala Lys Ala Phe Lys Glu Val Phe Gly Asp Leu Leu Leu Thr Lys
                420                 425                 430

Pro Thr Glu Ala Ser Ala Asp Gln Leu Pro Ser Pro Ser Gln Leu Arg
        435                 440                 445

Glu Lys Ile Ile Ile Lys His Lys Lys Leu Gly Pro Arg Gly Asp Val
        450                 455                 460

Asp Val Asn Met Glu Asp Lys Lys Asp Glu His Lys Gln Gln Gly Glu
465                 470                 475                 480

Leu Tyr Met Trp Asp Ser Ile Asp Gln Lys Trp Thr Arg His Tyr Cys
                485                 490                 495

Ala Ile Ala Asp Ala Lys Leu Ser Phe Ser Asp Asp Ile Glu Gln Thr
                500                 505                 510

Met Glu Glu Val Pro Gln Asp Ile Pro Pro Thr Glu Leu His Phe
                515                 520                 525

Gly Glu Lys Trp Phe His Lys Lys Val Glu Lys Arg Thr Ser Ala Glu
        530                 535                 540

Lys Leu Leu Gln Glu Tyr Cys Met Glu Thr Gly Gly Lys Asp Gly Thr
545                 550                 555                 560

Phe Leu Val Arg Glu Ser Glu Thr Phe Pro Asn Asp Tyr Thr Leu Ser
                565                 570                 575

Phe Trp Arg Ser Gly Arg Val Gln His Cys Arg Ile Arg Ser Thr Met
            580                 585                 590

Glu Gly Gly Thr Leu Lys Tyr Tyr Leu Thr Asp Asn Leu Thr Phe Ser
                595                 600                 605

Ser Ile Tyr Ala Leu Ile Gln His Tyr Arg Glu Thr His Leu Arg Cys
610                 615                 620

Ala Glu Phe Glu Leu Arg Leu Thr Asp Pro Val Pro Asn Pro Asn Pro
625                 630                 635                 640

His Glu Ser Lys Pro Trp Tyr Tyr Asp Ser Leu Ser Arg Gly Glu Ala
                645                 650                 655

Glu Asp Met Leu Met Arg Ile Pro Arg Asp Gly Ala Phe Leu Ile Arg
            660                 665                 670

Lys Arg Glu Gly Ser Asp Ser Tyr Ala Ile Thr Phe Arg Ala Arg Gly
            675                 680                 685

Lys Val Lys His Cys Arg Ile Asn Arg Asp Gly Arg His Phe Val Leu
            690                 695                 700

Gly Thr Ser Ala Tyr Phe Glu Ser Leu Val Glu Leu Val Ser Tyr Tyr
705                 710                 715                 720

Glu Lys His Ser Leu Tyr Arg Lys Met Arg Leu Arg Tyr Pro Val Thr
```

-continued

```
                725                 730                 735
Pro Glu Leu Leu Glu Arg Tyr Asn Met Glu Arg Asp Ile Asn Ser Leu
            740                 745                 750
Tyr Asp Val Ser Arg Met Tyr Val Asp Pro Ser Glu Ile Asn Pro Ser
            755                 760                 765
Met Pro Gln Arg Thr Val Lys Ala Leu Tyr Asp Tyr Lys Ala Lys Arg
            770                 775                 780
Ser Asp Glu Leu Ser Phe Cys Arg Gly Ala Leu Ile His Asn Val Ser
785                 790                 795                 800
Lys Glu Pro Gly Gly Trp Trp Lys Gly Asp Tyr Gly Thr Arg Ile Gln
            805                 810                 815
Gln Tyr Phe Pro Ser Asn Tyr Val Glu Asp Ile Ser Thr Ala Asp Phe
            820                 825                 830
Glu Glu Leu Glu Lys Gln Ile Ile Glu Asp Asn Pro Leu Gly Ser Leu
            835                 840                 845
Cys Arg Gly Ile Leu Asp Leu Asn Thr Tyr Asn Val Val Lys Ala Pro
            850                 855                 860
Gln Gly Lys Asn Gln Lys Ser Phe Val Phe Ile Leu Glu Pro Lys Gln
865                 870                 875                 880
Gln Gly Tyr Pro Pro Val Glu Phe Ala Thr Asp Arg Val Glu Glu Leu
            885                 890                 895
Phe Glu Trp Phe Gln Ser Ile Arg Glu Ile Thr Trp Lys Ile Asp Thr
            900                 905                 910
Lys Glu Asn Asn Met Lys Tyr Trp Glu Lys Asn Gln Ser Ile Ala Ile
            915                 920                 925
Glu Leu Ser Asp Leu Val Val Tyr Cys Lys Pro Thr Ser Lys Thr Lys
            930                 935                 940
Asp Asn Leu Glu Asn Pro Asp Phe Arg Glu Ile Arg Ser Phe Val Glu
945                 950                 955                 960
Thr Lys Ala Asp Ser Ile Ile Arg Gln Lys Pro Val Asp Leu Leu Lys
            965                 970                 975
Tyr Asn Gln Lys Gly Leu Thr Arg Val Tyr Pro Lys Gly Gln Arg Val
            980                 985                 990
Asp Ser Ser Asn Tyr Asp Pro Phe Arg Leu Trp Leu Cys Gly Ser Gln
            995                 1000                1005
Met Val Ala Leu Asn Phe Gln Thr Ala Asp Lys Tyr Met Gln Met
            1010                1015                1020
Asn His Ala Leu Phe Ser Leu Asn Gly Arg Thr Gly Tyr Val Leu
            1025                1030                1035
Gln Pro Glu Ser Met Arg Thr Glu Lys Tyr Asp Pro Met Pro Pro
            1040                1045                1050
Glu Ser Gln Arg Lys Ile Leu Met Thr Leu Thr Val Lys Val Leu
            1055                1060                1065
Gly Ala Arg His Leu Pro Lys Leu Gly Arg Ser Ile Ala Cys Pro
            1070                1075                1080
Phe Val Glu Val Glu Ile Cys Gly Ala Glu Tyr Asp Asn Asn Lys
            1085                1090                1095
Phe Lys Thr Thr Val Val Asn Asp Asn Gly Leu Ser Pro Ile Trp
            1100                1105                1110
Ala Pro Thr Gln Glu Lys Val Thr Phe Glu Ile Tyr Asp Pro Asn
            1115                1120                1125
Leu Ala Phe Leu Arg Phe Val Val Tyr Glu Glu Asp Met Phe Ser
            1130                1135                1140
```

```
Asp Pro Asn Phe Leu Ala His Ala Thr Tyr Pro Ile Lys Ala Val
    1145                1150                1155

Lys Ser Gly Phe Arg Ser Val Pro Leu Lys Asn Gly Tyr Ser Glu
    1160                1165                1170

Asp Ile Glu Leu Ala Ser Leu Leu Val Phe Cys Glu Met Arg Pro
    1175                1180                1185

Val Leu Glu Ser Glu Glu Leu Tyr Ser Ser Cys Arg Gln Leu
    1190                1195                1200

Arg Arg Arg Gln Glu Glu Leu Asn Asn Gln Leu Phe Leu Tyr Asp
    1205                1210                1215

Thr His Gln Asn Leu Arg Asn Ala Asn Arg Asp Ala Leu Val Lys
    1220                1225                1230

Glu Phe Ser Val Asn Glu Asn Gln Leu Gln Leu Tyr Gln Glu Lys
    1235                1240                1245

Cys Asn Lys Arg Leu Arg Glu Lys Arg Val Ser Asn Ser Lys Phe
    1250                1255                1260

Tyr Ser
    1265

<210> SEQ ID NO 22
<211> LENGTH: 1002
<212> TYPE: PRT
<213> ORGANISM: Homo sapiens

<400> SEQUENCE: 22

Met Ala Asp Leu Glu Val Tyr Lys Asn Leu Ser Pro Glu Lys Val Glu
1               5                   10                  15

Arg Cys Met Ser Val Met Gln Ser Gly Thr Gln Met Ile Lys Leu Lys
            20                  25                  30

Arg Gly Thr Lys Gly Leu Val Arg Leu Phe Tyr Leu Asp Glu His Arg
        35                  40                  45

Thr Arg Leu Arg Trp Arg Pro Ser Arg Lys Ser Glu Lys Ala Lys Ile
    50                  55                  60

Leu Ile Asp Ser Ile Tyr Lys Val Thr Glu Gly Arg Gln Ser Glu Ile
65                  70                  75                  80

Phe His Arg Gln Ala Glu Gly Asn Phe Asp Pro Ser Cys Cys Phe Thr
                85                  90                  95

Ile Tyr His Gly Asn His Met Glu Ser Leu Asp Leu Ile Thr Ser Asn
            100                 105                 110

Pro Glu Glu Ala Arg Thr Trp Ile Thr Gly Leu Lys Tyr Leu Met Ala
        115                 120                 125

Gly Ile Ser Asp Glu Asp Ser Leu Ala Lys Arg Gln Arg Thr His Asp
    130                 135                 140

Gln Trp Val Lys Gln Thr Phe Glu Glu Ala Asp Lys Asn Gly Asp Gly
145                 150                 155                 160

Leu Leu Asn Ile Glu Glu Ile His Gln Leu Met His Lys Leu Asn Val
                165                 170                 175

Asn Leu Pro Arg Arg Lys Val Arg Gln Met Phe Gln Glu Ala Asp Thr
            180                 185                 190

Asp Glu Asn Gln Gly Thr Leu Thr Phe Glu Glu Phe Cys Val Phe Tyr
        195                 200                 205

Lys Met Met Ser Leu Arg Arg Asp Leu Tyr Leu Leu Leu Ser Tyr
    210                 215                 220

Ser Asp Lys Lys Asp His Leu Thr Val Glu Glu Leu Ala Gln Phe Leu
225                 230                 235                 240
```

-continued

```
Lys Val Glu Gln Lys Met Asn Asn Val Thr Thr Asp Tyr Cys Leu Asp
                245                 250                 255
Ile Ile Lys Lys Phe Glu Val Ser Glu Asn Lys Val Lys Asn Val
            260                 265                 270
Leu Gly Ile Glu Gly Phe Thr Asn Phe Met Arg Ser Pro Ala Cys Asp
            275                 280                 285
Ile Phe Asn Pro Leu His His Glu Val Tyr Gln Asp Met Asp Gln Pro
        290                 295                 300
Leu Cys Asn Tyr Tyr Ile Ala Ser Ser His Asn Thr Tyr Leu Thr Gly
305                 310                 315                 320
Asp Gln Leu Leu Ser Gln Ser Lys Val Asp Met Tyr Ala Arg Val Leu
                325                 330                 335
Gln Glu Gly Cys Arg Cys Val Glu Val Asp Cys Trp Asp Gly Pro Asp
            340                 345                 350
Gly Glu Pro Val Val His His Gly Tyr Thr Leu Thr Ser Lys Ile Leu
        355                 360                 365
Phe Arg Asp Val Val Glu Thr Ile Asn Lys His Ala Phe Val Lys Asn
    370                 375                 380
Glu Phe Pro Val Ile Leu Ser Ile Glu Asn His Cys Ser Ile Gln Gln
385                 390                 395                 400
Gln Arg Lys Ile Ala Gln Tyr Leu Lys Gly Ile Phe Gly Asp Lys Leu
                405                 410                 415
Asp Leu Ser Ser Val Asp Thr Gly Glu Cys Lys Gln Leu Pro Ser Pro
            420                 425                 430
Gln Ser Leu Lys Gly Lys Ile Leu Val Lys Gly Lys Lys Leu Pro Tyr
        435                 440                 445
His Leu Gly Asp Asp Ala Glu Glu Gly Glu Val Ser Asp Glu Asp Ser
    450                 455                 460
Ala Asp Glu Ile Glu Asp Glu Cys Lys Phe Lys Leu His Tyr Ser Asn
465                 470                 475                 480
Gly Thr Thr Glu His Gln Val Glu Ser Phe Ile Arg Lys Lys Leu Glu
                485                 490                 495
Ser Leu Leu Lys Glu Ser Gln Ile Arg Asp Lys Glu Pro Asp Ser
            500                 505                 510
Phe Thr Val Arg Ala Leu Leu Lys Ala Thr His Glu Gly Leu Asn Ala
        515                 520                 525
His Leu Lys Gln Ser Pro Asp Val Lys Glu Ser Gly Lys Lys Ser His
    530                 535                 540
Gly Arg Ser Leu Met Thr Asn Phe Gly Lys His Lys Lys Thr Thr Lys
545                 550                 555                 560
Ser Arg Ser Lys Ser Tyr Ser Thr Asp Glu Glu Asp Thr Gln Gln
                565                 570                 575
Ser Thr Gly Lys Glu Gly Gly Gln Leu Tyr Arg Leu Gly Arg Arg Arg
            580                 585                 590
Lys Thr Met Lys Leu Cys Arg Glu Leu Ser Asp Leu Val Val Tyr Thr
        595                 600                 605
Asn Ser Val Ala Ala Gln Asp Ile Val Asp Gly Thr Thr Gly Asn
    610                 615                 620
Val Leu Ser Phe Ser Glu Thr Arg Ala His Gln Val Val Gln Gln Lys
625                 630                 635                 640
Ser Glu Gln Phe Met Ile Tyr Asn Gln Lys Gln Leu Thr Arg Ile Tyr
                645                 650                 655
Pro Ser Ala Tyr Arg Ile Asp Ser Ser Asn Phe Asn Pro Leu Pro Tyr
            660                 665                 670
```

```
Trp Asn Ala Gly Cys Gln Leu Val Ala Leu Asn Tyr Gln Ser Glu Gly
            675                 680                 685

Arg Met Met Gln Leu Asn Arg Ala Lys Phe Lys Ala Asn Gly Asn Cys
        690                 695                 700

Gly Tyr Val Leu Lys Pro Gln Gln Met Cys Lys Gly Thr Phe Asn Pro
705                 710                 715                 720

Phe Ser Gly Asp Pro Leu Pro Ala Asn Pro Lys Lys Gln Leu Ile Leu
                725                 730                 735

Lys Val Ile Ser Gly Gln Gln Leu Pro Lys Pro Pro Asp Ser Met Phe
            740                 745                 750

Gly Asp Arg Gly Glu Ile Ile Asp Pro Phe Val Glu Val Glu Ile Ile
        755                 760                 765

Gly Leu Pro Val Asp Cys Cys Lys Asp Gln Thr Arg Val Val Asp Asp
770                 775                 780

Asn Gly Phe Asn Pro Val Trp Glu Glu Thr Leu Thr Phe Thr Val His
785                 790                 795                 800

Met Pro Glu Ile Ala Leu Val Arg Phe Leu Val Trp Asp His Asp Pro
                805                 810                 815

Ile Gly Arg Asp Phe Val Gly Gln Arg Thr Val Thr Phe Ser Ser Leu
            820                 825                 830

Val Pro Gly Tyr Arg His Val Tyr Leu Glu Gly Leu Thr Glu Ala Ser
        835                 840                 845

Ile Phe Val His Ile Thr Ile Asn Glu Ile Tyr Gly Lys Trp Ser Pro
850                 855                 860

Leu Ile Leu Asn Pro Ser Tyr Thr Ile Leu His Phe Leu Gly Ala Thr
865                 870                 875                 880

Lys Asn Arg Gln Leu Gln Gly Leu Lys Gly Leu Phe Asn Lys Asn Pro
                885                 890                 895

Arg His Ser Ser Ser Glu Asn Asn Ser His Tyr Val Arg Lys Arg Ser
            900                 905                 910

Ile Gly Asp Arg Ile Leu Arg Arg Thr Ala Ser Ala Pro Ala Lys Gly
        915                 920                 925

Arg Lys Lys Ser Lys Met Gly Phe Gln Glu Met Val Glu Ile Lys Asp
930                 935                 940

Ser Val Ser Glu Ala Thr Arg Asp Gln Asp Gly Val Leu Arg Arg Thr
945                 950                 955                 960

Thr Arg Ser Leu Gln Ala Arg Pro Val Ser Met Pro Val Asp Arg Asn
                965                 970                 975

Leu Leu Gly Ala Leu Ser Leu Pro Val Ser Glu Thr Ala Lys Asp Ile
            980                 985                 990

Glu Gly Lys Glu Asn Ser Leu Val   Gln Ile
        995                    1000

<210> SEQ ID NO 23
<211> LENGTH: 1693
<212> TYPE: PRT
<213> ORGANISM: Homo sapiens

<400> SEQUENCE: 23

Met Ala Asp Leu Glu Val Tyr Lys Asn Leu Ser Pro Glu Lys Val Glu
1               5                   10                  15

Arg Cys Met Ser Val Met Gln Ser Gly Thr Gln Met Ile Lys Leu Lys
            20                  25                  30

Arg Gly Thr Lys Gly Leu Val Arg Leu Phe Tyr Leu Asp Glu His Arg
        35                  40                  45
```

```
Thr Arg Leu Arg Trp Arg Pro Ser Arg Lys Ser Glu Lys Ala Lys Ile
    50                  55                  60

Leu Ile Asp Ser Ile Tyr Lys Val Thr Glu Gly Arg Gln Ser Glu Ile
65                  70                  75                  80

Phe His Arg Gln Ala Glu Gly Asn Phe Asp Pro Ser Cys Cys Phe Thr
                    85                  90                  95

Ile Tyr His Gly Asn His Met Glu Ser Leu Asp Leu Ile Thr Ser Asn
                100                 105                 110

Pro Glu Glu Ala Arg Thr Trp Ile Thr Gly Leu Lys Tyr Leu Met Ala
                115                 120                 125

Gly Ile Ser Asp Glu Asp Ser Leu Ala Lys Arg Gln Arg Thr His Asp
130                 135                 140

Gln Trp Val Lys Gln Thr Phe Glu Glu Ala Asp Lys Asn Gly Asp Gly
145                 150                 155                 160

Leu Leu Asn Ile Glu Glu Ile His Gln Leu Met His Lys Leu Asn Val
                165                 170                 175

Asn Leu Pro Arg Arg Lys Val Arg Gln Met Phe Gln Glu Ala Asp Thr
            180                 185                 190

Asp Glu Asn Gln Gly Thr Leu Thr Phe Glu Glu Phe Cys Val Phe Tyr
            195                 200                 205

Lys Met Met Ser Leu Arg Arg Asp Leu Tyr Leu Leu Leu Leu Ser Tyr
210                 215                 220

Ser Asp Lys Lys Asp His Leu Thr Val Glu Glu Leu Ala Gln Phe Leu
225                 230                 235                 240

Lys Val Glu Gln Lys Met Asn Asn Val Thr Thr Asp Tyr Cys Leu Asp
                245                 250                 255

Ile Ile Lys Lys Phe Glu Val Ser Glu Glu Asn Lys Val Lys Asn Val
            260                 265                 270

Leu Gly Ile Glu Gly Phe Thr Asn Phe Met Arg Ser Pro Ala Cys Asp
            275                 280                 285

Ile Phe Asn Pro Leu His His Glu Val Tyr Gln Asp Met Asp Gln Pro
290                 295                 300

Leu Cys Asn Tyr Tyr Ile Ala Ser Ser His Asn Thr Tyr Leu Thr Gly
305                 310                 315                 320

Asp Gln Leu Leu Ser Gln Ser Lys Val Asp Met Tyr Ala Arg Val Leu
                325                 330                 335

Gln Glu Gly Cys Arg Cys Val Glu Val Asp Cys Trp Asp Gly Pro Asp
                340                 345                 350

Gly Glu Pro Val Val His His Gly Tyr Thr Leu Thr Ser Lys Ile Leu
            355                 360                 365

Phe Arg Asp Val Val Glu Thr Ile Asn Lys His Ala Phe Val Lys Asn
    370                 375                 380

Glu Phe Pro Val Ile Leu Ser Ile Glu Asn His Cys Ser Ile Gln Gln
385                 390                 395                 400

Gln Arg Lys Ile Ala Gln Tyr Leu Lys Gly Ile Phe Gly Asp Lys Leu
                405                 410                 415

Asp Leu Ser Ser Val Asp Thr Gly Glu Cys Lys Gln Leu Pro Ser Pro
            420                 425                 430

Gln Ser Leu Lys Gly Lys Ile Leu Val Lys Gly Lys Lys Leu Pro Tyr
            435                 440                 445

His Leu Gly Asp Asp Ala Glu Glu Gly Glu Val Ser Asp Glu Asp Ser
    450                 455                 460

Ala Asp Glu Ile Glu Asp Glu Cys Lys Phe Lys Leu His Tyr Ser Asn
```

-continued

```
                465                 470                 475                 480
Gly Thr Thr Glu His Gln Val Glu Ser Phe Ile Arg Lys Lys Leu Glu
                    485                 490                 495
Ser Leu Leu Lys Glu Ser Gln Ile Arg Asp Lys Glu Asp Pro Asp Ser
                500                 505                 510
Phe Thr Val Arg Ala Leu Leu Lys Ala Thr His Glu Gly Leu Asn Ala
                515                 520                 525
His Leu Lys Gln Ser Pro Asp Val Lys Glu Ser Gly Lys Ser His
                530                 535                 540
Gly Arg Ser Leu Met Thr Asn Phe Gly Lys His Lys Lys Thr Thr Lys
545                 550                 555                 560
Ser Arg Ser Lys Ser Tyr Ser Thr Asp Asp Glu Glu Asp Thr Gln Gln
                    565                 570                 575
Ser Thr Gly Lys Glu Gly Gly Gln Leu Tyr Arg Leu Gly Arg Arg Arg
                580                 585                 590
Lys Thr Met Lys Leu Cys Arg Glu Leu Ser Asp Leu Val Val Tyr Thr
                595                 600                 605
Asn Ser Val Ala Ala Gln Asp Ile Val Asp Asp Gly Thr Thr Gly Asn
                610                 615                 620
Val Leu Ser Phe Ser Glu Thr Arg Ala His Gln Val Val Gln Gln Lys
625                 630                 635                 640
Ser Glu Gln Phe Met Ile Tyr Asn Gln Lys Gln Leu Thr Arg Ile Tyr
                    645                 650                 655
Pro Ser Ala Tyr Arg Ile Asp Ser Ser Asn Phe Asn Pro Leu Pro Tyr
                660                 665                 670
Trp Asn Ala Gly Cys Gln Leu Val Ala Leu Asn Tyr Gln Ser Glu Gly
                675                 680                 685
Arg Met Met Gln Leu Asn Arg Ala Lys Phe Lys Ala Asn Gly Asn Cys
                690                 695                 700
Gly Tyr Val Leu Lys Pro Gln Gln Met Cys Lys Gly Thr Phe Asn Pro
705                 710                 715                 720
Phe Ser Gly Asp Pro Leu Pro Ala Asn Pro Lys Lys Gln Leu Ile Leu
                    725                 730                 735
Lys Val Ile Ser Gly Gln Gln Leu Pro Lys Pro Pro Asp Ser Met Phe
                740                 745                 750
Gly Asp Arg Gly Glu Ile Ile Asp Pro Phe Val Glu Val Glu Ile Ile
                755                 760                 765
Gly Leu Pro Val Asp Cys Cys Lys Asp Gln Thr Arg Val Val Asp Asp
                770                 775                 780
Asn Gly Phe Asn Pro Val Trp Glu Glu Thr Leu Thr Phe Thr Val His
785                 790                 795                 800
Met Pro Glu Ile Ala Leu Val Arg Phe Leu Val Trp Asp His Asp Pro
                    805                 810                 815
Ile Gly Arg Asp Phe Val Gly Gln Arg Thr Val Thr Phe Ser Ser Leu
                820                 825                 830
Val Pro Gly Tyr Arg His Val Tyr Leu Glu Gly Leu Thr Glu Ala Ser
                835                 840                 845
Ile Phe Val His Ile Thr Ile Asn Glu Ile Tyr Gly Lys Trp Ser Pro
850                 855                 860
Leu Ile Leu Asn Pro Ser Tyr Thr Ile Leu His Phe Leu Gly Ala Thr
865                 870                 875                 880
Lys Asn Arg Gln Leu Gln Gly Leu Lys Gly Leu Phe Asn Lys Asn Pro
                    885                 890                 895
```

```
Arg His Ser Ser Ser Glu Asn Asn Ser His Tyr Val Arg Lys Arg Ser
            900                 905                 910

Ile Gly Asp Arg Ile Leu Arg Arg Thr Ala Ser Ala Pro Ala Lys Gly
            915                 920                 925

Arg Lys Lys Ser Lys Met Gly Phe Gln Glu Met Val Glu Ile Lys Asp
            930                 935                 940

Ser Val Ser Glu Ala Thr Arg Asp Gln Asp Gly Val Leu Arg Arg Thr
945                 950                 955                 960

Thr Arg Ser Leu Gln Ala Arg Pro Val Ser Met Pro Val Asp Arg Asn
            965                 970                 975

Leu Leu Gly Ala Leu Ser Leu Pro Val Ser Glu Thr Ala Lys Asp Ile
            980                 985                 990

Glu Gly Lys Glu Asn Ser Leu Ala Glu Asp Lys Asp Gly Arg Arg Lys
            995                 1000                1005

Gly Lys Ala Ser Ile Lys Asp Pro His Phe Leu Asn Phe Asn Lys
        1010            1015            1020

Lys Leu Ser Ser Ser Ser Ala Leu Leu His Lys Asp Thr Ser
        1025            1030            1035

Gln Gly Asp Thr Ile Val Ser Thr Ala His Met Ser Val Thr Gly
        1040            1045            1050

Glu Gln Leu Gly Met Ser Ser Pro Arg Gly Gly Arg Thr Thr Ser
        1055            1060            1065

Asn Ala Thr Ser Asn Cys Gln Glu Asn Pro Cys Pro Ser Lys Ser
        1070            1075            1080

Leu Ser Pro Lys Gln His Leu Ala Pro Asp Pro Val Val Asn Pro
        1085            1090            1095

Thr Gln Asp Leu His Gly Val Lys Ile Lys Glu Lys Gly Asn Pro
        1100            1105            1110

Glu Asp Phe Val Glu Gly Lys Ser Ile Leu Ser Gly Ser Val Leu
        1115            1120            1125

Ser His Ser Asn Leu Glu Ile Lys Asn Leu Glu Gly Asn Arg Gly
        1130            1135            1140

Lys Gly Arg Ala Ala Thr Ser Phe Ser Leu Ser Asp Val Ser Met
        1145            1150            1155

Leu Cys Ser Asp Ile Pro Asp Leu His Ser Thr Ala Ile Leu Gln
        1160            1165            1170

Glu Ser Val Ile Ser His Leu Ile Asp Asn Val Thr Leu Thr Asn
        1175            1180            1185

Glu Asn Glu Pro Gly Ser Ser Ile Ser Ala Leu Ile Gly Gln Phe
        1190            1195            1200

Asp Glu Thr Asn Asn Gln Ala Leu Thr Val Val Ser His Leu His
        1205            1210            1215

Asn Thr Ser Val Met Ser Gly His Cys Pro Leu Pro Ser Leu Gly
        1220            1225            1230

Leu Lys Met Pro Ile Lys His Gly Phe Cys Lys Gly Lys Ser Lys
        1235            1240            1245

Ser Ser Phe Leu Cys Ser Ser Pro Glu Leu Ile Ala Leu Ser Ser
        1250            1255            1260

Ser Glu Thr Thr Lys His Ala Thr Asn Thr Val Tyr Glu Thr Thr
        1265            1270            1275

Cys Thr Pro Ile Ser Lys Thr Lys Pro Asp Asp Leu Ser Ser
        1280            1285            1290

Lys Ala Lys Thr Ala Ala Leu Glu Ser Asn Leu Pro Gly Ser Pro
        1295            1300            1305
```

```
Asn Thr Ser Arg Gly Trp Leu Pro Lys Ser Pro Thr Lys Gly Glu
    1310                1315                1320

Asp Trp Glu Thr Leu Lys Ser Cys Ser Pro Ala Ser Ser Pro Asp
    1325                1330                1335

Leu Thr Leu Glu Asp Val Ile Ala Asp Pro Thr Leu Cys Phe Asn
    1340                1345                1350

Ser Gly Glu Ser Ser Leu Val Glu Ile Asp Gly Glu Ser Glu Asn
    1355                1360                1365

Leu Ser Leu Thr Thr Cys Glu Tyr Arg Arg Glu Gly Thr Ser Gln
    1370                1375                1380

Leu Ala Ser Pro Leu Lys Leu Lys Tyr Asn Gln Gly Val Val Glu
    1385                1390                1395

His Phe Gln Arg Gly Leu Arg Asn Gly Tyr Cys Lys Glu Thr Leu
    1400                1405                1410

Arg Pro Ser Val Pro Glu Ile Phe Asn Asn Ile Gln Asp Val Lys
    1415                1420                1425

Thr Gln Ser Ile Ser Tyr Leu Ala Tyr Gln Gly Ala Gly Phe Val
    1430                1435                1440

His Asn His Phe Ser Asp Ser Asp Ala Lys Met Phe Gln Thr Cys
    1445                1450                1455

Val Pro Gln Gln Ser Ser Ala Gln Asp Met His Val Pro Val Pro
    1460                1465                1470

Lys Gln Leu Ala His Leu Pro Leu Pro Ala Leu Lys Leu Pro Ser
    1475                1480                1485

Pro Cys Lys Ser Lys Ser Leu Gly Asp Leu Thr Ser Glu Asp Ile
    1490                1495                1500

Ala Cys Asn Phe Glu Ser Lys Tyr Gln Cys Ile Ser Lys Ser Phe
    1505                1510                1515

Val Thr Thr Gly Ile Arg Asp Lys Lys Gly Val Thr Val Lys Thr
    1520                1525                1530

Lys Ser Leu Glu Pro Ile Asp Ala Leu Thr Glu Gln Leu Arg Lys
    1535                1540                1545

Leu Val Ser Phe Asp Gln Glu Asp Asn Cys Gln Val Leu Tyr Ser
    1550                1555                1560

Lys Gln Asp Ala Asn Gln Leu Pro Arg Ala Leu Val Arg Lys Leu
    1565                1570                1575

Ser Ser Arg Ser Gln Ser Arg Val Arg Asn Ile Ala Ser Arg Ala
    1580                1585                1590

Lys Glu Lys Gln Glu Ala Asn Lys Gln Lys Val Pro Asn Pro Ser
    1595                1600                1605

Asn Gly Ala Gly Val Val Leu Arg Asn Lys Pro Ser Ala Pro Thr
    1610                1615                1620

Pro Ala Val Asn Arg His Ser Thr Gly Ser Tyr Ile Ala Gly Tyr
    1625                1630                1635

Leu Lys Asn Thr Lys Gly Gly Gly Leu Glu Gly Arg Gly Ile Pro
    1640                1645                1650

Glu Gly Ala Cys Thr Ala Leu His Tyr Gly His Val Asp Gln Phe
    1655                1660                1665

Cys Ser Asp Asn Ser Val Leu Gln Thr Glu Pro Ser Ser Asp Asp
    1670                1675                1680

Lys Pro Glu Ile Tyr Phe Leu Leu Arg Leu
    1685                1690
```

<210> SEQ ID NO 24
<211> LENGTH: 608
<212> TYPE: PRT
<213> ORGANISM: Homo sapiens

<400> SEQUENCE: 24

```
Met Glu Met Arg Trp Phe Leu Ser Lys Ile Gln Asp Asp Phe Arg Gly
1               5                   10                  15

Gly Lys Ile Asn Leu Glu Lys Thr Gln Arg Leu Leu Glu Lys Leu Asp
            20                  25                  30

Ile Arg Cys Ser Tyr Ile His Val Lys Gln Ile Phe Lys Asp Asn Asp
        35                  40                  45

Arg Leu Lys Gln Gly Arg Ile Thr Ile Glu Glu Phe Arg Ala Ile Tyr
    50                  55                  60

Arg Ile Ile Thr His Arg Glu Glu Ile Glu Ile Phe Asn Thr Tyr
65                  70                  75                  80

Ser Glu Asn Arg Lys Ile Leu Leu Ala Ser Asn Leu Ala Gln Phe Leu
                85                  90                  95

Thr Gln Glu Gln Tyr Ala Ala Glu Met Ser Lys Ala Ile Ala Phe Glu
            100                 105                 110

Ile Ile Gln Lys Tyr Glu Pro Ile Glu Glu Val Arg Lys Ala His Gln
        115                 120                 125

Met Ser Leu Glu Gly Phe Thr Arg Tyr Met Asp Ser Arg Glu Cys Leu
    130                 135                 140

Leu Phe Lys Asn Glu Cys Arg Lys Val Tyr Gln Asp Met Thr His Pro
145                 150                 155                 160

Leu Asn Asp Tyr Phe Ile Ser Ser His Asn Thr Tyr Leu Val Ser
                165                 170                 175

Asp Gln Leu Leu Gly Pro Ser Asp Leu Trp Gly Tyr Val Ser Ala Leu
            180                 185                 190

Val Lys Gly Cys Arg Cys Leu Glu Ile Asp Cys Trp Asp Gly Ala Gln
        195                 200                 205

Asn Glu Pro Val Val Tyr His Gly Tyr Thr Leu Thr Ser Lys Leu Leu
    210                 215                 220

Phe Lys Thr Val Ile Gln Ala Ile His Lys Tyr Ala Phe Met Thr Ser
225                 230                 235                 240

Asp Tyr Pro Val Val Leu Ser Leu Glu Asn His Cys Ser Thr Ala Gln
                245                 250                 255

Gln Glu Val Met Ala Asp Asn Leu Gln Ala Thr Phe Gly Glu Ser Leu
            260                 265                 270

Leu Ser Asp Met Leu Asp Asp Phe Pro Asp Thr Leu Pro Ser Pro Glu
        275                 280                 285

Ala Leu Lys Phe Lys Ile Leu Val Lys Asn Lys Lys Ile Gly Thr Leu
    290                 295                 300

Lys Glu Thr His Glu Arg Lys Gly Ser Asp Lys Arg Gly Asp Asn Gln
305                 310                 315                 320

Asp Lys Glu Thr Gly Val Lys Lys Leu Pro Gly Val Met Leu Phe Lys
                325                 330                 335

Lys Lys Lys Thr Arg Lys Leu Lys Ile Ala Leu Ala Leu Ser Asp Leu
            340                 345                 350

Val Ile Tyr Thr Lys Ala Glu Lys Phe Lys Ser Phe Gln His Ser Arg
        355                 360                 365

Leu Tyr Gln Gln Phe Asn Glu Asn Asn Ser Ile Gly Glu Thr Gln Ala
    370                 375                 380

Arg Lys Leu Ser Lys Leu Arg Val His Glu Phe Ile Phe His Thr Arg
```

```
                385                 390                 395                 400
Lys Phe Ile Thr Arg Ile Tyr Pro Lys Ala Thr Arg Ala Asp Ser Ser
                    405                 410                 415

Asn Phe Asn Pro Gln Glu Phe Trp Asn Ile Gly Cys Gln Met Val Ala
                420                 425                 430

Leu Asn Phe Gln Thr Pro Gly Leu Pro Met Asp Leu Gln Asn Gly Lys
                    435                 440                 445

Phe Leu Asp Asn Gly Gly Ser Gly Tyr Ile Leu Lys Pro His Phe Leu
            450                 455                 460

Arg Glu Ser Lys Ser Tyr Phe Asn Pro Ser Asn Ile Lys Glu Gly Met
465                 470                 475                 480

Pro Ile Thr Leu Thr Ile Arg Leu Ile Ser Gly Ile Gln Leu Pro Leu
                485                 490                 495

Thr His Ser Ser Ser Asn Lys Gly Asp Ser Leu Val Ile Ile Glu Val
                500                 505                 510

Phe Gly Val Pro Asn Asp Gln Met Lys Gln Gln Thr Arg Val Ile Lys
                515                 520                 525

Lys Asn Ala Phe Ser Pro Arg Trp Asn Glu Thr Phe Thr Phe Ile Ile
            530                 535                 540

His Val Pro Glu Leu Ala Leu Ile Arg Phe Val Val Glu Gly Gln Gly
545                 550                 555                 560

Leu Ile Ala Gly Asn Glu Phe Leu Gly Gln Tyr Thr Leu Pro Leu Leu
                    565                 570                 575

Cys Met Asn Lys Gly Tyr Arg Arg Ile Pro Leu Phe Ser Arg Met Gly
                580                 585                 590

Glu Ser Leu Glu Pro Ala Ser Leu Phe Val Tyr Val Trp Tyr Val Arg
            595                 600                 605

<210> SEQ ID NO 25
<211> LENGTH: 127
<212> TYPE: PRT
<213> ORGANISM: Homo sapiens

<400> SEQUENCE: 25

Arg Leu Asn Ile Arg Val Ile Ser Gly Gln Gln Leu Pro Lys Val Asn
1               5                   10                  15

Lys Asn Lys Asn Ser Ile Val Asp Pro Lys Val Thr Val Glu Ile His
                20                  25                  30

Gly Val Ser Arg Asp Val Ala Ser Arg Gln Thr Ala Val Ile Thr Asn
            35                  40                  45

Asn Gly Phe Asn Pro Trp Trp Asp Thr Glu Phe Ala Phe Glu Val Val
        50                  55                  60

Val Pro Asp Leu Ala Leu Ile Arg Phe Leu Val Glu Asp Tyr Asp Ala
65                  70                  75                  80

Ser Ser Lys Asn Asp Phe Ile Gly Gln Ser Thr Ile Pro Leu Asn Ser
                85                  90                  95

Leu Lys Gln Gly Tyr Arg His Val His Leu Met Ser Lys Asn Gly Asp
            100                 105                 110

Gln His Pro Ser Ala Thr Leu Phe Val Lys Ile Ser Leu Gln Asp
        115                 120                 125

<210> SEQ ID NO 26
<211> LENGTH: 129
<212> TYPE: PRT
<213> ORGANISM: Homo sapiens

<400> SEQUENCE: 26
```

```
Thr Leu Ser Ile Gln Val Leu Thr Ala Gln Gln Leu Pro Lys Leu Asn
1               5                   10                  15

Ala Glu Lys Pro His Ser Ile Val Asp Pro Leu Val Arg Ile Glu Ile
                20                  25                  30

His Gly Val Pro Ala Asp Cys Ala Arg Gln Glu Thr Asp Tyr Val Leu
            35                  40                  45

Asn Asn Gly Phe Asn Pro Arg Trp Gly Gln Thr Leu Gln Phe Gln Leu
50                      55                  60

Arg Ala Pro Glu Leu Ala Leu Val Arg Phe Val Glu Asp Tyr Asp
65                  70                  75                  80

Ala Thr Ser Pro Asn Asp Phe Val Gly Gln Phe Thr Leu Pro Leu Ser
                85                  90                  95

Ser Leu Lys Gln Gly Tyr Arg His Ile His Leu Ser Lys Asp Gly
            100                 105                 110

Ala Ser Leu Ser Pro Ala Thr Leu Phe Ile Gln Ile Arg Ile Gln Arg
        115                 120                 125

Ser

<210> SEQ ID NO 27
<211> LENGTH: 135
<212> TYPE: PRT
<213> ORGANISM: Homo sapiens

<400> SEQUENCE: 27

Thr Leu Leu Ile Gln Val Ile Ser Gly Gln Gln Leu Pro Lys Val Asp
1               5                   10                  15

Lys Thr Lys Glu Gly Ser Ile Val Asp Pro Leu Val Lys Val Gln Ile
                20                  25                  30

Phe Gly Val Arg Leu Asp Thr Ala Arg Gln Glu Thr Asn Tyr Val Glu
            35                  40                  45

Asn Asn Gly Phe Asn Pro Tyr Trp Gly Gln Thr Leu Cys Phe Arg Val
50                      55                  60

Leu Val Pro Glu Leu Ala Met Leu Arg Phe Val Met Asp Tyr Asp
65                  70                  75                  80

Trp Lys Ser Arg Asn Asp Phe Ile Gly Gln Tyr Thr Leu Pro Trp Thr
                85                  90                  95

Cys Met Gln Gln Gly Tyr Arg His Ile His Leu Leu Ser Lys Asp Gly
            100                 105                 110

Ile Ser Leu Arg Pro Ala Ser Ile Phe Val Tyr Ile Cys Ile Gln Glu
        115                 120                 125

Gly Leu Glu Gly Asp Glu Ser
130                 135

<210> SEQ ID NO 28
<211> LENGTH: 540
<212> TYPE: PRT
<213> ORGANISM: Homo sapiens

<400> SEQUENCE: 28

Thr Leu Ser Val Lys Ile Ile Ser Gly Gln Phe Leu Ser Asp Lys Lys
1               5                   10                  15

Val Gly Thr Tyr Val Glu Val Asp Met Phe Gly Leu Pro Val Asp Thr
                20                  25                  30

Arg Arg Lys Ala Phe Lys Thr Lys Thr Ser Gln Gly Asn Ala Val Asn
            35                  40                  45

Pro Val Trp Glu Glu Glu Pro Ile Val Phe Lys Lys Val Val Leu Pro
```

-continued

```
                50                  55                  60
Thr Leu Ala Cys Leu Arg Ile Ala Val Tyr Glu Glu Gly Gly Lys Phe
 65                  70                  75                  80

Ile Gly His Arg Ile Leu Pro Val Gln Ala Ile Arg Pro Gly Tyr His
                     85                  90                  95

Tyr Ile Cys Leu Arg Asn Glu Arg Asn Gln Pro Leu Thr Leu Pro Ala
                    100                 105                 110

Val Phe Val Tyr Ile Glu Val Lys Asp Tyr Val Pro Asp Thr Tyr Ala
                    115                 120                 125

Asp Val Ile Glu Ala Leu Ser Asn Pro Ile Arg Tyr Val Asn Leu Met
130                 135                 140

Glu Gln Arg Ala Lys Gln Leu Ala Ala Leu Thr Leu Glu Asp Glu Glu
145                 150                 155                 160

Glu Val Lys Lys Glu Ala Asp Pro Gly Glu Thr Pro Ser Glu Ala Pro
                    165                 170                 175

Ser Glu Ala Arg Thr Thr Pro Ala Glu Asn Gly Val Asn His Thr Thr
                    180                 185                 190

Thr Leu Thr Pro Lys Pro Pro Ser Gln Ala Leu His Ser Gln Pro Ala
                    195                 200                 205

Pro Gly Ser Val Lys Ala Pro Ala Lys Thr Glu Asp Leu Ile Gln Ser
210                 215                 220

Val Leu Thr Glu Val Glu Ala Gln Thr Ile Glu Glu Leu Lys Gln Gln
225                 230                 235                 240

Lys Ser Phe Val Lys Leu Gln Lys Lys His Tyr Lys Glu Met Lys Asp
                    245                 250                 255

Leu Val Lys Arg His His Lys Lys Thr Thr Asp Leu Ile Lys Glu His
                    260                 265                 270

Thr Thr Lys Tyr Asn Glu Ile Gln Asn Asp Tyr Leu Arg Arg Arg Ala
                    275                 280                 285

Ala Leu Glu Lys Ser Ala Lys Asp Ser Lys Lys Ser Glu Pro
290                 295                 300

Ser Ser Pro Asp His Gly Ser Ser Thr Ile Glu Gln Asp Leu Ala Ala
305                 310                 315                 320

Leu Asp Ala Glu Met Thr Gln Lys Leu Ile Asp Leu Lys Asp Lys Gln
                    325                 330                 335

Gln Gln Gln Leu Leu Asn Leu Arg Gln Glu Gln Tyr Tyr Ser Glu Lys
                    340                 345                 350

Tyr Gln Lys Arg Glu His Ile Lys Leu Leu Ile Gln Lys Leu Thr Asp
                    355                 360                 365

Val Ala Glu Glu Cys Gln Asn Asn Gln Leu Lys Lys Leu Lys Glu Ile
370                 375                 380

Cys Glu Lys Glu Lys Lys Glu Leu Lys Lys Lys Met Asp Lys Lys Arg
385                 390                 395                 400

Gln Glu Lys Ile Thr Glu Ala Lys Ser Lys Asp Lys Ser Gln Met Glu
                    405                 410                 415

Glu Glu Lys Thr Glu Met Ile Arg Ser Tyr Ile Gln Glu Val Val Gln
                    420                 425                 430

Tyr Ile Lys Arg Leu Glu Glu Ala Gln Ser Lys Arg Gln Glu Lys Leu
                    435                 440                 445

Val Glu Lys His Lys Glu Ile Arg Gln Gln Ile Leu Asp Glu Lys Pro
                    450                 455                 460

Lys Leu Gln Val Glu Leu Glu Gln Glu Tyr Gln Asp Lys Phe Lys Arg
465                 470                 475                 480
```

```
Leu Pro Leu Glu Ile Leu Glu Phe Val Gln Glu Ala Met Lys Gly Lys
            485                 490                 495

Ile Ser Glu Asp Ser Asn His Gly Ser Ala Pro Leu Ser Leu Ser Ser
        500                 505                 510

Asp Pro Gly Lys Val Asn His Lys Thr Pro Ser Ser Glu Glu Leu Gly
        515                 520                 525

Gly Asp Ile Pro Gly Lys Glu Phe Asp Thr Pro Leu
        530                 535                 540

<210> SEQ ID NO 29
<211> LENGTH: 503
<212> TYPE: PRT
<213> ORGANISM: Homo sapiens

<400> SEQUENCE: 29

Thr Leu Ser Ile Thr Val Ile Ser Gly Gln Phe Leu Ser Glu Arg Ser
1               5                   10                  15

Val Arg Thr Tyr Val Glu Val Glu Leu Phe Gly Leu Pro Gly Asp Pro
            20                  25                  30

Lys Arg Arg Tyr Arg Thr Lys Leu Ser Pro Ser Thr Asn Ser Ile Asn
        35                  40                  45

Pro Val Trp Lys Glu Pro Phe Val Phe Glu Lys Ile Leu Met Pro
    50                  55                  60

Glu Leu Ala Ser Leu Arg Val Ala Val Met Glu Gly Asn Lys Phe
65                  70                  75                  80

Leu Gly His Arg Ile Ile Pro Ile Asn Ala Leu Asn Ser Gly Tyr His
                85                  90                  95

His Leu Cys Leu His Ser Glu Ser Asn Met Pro Leu Thr Met Pro Ala
            100                 105                 110

Leu Phe Ile Phe Leu Glu Met Lys Asp Tyr Ile Pro Gly Ala Trp Ala
        115                 120                 125

Asp Leu Thr Val Ala Leu Ala Asn Pro Ile Lys Phe Phe Ser Ala His
        130                 135                 140

Asp Thr Lys Ser Val Lys Leu Lys Glu Ala Met Gly Gly Leu Pro Glu
145                 150                 155                 160

Lys Pro Phe Pro Leu Ala Ser Pro Val Ala Ser Gln Val Asn Gly Ala
                165                 170                 175

Leu Ala Pro Thr Ser Asn Gly Ser Pro Ala Ala Arg Ala Gly Ala Arg
            180                 185                 190

Glu Glu Ala Met Lys Glu Ala Ala Glu Pro Arg Thr Ala Ser Leu Glu
        195                 200                 205

Glu Leu Arg Glu Leu Lys Gly Val Val Lys Leu Gln Arg Arg His Glu
    210                 215                 220

Lys Glu Leu Arg Glu Leu Glu Arg Arg Gly Ala Arg Arg Trp Glu Glu
225                 230                 235                 240

Leu Leu Gln Arg Gly Ala Ala Gln Leu Ala Glu Leu Gly Pro Pro Gly
                245                 250                 255

Val Gly Gly Val Gly Ala Cys Lys Leu Gly Pro Gly Lys Gly Ser Arg
            260                 265                 270

Lys Lys Arg Ser Leu Pro Arg Glu Glu Ser Ala Gly Ala Ala Pro Gly
        275                 280                 285

Glu Gly Pro Glu Gly Val Asp Gly Arg Val Arg Glu Leu Lys Asp Arg
    290                 295                 300

Leu Glu Leu Glu Leu Leu Arg Gln Gly Glu Glu Gln Tyr Glu Cys Val
305                 310                 315                 320
```

```
Leu Lys Arg Lys Glu Gln His Val Ala Glu Gln Ile Ser Lys Met Met
            325                 330                 335

Glu Leu Ala Arg Glu Lys Gln Ala Ala Glu Leu Lys Ala Leu Lys Glu
        340                 345                 350

Thr Ser Glu Asn Asp Thr Lys Glu Met Lys Lys Lys Leu Glu Thr Lys
        355                 360                 365

Arg Leu Glu Arg Ile Gln Gly Met Thr Lys Val Thr Thr Asp Lys Met
    370                 375                 380

Ala Gln Glu Arg Leu Lys Arg Glu Ile Asn Asn Ser His Ile Gln Glu
385                 390                 395                 400

Val Val Gln Val Ile Lys Gln Met Thr Glu Asn Leu Glu Arg His Gln
                405                 410                 415

Glu Lys Leu Glu Glu Lys Gln Ala Ala Cys Leu Glu Gln Ile Arg Glu
            420                 425                 430

Met Glu Lys Gln Phe Gln Lys Glu Ala Leu Ala Glu Tyr Glu Ala Arg
        435                 440                 445

Met Lys Gly Leu Glu Ala Glu Val Lys Glu Ser Val Arg Ala Cys Leu
    450                 455                 460

Arg Thr Cys Phe Pro Ser Glu Ala Lys Asp Lys Pro Glu Arg Ala Cys
465                 470                 475                 480

Glu Cys Pro Pro Glu Leu Cys Glu Gln Asp Pro Leu Ile Ala Lys Ala
                485                 490                 495

Asp Ala Gln Glu Ser Arg Leu
            500

<210> SEQ ID NO 30
<211> LENGTH: 507
<212> TYPE: PRT
<213> ORGANISM: Homo sapiens

<400> SEQUENCE: 30

Leu Arg Val Lys Val Ile Ser Gly Gln Phe Leu Ser Asp Arg Lys Val
1               5                   10                  15

Gly Ile Tyr Val Glu Val Asp Met Phe Gly Leu Pro Val Asp Thr Arg
            20                  25                  30

Arg Lys Tyr Arg Thr Arg Thr Ser Gln Gly Asn Ser Phe Asn Pro Val
        35                  40                  45

Trp Asp Glu Glu Pro Phe Asp Phe Pro Lys Val Val Leu Pro Thr Leu
    50                  55                  60

Ala Ser Leu Arg Ile Ala Ala Phe Glu Glu Gly Gly Lys Phe Val Gly
65                  70                  75                  80

His Arg Ile Leu Pro Val Ser Ala Ile Arg Ser Gly Tyr His Tyr Val
                85                  90                  95

Cys Leu Arg Asn Glu Ala Asn Gln Pro Leu Cys Leu Pro Ala Leu Leu
            100                 105                 110

Ile Tyr Thr Glu Ala Ser Asp Tyr Ile Pro Asp Asp His Gln Asp Tyr
        115                 120                 125

Ala Glu Ala Leu Ile Asn Pro Ile Lys His Val Ser Leu Met Asp Gln
    130                 135                 140

Arg Ala Arg Gln Leu Ala Ala Leu Ile Gly Glu Ser Glu Ala Gln Ala
145                 150                 155                 160

Gly Gln Glu Thr Cys Gln Asp Thr Gln Ser Gln Leu Gly Ser Gln
                165                 170                 175

Pro Ser Ser Asn Pro Thr Pro Ser Pro Leu Asp Ala Ser Pro Arg Arg
            180                 185                 190
```

```
Pro Pro Gly Pro Thr Thr Ser Pro Ala Ser Thr Ser Leu Ser Ser Pro
        195                 200                 205

Gly Gln Arg Asp Asp Leu Ile Ala Ser Ile Leu Ser Glu Val Ala Pro
    210                 215                 220

Thr Pro Leu Asp Glu Leu Arg Gly His Lys Ala Leu Val Lys Leu Arg
225                 230                 235                 240

Ser Arg Gln Glu Arg Asp Leu Arg Glu Leu Arg Lys Lys His Gln Arg
                245                 250                 255

Lys Ala Val Thr Leu Thr Arg Arg Leu Leu Asp Gly Leu Ala Gln Ala
            260                 265                 270

Gln Ala Glu Gly Arg Cys Arg Leu Arg Pro Gly Ala Leu Gly Gly Ala
        275                 280                 285

Ala Asp Val Glu Asp Thr Lys Glu Gly Glu Asp Glu Ala Lys Arg Tyr
    290                 295                 300

Gln Glu Phe Gln Asn Arg Gln Val Gln Ser Leu Leu Glu Leu Arg Glu
305                 310                 315                 320

Ala Gln Val Asp Ala Glu Ala Gln Arg Arg Leu Glu His Leu Arg Gln
                325                 330                 335

Ala Leu Gln Arg Leu Arg Glu Val Val Leu Asp Ala Asn Thr Thr Gln
            340                 345                 350

Phe Lys Arg Leu Lys Glu Met Asn Glu Arg Glu Lys Lys Glu Leu Gln
        355                 360                 365

Lys Ile Leu Asp Arg Lys Arg His Asn Ser Ile Ser Glu Ala Lys Met
    370                 375                 380

Arg Asp Lys His Lys Lys Glu Ala Glu Leu Thr Glu Ile Asn Arg Arg
385                 390                 395                 400

His Ile Thr Glu Ser Val Asn Ser Ile Arg Arg Leu Glu Glu Ala Gln
                405                 410                 415

Lys Gln Arg His Asp Arg Leu Val Ala Gly Gln Gln Val Leu Gln
            420                 425                 430

Gln Leu Ala Glu Glu Pro Lys Leu Leu Ala Gln Leu Ala Gln Glu
        435                 440                 445

Cys Gln Glu Gln Arg Ala Arg Leu Pro Gln Glu Ile Arg Arg Ser Leu
    450                 455                 460

Leu Gly Glu Met Pro Glu Gly Leu Gly Asp Gly Pro Leu Val Ala Cys
465                 470                 475                 480

Ala Ser Asn Gly His Ala Pro Gly Ser Ser Gly His Leu Ser Gly Ala
                485                 490                 495

Asp Ser Glu Ser Gln Glu Glu Asn Thr Gln Leu
            500                 505

<210> SEQ ID NO 31
<211> LENGTH: 493
<212> TYPE: PRT
<213> ORGANISM: Homo sapiens

<400> SEQUENCE: 31

Thr Cys Ser Val Gln Val Ile Ser Gly Gln Phe Leu Ser Asp Lys Lys
1               5                   10                  15

Ile Gly Thr Tyr Val Glu Val Asp Met Tyr Gly Leu Pro Thr Asp Thr
                20                  25                  30

Ile Arg Lys Glu Phe Arg Thr Arg Met Val Met Asn Asn Gly Leu Asn
            35                  40                  45

Pro Val Tyr Asn Glu Glu Ser Phe Val Phe Arg Lys Val Ile Leu Pro
        50                  55                  60
```

```
Asp Leu Ala Val Leu Arg Ile Ala Val Tyr Asp Asp Asn Asn Lys Leu
 65                  70                  75                  80

Ile Gly Gln Arg Ile Leu Pro Leu Asp Gly Leu Gln Ala Gly Tyr Arg
                 85                  90                  95

His Ile Ser Leu Arg Asn Glu Gly Asn Lys Pro Leu Ser Leu Pro Thr
            100                 105                 110

Ile Phe Cys Asn Ile Val Leu Lys Thr Tyr Val Pro Asp Gly Phe Gly
        115                 120                 125

Asp Ile Val Asp Ala Leu Ser Asp Pro Lys Lys Phe Leu Ser Ile Thr
    130                 135                 140

Glu Lys Arg Ala Asp Gln Met Arg Ala Met Gly Ile Glu Thr Ser Asp
145                 150                 155                 160

Ile Ala Asp Val Pro Ser Asp Thr Ser Lys Asn Asp Lys Lys Gly Lys
                165                 170                 175

Ala Asn Thr Ala Lys Ala Asn Val Thr Pro Gln Ser Ser Glu Leu
            180                 185                 190

Arg Pro Thr Thr Thr Ala Ala Leu Ala Ser Gly Val Glu Ala Lys Lys
        195                 200                 205

Gly Ile Glu Leu Ile Pro Gln Val Arg Ile Glu Asp Leu Lys Gln Met
210                 215                 220

Lys Ala Tyr Leu Lys His Leu Lys Lys Gln Gln Lys Glu Leu Asn Ser
225                 230                 235                 240

Leu Lys Lys Lys His Ala Lys Glu His Ser Thr Met Gln Lys Leu His
                245                 250                 255

Cys Thr Gln Val Asp Lys Ile Val Ala Gln Tyr Asp Lys Glu Lys Ser
            260                 265                 270

Thr His Glu Lys Ile Leu Glu Lys Ala Met Lys Lys Gly Gly Ser
        275                 280                 285

Asn Cys Leu Glu Met Lys Lys Glu Thr Glu Ile Lys Ile Gln Thr Leu
    290                 295                 300

Thr Ser Asp His Lys Ser Lys Val Lys Glu Ile Val Ala Gln His Thr
305                 310                 315                 320

Lys Glu Trp Ser Glu Met Ile Asn Thr His Ser Ala Glu Glu Gln Glu
                325                 330                 335

Ile Arg Asp Leu His Leu Ser Gln Gln Cys Glu Leu Leu Lys Lys Leu
            340                 345                 350

Leu Ile Asn Ala His Glu Gln Gln Thr Gln Gln Leu Lys Leu Ser His
        355                 360                 365

Asp Arg Glu Ser Lys Glu Met Arg Ala His Gln Ala Lys Ile Ser Met
    370                 375                 380

Glu Asn Ser Lys Ala Ile Ser Gln Asp Lys Ser Ile Lys Asn Lys Ala
385                 390                 395                 400

Glu Arg Glu Arg Arg Val Arg Glu Leu Asn Ser Ser Asn Thr Lys Lys
                405                 410                 415

Phe Leu Glu Glu Arg Lys Arg Leu Ala Met Lys Gln Ser Lys Glu Met
            420                 425                 430

Asp Gln Leu Lys Lys Val Gln Leu Glu His Leu Glu Phe Leu Glu Lys
        435                 440                 445

Gln Asn Glu Gln Leu Leu Lys Ser Cys His Ala Val Ser Gln Thr Gln
    450                 455                 460

Gly Glu Gly Asp Ala Ala Asp Gly Glu Ile Gly Ser Arg Asp Gly Pro
465                 470                 475                 480

Gln Thr Ser Asn Ser Ser Met Lys Leu Gln Asn Ala Asn
                485                 490
```

<210> SEQ ID NO 32
<211> LENGTH: 199
<212> TYPE: PRT
<213> ORGANISM: Homo sapiens

<400> SEQUENCE: 32

Ile Glu Val Leu Gly Ala Arg His Leu Pro Lys Asn Gly Arg Gly Ile
1               5                   10                  15
Val Cys Pro Phe Val Glu Ile Glu Val Ala Gly Ala Glu Tyr Asp Ser
                20                  25                  30
Thr Lys Gln Lys Thr Glu Phe Val Val Asp Asn Gly Leu Asn Pro Val
            35                  40                  45
Trp Pro Ala Lys Pro Phe His Phe Gln Ile Ser Asn Pro Glu Phe Ala
    50                  55                  60
Phe Leu Arg Phe Val Val Tyr Glu Glu Asp Met Phe Ser Asp Gln Asn
65                  70                  75                  80
Phe Leu Ala Gln Ala Thr Phe Pro Val Lys Gly Leu Lys Thr Gly Tyr
                85                  90                  95
Arg Ala Val Pro Leu Lys Asn Asn Tyr Ser Glu Asp Leu Glu Leu Ala
            100                 105                 110
Ser Leu Leu Ile Lys Ile Asp Ile Phe Pro Ala Lys Glu Asn Gly Asp
        115                 120                 125
Leu Ser Pro Phe Ser Gly Thr Ser Leu Arg Glu Arg Gly Ser Asp Ala
    130                 135                 140
Ser Gly Gln Leu Phe His Gly Arg Ala Arg Glu Gly Ser Phe Glu Ser
145                 150                 155                 160
Arg Tyr Gln Gln Pro Phe Glu Asp Phe Arg Ile Ser Gln Glu His Leu
                165                 170                 175
Ala Asp His Phe Asp Ser Arg Glu Arg Arg Ala Pro Arg Arg Thr Arg
            180                 185                 190
Val Asn Gly Asp Asn Arg Leu
        195

<210> SEQ ID NO 33
<211> LENGTH: 204
<212> TYPE: PRT
<213> ORGANISM: Homo sapiens

<400> SEQUENCE: 33

Thr Leu Thr Val Lys Val Leu Gly Ala Arg His Leu Pro Lys Leu Gly
1               5                   10                  15
Arg Ser Ile Ala Cys Pro Phe Val Glu Val Glu Ile Cys Gly Ala Glu
                20                  25                  30
Tyr Asp Asn Asn Lys Phe Lys Thr Thr Val Val Asn Asp Asn Gly Leu
            35                  40                  45
Ser Pro Ile Trp Ala Pro Thr Gln Glu Lys Val Thr Phe Glu Ile Tyr
    50                  55                  60
Asp Pro Asn Leu Ala Phe Leu Arg Phe Val Val Tyr Glu Glu Asp Met
65                  70                  75                  80
Phe Ser Asp Pro Asn Phe Leu Ala His Ala Thr Tyr Pro Ile Lys Ala
                85                  90                  95
Val Lys Ser Gly Phe Arg Ser Val Pro Leu Lys Asn Gly Tyr Ser Glu
            100                 105                 110
Asp Ile Glu Leu Ala Ser Leu Leu Val Phe Cys Glu Met Arg Pro Val
        115                 120                 125

-continued

Leu Glu Ser Glu Glu Leu Tyr Ser Ser Cys Arg Gln Leu Arg Arg
130                 135                 140

Arg Gln Glu Glu Leu Asn Asn Gln Leu Phe Leu Tyr Asp Thr His Gln
145                 150                 155                 160

Asn Leu Arg Asn Ala Asn Arg Asp Ala Leu Val Lys Glu Phe Ser Val
            165                 170                 175

Asn Glu Asn Gln Leu Gln Leu Tyr Gln Glu Lys Cys Asn Lys Arg Leu
        180                 185                 190

Arg Glu Lys Arg Val Ser Asn Ser Lys Phe Tyr Ser
        195                 200

<210> SEQ ID NO 34
<211> LENGTH: 269
<212> TYPE: PRT
<213> ORGANISM: Homo sapiens

<400> SEQUENCE: 34

Leu Ile Leu Lys Val Ile Ser Gly Gln Gln Leu Pro Lys Pro Pro Asp
1               5                   10                  15

Ser Met Phe Gly Asp Arg Gly Glu Ile Ile Asp Pro Phe Val Glu Val
            20                  25                  30

Glu Ile Ile Gly Leu Pro Val Asp Cys Cys Lys Asp Gln Thr Arg Val
        35                  40                  45

Val Asp Asp Asn Gly Phe Asn Pro Val Trp Glu Thr Leu Thr Phe
    50                  55                  60

Thr Val His Met Pro Glu Ile Ala Leu Val Arg Phe Leu Val Trp Asp
65                  70                  75                  80

His Asp Pro Ile Gly Arg Asp Phe Val Gly Gln Arg Thr Val Thr Phe
                85                  90                  95

Ser Ser Leu Val Pro Gly Tyr Arg His Val Tyr Leu Glu Gly Leu Thr
            100                 105                 110

Glu Ala Ser Ile Phe Val His Ile Thr Ile Asn Glu Ile Tyr Gly Lys
        115                 120                 125

Trp Ser Pro Leu Ile Leu Asn Pro Ser Tyr Thr Ile Leu His Phe Leu
130                 135                 140

Gly Ala Thr Lys Asn Arg Gln Leu Gln Gly Leu Lys Gly Leu Phe Asn
145                 150                 155                 160

Lys Asn Pro Arg His Ser Ser Ser Glu Asn Asn Ser His Tyr Val Arg
            165                 170                 175

Lys Arg Ser Ile Gly Asp Arg Ile Leu Arg Arg Thr Ala Ser Ala Pro
        180                 185                 190

Ala Lys Gly Arg Lys Ser Lys Met Gly Phe Gln Glu Met Val Glu
        195                 200                 205

Ile Lys Asp Ser Val Ser Glu Ala Thr Arg Asp Gln Asp Gly Val Leu
210                 215                 220

Arg Arg Thr Thr Arg Ser Leu Gln Ala Arg Pro Val Ser Met Pro Val
225                 230                 235                 240

Asp Arg Asn Leu Leu Gly Ala Leu Ser Leu Pro Val Ser Glu Thr Ala
            245                 250                 255

Lys Asp Ile Glu Gly Lys Glu Asn Ser Leu Val Gln Ile
        260                 265

<210> SEQ ID NO 35
<211> LENGTH: 960
<212> TYPE: PRT
<213> ORGANISM: Homo sapiens

<400> SEQUENCE: 35

```
Leu Ile Leu Lys Val Ile Ser Gly Gln Gln Leu Pro Lys Pro Pro Asp
 1               5                  10                  15
Ser Met Phe Gly Asp Arg Gly Glu Ile Ile Asp Pro Phe Val Glu Val
            20                  25                  30
Glu Ile Ile Gly Leu Pro Val Asp Cys Cys Lys Asp Gln Thr Arg Val
        35                  40                  45
Val Asp Asp Asn Gly Phe Asn Pro Val Trp Glu Glu Thr Leu Thr Phe
 50                  55                  60
Thr Val His Met Pro Glu Ile Ala Leu Val Arg Phe Leu Val Trp Asp
 65                  70                  75                  80
His Asp Pro Ile Gly Arg Asp Phe Val Gly Gln Arg Thr Val Thr Phe
                85                  90                  95
Ser Ser Leu Val Pro Gly Tyr Arg His Val Tyr Leu Glu Gly Leu Thr
            100                 105                 110
Glu Ala Ser Ile Phe Val His Ile Thr Ile Asn Glu Ile Tyr Gly Lys
        115                 120                 125
Trp Ser Pro Leu Ile Leu Asn Pro Ser Tyr Thr Ile Leu His Phe Leu
130                 135                 140
Gly Ala Thr Lys Asn Arg Gln Leu Gln Gly Leu Lys Gly Leu Phe Asn
145                 150                 155                 160
Lys Asn Pro Arg His Ser Ser Glu Asn Asn Ser His Tyr Val Arg
                165                 170                 175
Lys Arg Ser Ile Gly Asp Arg Ile Leu Arg Arg Thr Ala Ser Ala Pro
            180                 185                 190
Ala Lys Gly Arg Lys Lys Ser Lys Met Gly Phe Gln Glu Met Val Glu
        195                 200                 205
Ile Lys Asp Ser Val Ser Glu Ala Thr Arg Asp Gln Asp Gly Val Leu
210                 215                 220
Arg Arg Thr Thr Arg Ser Leu Gln Ala Arg Pro Val Ser Met Pro Val
225                 230                 235                 240
Asp Arg Asn Leu Leu Gly Ala Leu Ser Leu Pro Val Ser Glu Thr Ala
                245                 250                 255
Lys Asp Ile Glu Gly Lys Glu Asn Ser Leu Ala Glu Asp Lys Asp Gly
            260                 265                 270
Arg Arg Lys Gly Lys Ala Ser Ile Lys Asp Pro His Phe Leu Asn Phe
        275                 280                 285
Asn Lys Lys Leu Ser Ser Ser Ser Ala Leu Leu His Lys Asp Thr
290                 295                 300
Ser Gln Gly Asp Thr Ile Val Ser Thr Ala His Met Ser Val Thr Gly
305                 310                 315                 320
Glu Gln Leu Gly Met Ser Ser Pro Arg Gly Gly Arg Thr Thr Ser Asn
                325                 330                 335
Ala Thr Ser Asn Cys Gln Glu Asn Pro Cys Pro Ser Lys Ser Leu Ser
            340                 345                 350
Pro Lys Gln His Leu Ala Pro Asp Pro Val Val Asn Pro Thr Gln Asp
        355                 360                 365
Leu His Gly Val Lys Ile Lys Glu Lys Gly Asn Pro Glu Asp Phe Val
370                 375                 380
Glu Gly Lys Ser Ile Leu Ser Gly Ser Val Leu Ser His Ser Asn Leu
385                 390                 395                 400
Glu Ile Lys Asn Leu Glu Gly Asn Arg Gly Lys Gly Arg Ala Ala Thr
                405                 410                 415
```

```
Ser Phe Ser Leu Ser Asp Val Ser Met Leu Cys Ser Asp Ile Pro Asp
            420                 425                 430

Leu His Ser Thr Ala Ile Leu Gln Glu Ser Val Ile Ser His Leu Ile
            435                 440                 445

Asp Asn Val Thr Leu Thr Asn Glu Asn Glu Pro Gly Ser Ser Ile Ser
450                 455                 460

Ala Leu Ile Gly Gln Phe Asp Glu Thr Asn Asn Gln Ala Leu Thr Val
465                 470                 475                 480

Val Ser His Leu His Asn Thr Ser Val Met Ser Gly His Cys Pro Leu
                485                 490                 495

Pro Ser Leu Gly Leu Lys Met Pro Ile Lys His Gly Phe Cys Lys Gly
            500                 505                 510

Lys Ser Lys Ser Ser Phe Leu Cys Ser Ser Pro Glu Leu Ile Ala Leu
            515                 520                 525

Ser Ser Ser Glu Thr Thr Lys His Ala Thr Asn Thr Val Tyr Glu Thr
            530                 535                 540

Thr Cys Thr Pro Ile Ser Lys Thr Lys Pro Asp Asp Leu Ser Ser
545                 550                 555                 560

Lys Ala Lys Thr Ala Ala Leu Glu Ser Asn Leu Pro Gly Ser Pro Asn
                565                 570                 575

Thr Ser Arg Gly Trp Leu Pro Lys Ser Pro Thr Lys Gly Glu Asp Trp
            580                 585                 590

Glu Thr Leu Lys Ser Cys Ser Pro Ala Ser Ser Pro Asp Leu Thr Leu
            595                 600                 605

Glu Asp Val Ile Ala Asp Pro Thr Leu Cys Phe Asn Ser Gly Glu Ser
610                 615                 620

Ser Leu Val Glu Ile Asp Gly Glu Ser Glu Asn Leu Ser Leu Thr Thr
625                 630                 635                 640

Cys Glu Tyr Arg Arg Glu Gly Thr Ser Gln Leu Ala Ser Pro Leu Lys
                645                 650                 655

Leu Lys Tyr Asn Gln Gly Val Val Glu His Phe Gln Arg Gly Leu Arg
            660                 665                 670

Asn Gly Tyr Cys Lys Glu Thr Leu Arg Pro Ser Val Pro Glu Ile Phe
            675                 680                 685

Asn Asn Ile Gln Asp Val Lys Thr Gln Ser Ile Ser Tyr Leu Ala Tyr
690                 695                 700

Gln Gly Ala Gly Phe Val His Asn His Phe Ser Asp Ser Asp Ala Lys
705                 710                 715                 720

Met Phe Gln Thr Cys Val Pro Gln Gln Ser Ser Ala Gln Asp Met His
                725                 730                 735

Val Pro Val Pro Lys Gln Leu Ala His Leu Pro Leu Pro Ala Leu Lys
            740                 745                 750

Leu Pro Ser Pro Cys Lys Ser Lys Ser Leu Gly Asp Leu Thr Ser Glu
            755                 760                 765

Asp Ile Ala Cys Asn Phe Glu Ser Lys Tyr Gln Cys Ile Ser Lys Ser
770                 775                 780

Phe Val Thr Thr Gly Ile Arg Asp Lys Gly Val Thr Val Lys Thr
785                 790                 795                 800

Lys Ser Leu Glu Pro Ile Asp Ala Leu Thr Glu Gln Leu Arg Lys Leu
                805                 810                 815

Val Ser Phe Asp Gln Glu Asp Asn Cys Gln Val Leu Tyr Ser Lys Gln
            820                 825                 830

Asp Ala Asn Gln Leu Pro Arg Ala Leu Val Arg Lys Leu Ser Ser Arg
            835                 840                 845
```

```
Ser Gln Ser Arg Val Arg Asn Ile Ala Ser Arg Ala Lys Glu Lys Gln
    850                 855                 860

Glu Ala Asn Lys Gln Lys Val Pro Asn Pro Ser Asn Gly Ala Gly Val
865                 870                 875                 880

Val Leu Arg Asn Lys Pro Ser Ala Pro Thr Pro Ala Val Asn Arg His
                885                 890                 895

Ser Thr Gly Ser Tyr Ile Ala Gly Tyr Leu Lys Asn Thr Lys Gly Gly
            900                 905                 910

Gly Leu Glu Gly Arg Gly Ile Pro Glu Gly Ala Cys Thr Ala Leu His
        915                 920                 925

Tyr Gly His Val Asp Gln Phe Cys Ser Asp Asn Ser Val Leu Gln Thr
    930                 935                 940

Glu Pro Ser Ser Asp Asp Lys Pro Glu Ile Tyr Phe Leu Leu Arg Leu
945                 950                 955                 960

<210> SEQ ID NO 36
<211> LENGTH: 126
<212> TYPE: PRT
<213> ORGANISM: Homo sapiens

<400> SEQUENCE: 36

Thr Leu Thr Ile Arg Leu Ile Ser Gly Ile Gln Leu Pro Leu Thr His
1               5                   10                  15

Ser Ser Ser Asn Lys Gly Asp Ser Leu Val Ile Ile Glu Val Phe Gly
                20                  25                  30

Val Pro Asn Asp Gln Met Lys Gln Gln Thr Arg Val Ile Lys Lys Asn
            35                  40                  45

Ala Phe Ser Pro Arg Trp Asn Glu Thr Phe Thr Phe Ile Ile His Val
    50                  55                  60

Pro Glu Leu Ala Leu Ile Arg Phe Val Val Glu Gly Gln Gly Leu Ile
65                  70                  75                  80

Ala Gly Asn Glu Phe Leu Gly Gln Tyr Thr Leu Pro Leu Leu Cys Met
                85                  90                  95

Asn Lys Gly Tyr Arg Arg Ile Pro Leu Phe Ser Arg Met Gly Glu Ser
            100                 105                 110

Leu Glu Pro Ala Ser Leu Phe Val Tyr Val Trp Tyr Val Arg
            115                 120                 125

<210> SEQ ID NO 37
<211> LENGTH: 4
<212> TYPE: PRT
<213> ORGANISM: Homo sapiens

<400> SEQUENCE: 37

Asp Glu Val Asp
1
```

PHARMACEUTICAL COMPOSITION FOR ALLEVIATION AND TREATMENT OF ISCHEMIC CONDITIONS AND METHOD FOR DELIVERING THE SAME

CROSS-REFERENCE TO RELATED APPLICATION

This application claims the benefit of U.S. Provisional Patent Application No. 60/832,584, filed Jul. 24, 2006.

REFERENCE TO SEQUENCE LISTING SUBMITTED ON A COMPACT DISC

The content of the following submissions on compact discs are incorporated herein by reference in their entirety: A computer readable form (CRF) of the Sequence Listing (File Name: Sequence Listing ASCII.txt; Size: 160,357 bytes; Date of Creation: Sep. 26, 2008); and two duplicate compact disc copies (labeled as COPY 1 Replacement and COPY 2 Replacement) of the Sequence Listing (File Name: Sequence Listing ASCII.txt; Size: 160,357 bytes; Date of Creation: Sep. 26, 2008).

BACKGROUND OF THE INVENTION

1. Field of the Invention

The present invention relates to a novel pharmaceutical composition for the treatment of ischemia, which contains a conjugate of a molecule of interest, such as a phospholipase polypeptide, and a protein transduction domain (PTD), as well as a method for delivering the same.

2. Background Art

The body is critically dependent on the heart to pump blood. A healthy heart pumps blood throughout the body for the delivery of oxygen and nutrients and the removal of harmful products of metabolism. Ischemia leads to rapid changes in myocardial metabolism and cardiac and cellular injury. The extent of the injury is dependent on the severity of ischemia and the timeliness of appropriate treatment. Continued ischemia can lead to total tissue necrosis in a few hours.

Reperfusion, although generally considered beneficial, causes tissue injury by several mechanisms. Clinically, in open heart surgery, heart transplantation, and reversal of heart disease, protection of the myocardium against injury by ischemia-reperfusion is an issue of utmost clinical interest. Exacerbation of hypoxic injury after restoration of oxygenation (reoxygenation) by reperfusion is an important mechanism of cellular injury in other types of organ transplantation and in hepatic, intestinal, cerebral, renal, and other ischemic syndromes.

Ischemia and simulated ischemic conditions cause an increase in active oxygen species and an overload of calcium ions ($Ca^{2+}$) (Bolli, R., et al., *Physiol. Rev.* 79:609-634 (1999)). Cytosolic calcium accumulation has been proposed as a mediator of pathologic changes that occur during myocardial ischemia (Moraru, I. I., et al., *Biochim. Biophys. Acta* 1268:1-8 (1995)). The increase in intracellular calcium results in the opening of mitochondrial permeability transition pores (mPTPs). The increase in intracellular calcium further enhances the opening of additional mPTPs and also activates a number of cytosolic proteins, such as phospholipases, protein kinases, proteases, and endonucleases (Bolli, R., et al., *Physiol. Rev.* 79:609-634 (1999)). It has been reported that when treatment with mPTP inhibitors cyclosporin A and sanglifehrin A is performed in post-ischemic reperfusion, the recovery of systolic function and the viability of cells increases by about 20% and 62%, respectively (Javadov, S. A., et al., *J. Physiol.* 549:513-524 (2003)).

Phospholipases, such as phospholipase C (PLC), play an important role in the regulation of calcium homeostasis. To date, eleven mammalian PLC isozymes have been identified. These can be divided into four types: PLC-β, PLC-γ, PLC-δ and PLC-ε. PLC δ1 and γ1 are the predominant forms in normal cardiac cells (Hansen, C. A., et al., *J. Mol. Cell. Cardiol.* 27:471-484 (1995); and Schnabel, P., et al., *J. Mol. Cell. Cardiol.* 28:2419-2427 (1996)).

All PLC isozymes contain a C2 domain that is sensitive to $Ca^{2+}$ activation (Hwang, K-C, et al., *J. Steroid Biochem.* 91:131-138 (2004)). Among the PLC isoforms, PLC-δ1 is most sensitive to activation by intracellular $Ca^{2+}$. Id.

PLC hydrolyzes the membrane phospholipid, phosphatidylinositol 4,5-bisphosphate (PIP2) to generate diacylglycerol (DAG) and inositol 1,4,5-triphosphate (IP3) (Hwang, K-C, et al., *J. Steroid Biochem.* 91:131-138 (2004)). DAG and IP3 stimulate the activity of protein kinase C (PKC) and the release of calcium ions from intracellular reservoirs to the cytoplasm. Id. The activation mechanism of PLC is well known through PLC-β which is activated by a G-protein-coupled receptor, receptor tyrosine kinase, and ras pathway, respectively (Rhee, S. G., et al., *Annu. Rev. Biochem.* 70:281-312 (2001)).

Based on recent studies, it was reported that PLC-δ1 present in the mitochondrial membrane of liver cells functions to inhibit the inflow of calcium, when an excess of calcium is present in the cytoplasm (Hwang, K-C, et al., *J. Steroid Biochem.* 91:131-138 (2004)). It was further shown that PLC-δ1 is present in normal myocardial cells in amounts at least 7 times greater than that of the other isozymes, and that, in an ischemic state, the amount of PLC-δ1 decreases both in vitro and in vivo (Hwang, K-C, et al., *Steroid Biochem.* 91:131-138 (2004)). When treated with the calpain inhibitor calpastatin and the caspase inhibitor zVAD-fmk, the degradation of PLC-δ1 was inhibited. Id. In addition, when PLC-δ1 was overexpressed in cardiomyocytes, intracellular $Ca^{2+}$ overload induced by ischemic conditions was dramatically rescued. Id.

These results demonstrate the critical role PLC-δ1 plays in cytosolic calcium homeostasis in normal hearts and its effect on calcium balance after myocardial infarction. Clearly, an effective method of transducing PLC-δ1 into the cytosol and nucleus of living cells to treat or prevent ischemia or ischemic conditions, without deleterious side effects, is needed.

Protein transduction domains (PTDs) have been used for delivery of biologically active molecules (Viehl C. T., et al., *Ann. Surg. Oncol.* 12:517-525 (2005); Noguchi H., et al., *Nat. Med.* 10:305-309 (2004); and Fu A. L., et al., *Neurosci. Lett.* 368:258-62 (2004)). PTDs are low molecular-weight peptides that have been used for the penetration of physiologically active molecules into cells. However, to date no attempts have been made to use PTDs as a way of delivering phospholipase C in vivo.

BRIEF SUMMARY OF THE INVENTION

One object of the invention is to effectively treat ischemic diseases and conditions by delivering a polypeptide in vivo using a protein transduction domain (PTD).

To achieve the above object, the present invention provides a conjugate of a PTD and a phospholipase (PL) polypeptide (PTD-PL). The conjugate can be prepared by fusing a PTD-encoding gene with a phospholipase gene and expressing and isolating the fusion protein in vitro or in vivo using standard cloning techniques and routine methods known to those skilled in the art. The PTD-PL conjugate according to the present invention easily passes through membranes due to the intracellular penetration and delivery effects of PTD, for delivery to cells.

One embodiment of the present invention is the use of a PTD-PL conjugate to treat, decrease, or prevent intracellular calcium overload caused by ischemia or reperfusion.

A further embodiment is the use of a PTD-PL conjugate to reduce the concentration of free calcium ions in a cell.

The invention also encompasses methods of using a PTD-PL conjugate to reduce, treat, prevent or eliminate cardiac injury (e.g., heart failure, and myocardial infarction) caused by hypoxia or ischemia.

The invention further encompasses methods of using a PTD-PL conjugate to prevent and/or treat cardiovascular disease, myocardial hypoxia or ischemic damage.

The invention also encompasses methods of using a PTD-PL conjugate to prevent stroke during heart failure.

An additional embodiment is the use of a PTD-PL conjugate to prevent or reduce ischemia-reperfusion injury in a subject suffering from hypothermia.

Another embodiment is the use of a PTD-PL conjugate to prevent organ or tissue damage during organ or tissue transplantation. A preferred embodiment is the use of PTD-PLC-δ for heart transplantation.

An additional embodiment of the present invention is the use of a PTD-PL conjugate in combination with one or more therapeutic compounds or constructs.

For all of the above embodiments, fusions of PTD with one or more fragments, derivatives or analogues of PL are also contemplated.

This invention enables administration of the PTD-PL conjugate via local administration routes, thereby minimizing or avoiding systemic side effects.

BRIEF DESCRIPTION OF THE DRAWINGS/FIGURES

FIG. 1 shows the purification of PTD-PLC-δ1 using nickel beads. Lane 1 represents a standard molecular weight protein, and lane 2 represents the fusion protein PTD-PLC-δ1. Human PLC-δ1 is 756 aa in length and about 85 kDa.

Figure 2A:
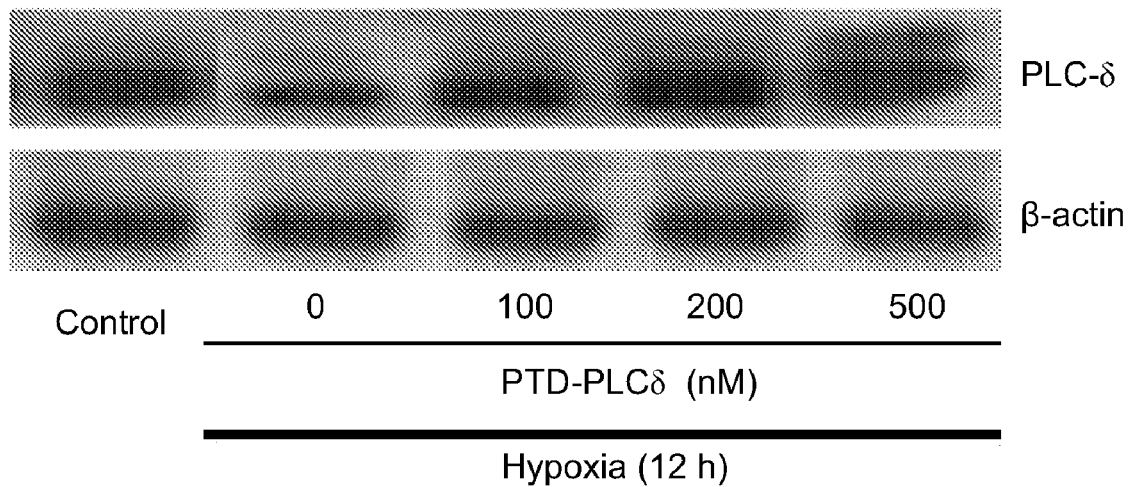
Figure 2B:
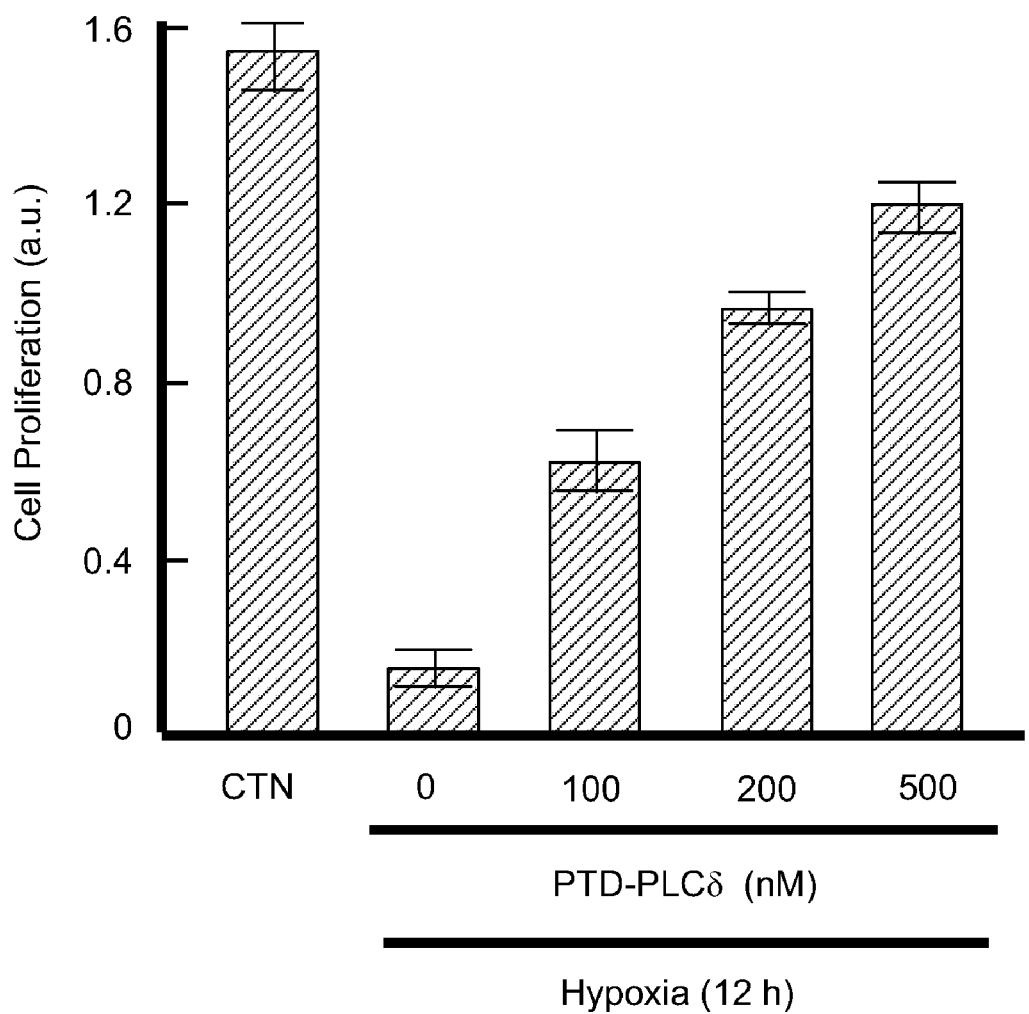

FIGS. 2A and 2B show the penetration of PTD-PLC-δ1 according to the present invention into hypoxia-induced myocardial cells. FIG. 2A shows the amount of PTD-PLC-δ1 protein with a concentration gradient of 0-500 nM in myocardial cells cultured under low-oxygen conditions for 12 hours. FIG. 2B shows cell viability under these conditions. CTL is the control.

Figure 3:
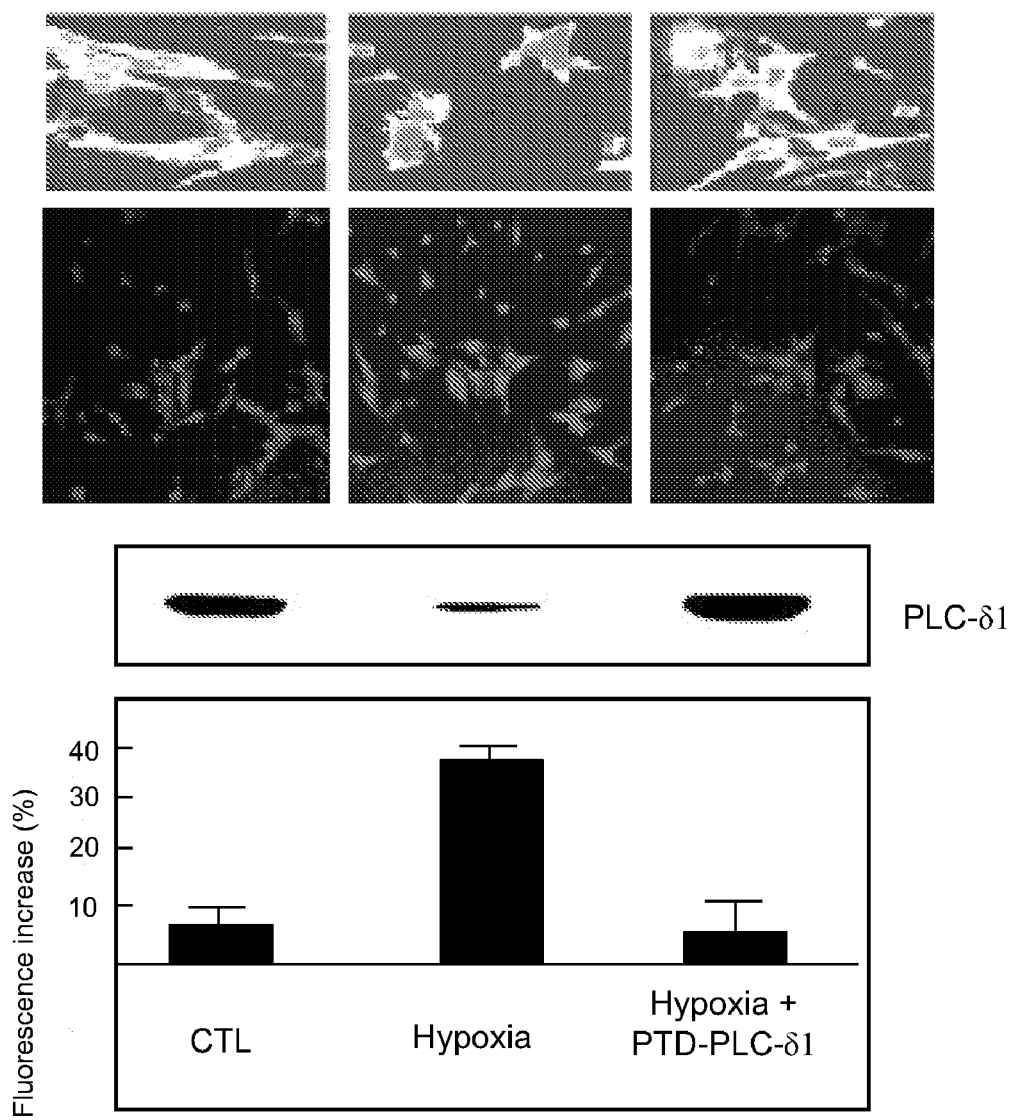

FIG. 3 shows the overload of calcium in myocardial cells cultured under low-oxygen conditions (hypoxia) for 12 hours (lane 2), as compared to a control group incubated under oxygen conditions (lane 1), and when treated with 100 nM of the PTD-PLC-δ1 protein (lane 3). The relative change in intracellular free $Ca^{2+}$ was determined by measuring fluorescent intensity.

Figure 4:
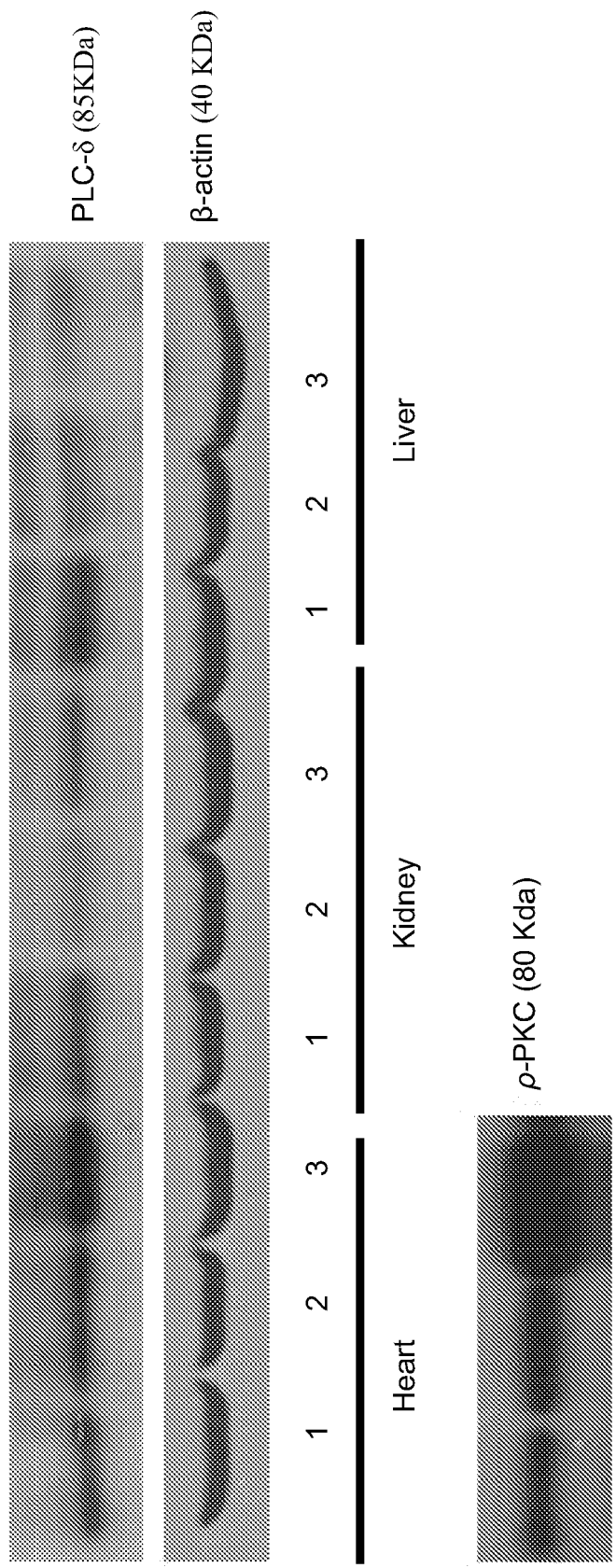

FIG. 4 shows the delivery and penetration of PTD-PLC-δ1 to the internal organs (heart, kidney and liver). In the heart, the phosphorylation of protein kinase C (PKC) is shown. Lane 1: normal; Lane 2: Hypoxia (1 hr) and reperfusion (3 hrs); Lane 3: Hypoxia (1 hr) and reperfusion (3 hrs) plus PTD-PLC-δ1.

Figure 5:
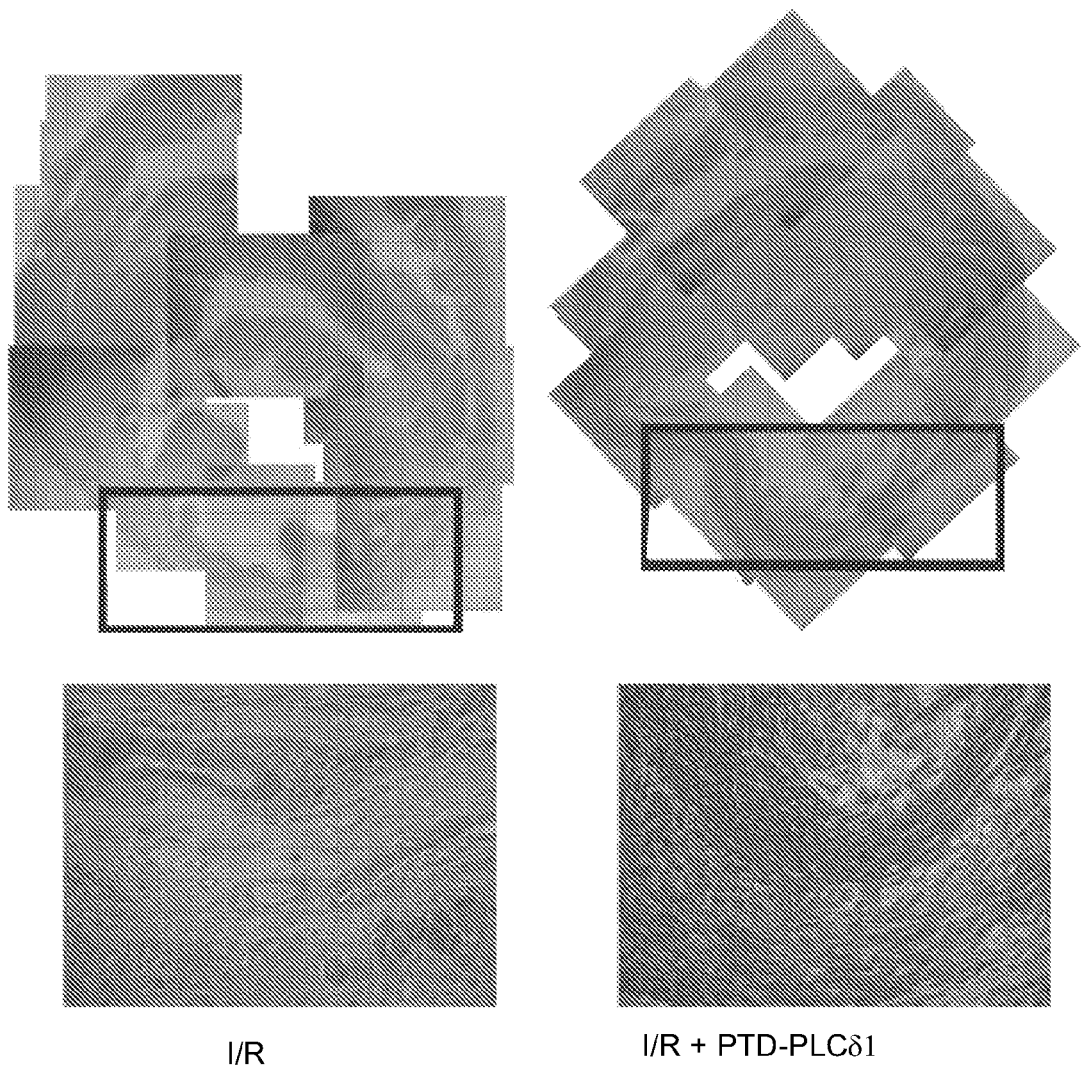

FIG. 5 shows the effect of PTD-PLC-δ1 on the treatment of a cardiac ischemic area in an animal myocardial infarct model. The survival of myocardial cells is visualized in the absence and presence of PTD-PLC-δ1. I/R stands for ischemia followed by reperfusion.

DETAILED DESCRIPTION OF THE INVENTION

Calcium and free radicals act in concert to induce cardiac and neural injury in acute trauma, e.g., ischemia and spinal cord injury. The present invention encompasses methods for treating or preventing ischemia or reperfusion-induced ischemia in cells, such as myocardial cells, with a PTD-PL conjugate.

One of the embodiments of the present invention is the use of a PTD-PL conjugate to treat, decrease, or prevent calcium overload, thereby reducing or inhibiting cardiac, cardiovascular or neural cell death (e.g., myocyte, neuron). Calcium overload may be caused by, e.g., hypoxia, ischemia, reperfusion, cardiovascular (heart) disease or injury, such as a myocardial infarction, or a neurological (brain) disease or injury, such as an ischemic or hemorrhagic stroke. Calcium overload can occur in various body parts or organs, including but not limited to, brain, spinal cord, heart, transplanted organ or transplanted limb, and can be restricted to one of these body parts. A preferred embodiment is the use of a PTD-PLC-δ conjugate to treat, decrease, or prevent calcium overload.

A further embodiment is the use of a PTD-PL conjugate to reduce the concentration of free calcium ions in a cell by administering to a cell an effective amount of PTD-PL.

The invention also relates to methods of treating, preventing or minimizing myocardial oxidative stress, such as is caused by hypoxia or ischemia, in a subject. This is done by administering to a subject in need thereof a therapeutically effective amount of PTC-PL which modulates myocardial oxidative stress such that the myocardial cells which are the target of the oxidative stress are protected from cell death. The cell death may be due, e.g., to necrosis or apoptosis.

A further embodiment of the present invention is the use of a PTD-PLC-δ conjugate to reduce or inhibit cardiovascular or neural cell death. The cardiovascular cell can be, e.g., a cardiac myocyte, ventricular myocyte, atrial myocyte, cardiac stem cell, endothelial cell, vascular smooth muscle cell, pacemaker cell, myofibroblast or fibroblast. The neural cell can be, e.g., a neuron.

The invention also encompasses methods of treating, preventing, reducing or eliminating cardiac or neural injury caused by hypoxia or ischemia in a subject, wherein PTD-PL is administered to a subject in need thereof, such that the hypoxia or ischemic-related injury is treated, prevented, reduced, or eliminated.

The cardiac injury that can be treated, prevented, reduced, or eliminated by the methods and compositions of the present invention includes all cardiac injury caused or affected by hypoxia and/or ischemia. Such injury includes, but is not limited to, cardiac post-ischemic reperfusion, congestive heart failure, myocardial infarction, cardiotoxicity caused by compounds such as drugs (e.g., doxorubicin), cardiac damage due to infection (e.g., syphilis, chronic *Trypanosoma cruzi* infection), fulminant cardiac amyloidosis, heart surgery, heart transplantation, and traumatic cardiac injury (e.g., penetrating or blunt injury, or aortic valve rupture). All or a portion of the heart may be injured, including associated blood vessels and/or tissue, such as the pericardium. Administration of the compounds of the invention may be done where clinically necessary or desirable, e.g., prior to post-ischemic reperfusion, at the onset of post-ischemic reperfusion, or during post-ischemic reperfusion.

The neural injury that can be treated, prevented, reduced, or eliminated by the methods and compositions of the present invention includes all neural injury caused or affected by hypoxia and/or ischemia. Such injury includes, but is not limited to, ischemia-reperfusion injury, neurotoxicity caused by compounds such as drugs, and neural damage due to parasitic infection.

The invention also encompasses methods of using a PTD-PL conjugate to prevent and/or treat cardiovascular disease, myocardial hypoxia or ischemic damage.

The invention further encompasses methods of preventing organ or tissue damage during organ or tissue transplantation, by administering to a donor PTD-PL prior to or concurrent with removal of said organ or tissue, such that damage caused by reperfusion of said organ or tissue is decreased or prevented. Specifically, the invention encompasses a method of preventing ischemia-reperfusion injury in a subject suffering from hypothermia, whereby the subject is pre-treated with a therapeutically effective amount of a fusion polypeptide containing a protein transduction domain (PTD) and a phospholipase polypeptide.

In preferred embodiments, the organ or tissue to be transplanted is the heart or cardiac tissue. The PTD-PL may also be contacted with the organ or tissue following surgical removal of the organ or tissue from the donor. In some embodiments, the PTD-PL is added in addition to known organ or tissue preservation solutions, such as, the University of Wisconsin solution or Celsior solution (see, e.g., Thabut et al., *Am. J. Respir. Crit. Care Med.* 164:1204-8 (2001); Faenza et al., *Transplantation* 72:1274-7 (2001)).

The invention still further encompasses methods of preventing stroke or the onset of stroke in a subject (e.g., a human) suffering from heart failure, by treating a subject with PTC-PL and a pharmaceutically acceptable carrier. The PTC-PL may be administered prior to, or concomitant with, a surgical procedure that may increase the likelihood of a stroke in the patient. In one embodiment, the procedure is balloon angioplasty. Other procedures include coronary artery bypass surgery and valve replacement surgery. The PTC-PL may be administered prior to, concomitant with, or after anti-thrombogenic agents (e.g., coumadin).

The invention includes methods for treating heart failure in a subject by administering PTD-PL alone or in combination with one or more additional therapeutic compounds. In some embodiments, the additional therapeutic compound includes, but is not limited to, an anti-platelet drug, an anti-coagulant drug, and an anti-thrombotic drug, or combinations thereof.

The invention still further encompasses a method of preventing reperfusion injury in a subject (such as a human) suffering from hypothermia, by treating the subject with PTD-PL and a pharmaceutically acceptable carrier. The subject may be treated with PTD-PL prior to or concomitant with the standard rewarming procedures for treating a person suffering from hypothermia as are generally known in the art.

Protein Transduction Domain (PTD)

The PTD effectively allows delivery or uptake of proteins, peptides and chemical compounds of interest in vivo and in vitro into cells by systemic or local administration. Administration routes include routes that are, inter alia, intramuscular, intraperitoneal, intravenous, oral, nasal, subcutaneous, intradermal, mucosal, and inhalation. Thus, if the PTD is provided as a conjugate with a protein, peptide and/or chemical compound, the PTD can deliver the protein, peptide and/or chemical compound to a topical area, e.g., skin, eyeball or airway.

For use as the PTD in the present invention, the present inventors constructed several peptides using a solid synthesis method, but it is to be understood that other kinds of PTD can be used depending on the desired delivery area and the kind of linker used. The PTD consists of 3-30 amino acids, preferably 5-15 amino acids, at least 10-30% of which are preferably arginine residues. However, PTDs without any arginine residues are also contemplated.

One embodiment involves the use of Hph-1-PTD, the PTD from the human (and mouse) transcription factor HPH-1 (YARVRRRGPRR) (SEQ ID NO:1). Another embodiment involves the use of the PTD of Sim-2 (AKAARQAAR) (SEQ ID NO:2).

Other embodiments include, but are not limited to, the PTDs of HIV-1 viral protein Tat (YGRKKRRQRRR) (SEQ ID NO:3), Antennapedia protein (Antp) of *Drosophila* (RQIKIWFQNRRMKWKK) (SEQ ID NO:4), HSV-1 structural protein Vp22 (DAATATRGRSAASRPTERPRAPAR-SAS RPRRPVE) (SEQ ID NO:5), regulator of G protein signaling R7 (RRRRRRR) (SEQ ID NO:6), MTS (membrane translocating sequence), (AAVALLPAVLLALLA-PAAADQNQLMP) (SEQ ID NO:7), and short amphipathic peptide carriers Pep-1 (KETWWETWWTEWSQP-KKKRKV) (SEQ ID NO:8) and Pep-2 (KETWFETW-FTEWSQPKKKRKV) (SEQ ID NO:9).

Phospholipase (PL)

To achieve the above object, the present invention provides a conjugate of a PTD and a polypeptide, such as the enzyme phospholipase, more specifically phospholipase C. There are four main types of PLC enzymes: PLC-β (beta), PLC-γ (gamma), PLC-δ (delta), PLC-ε (eta) and PLC-ζ (zeta). Each PLC type further consists of several subtypes, e.g., β1, β3, β4, δ1, δ3.

One embodiment is the conjugate of a PTD with phospholipase C delta 1 (PLC-δ1). PLC-δ1, when overexpressed in hypoxic cardiomyocytes, rescues intracellular $Ca^{2+}$ overload induced by ischemic conditions.

The nucleotide sequence of PLC-δ1 (SEQ ID NO:10) is:

```
atggactcgg gccgggactt cctgaccctg cacggcctac aggatgatga ggatctacag gcgctgctga agggcagcca gctcctgaag gtgaagtcca gctcatggag gagagagcgc ttctacaagt tgcaggagga ctgcaagacc atctggcagg agtcccgcaa ggtcatgcgg accccggagt cccagctgtt ctccatcgag gacattcagg aggtgcgaat ggggcaccgc acggagggtc tggagaagtt cgcccgtgat gtgcccgagg accgctgctt ctccattgtc ttcaaggacc agcgcaatac actagacctc atcgcccat cgccagctga tgcccagcac tgggtgctgg ggctgcacaa gatcatccac cactcaggct ccatggacca gcgtcagaag ctacagcact ggattcactc ctgcttgcga aaagctgaca aaaacaagga caacaagatg agcttcaagg agctgcagaa cttcctgaag gagctcaaca tccaggtgga cgacagctat gcccggaaga tctttcaggga gtgtgaccac tcccagacag actccctgga ggacgaggag attgaggcct tctacaagat gctgacccag cgggtggaga tcgaccgcac cttcgccgag gccgcgggct caggggagac tctgtcggtg gatcagttag tgacgttcct gcagcaccag cagcgggagg aggcggcagg gcctgcgctg gccctctccc tcattgagcg ctacgagccc agcgagactg ccaaggcgca gcggcagatg accaaggacg gcttcctcat gtacttactg tcggctgacg gcagcgcctt cagcctggca caccgccgtg tctaccagga catgggccag ccacttagcc actacctggt
```

-continued

```
gtcctcttca cacaaacacct acctgctgga ggaccagcta
gccgggccca gcagcactga agcctacatc cgggcactgt
gcaaaggctg ccgatgcctg gagcttgact gctgggacgg
gcccaaccag gaaccaatca tctaccacgg ctatactttc
acttccaaga tcctcttctg cgatgtgctc agggccatcc
gggactatgc cttcaaggcg tcccoctacc ctgtcatcct
atccctggag aaccactgca cactggagca gcagcgcgtg
atggcgcggc acctgcatgc catcctgggc cccatgctgt
tgaaccgacc actggatggg gtcaccaaca gcctgccctc
ccctgagcaa ctgaagggga agatcctgct gaagggggaag
aagctcgggg ggctcctgcc ccctggaggg gagggtggcc
ctgaggccac tgtggtgtca gacgaagacg aggctgctga
gatggaggat gaggcagtga ggagccgtgt gcagcacaag
cccaaggagg acaagctcag gctagcacag gagctctctg
acatggtcat ttactgcaag agtgtccact ttgggggctt
ctccagtcct ggcacccctg gacaggcctt ctacgagatg
gcgtccttct ctgagaaccg tgccottcga ctgctccaag
aatcaggaaa cggctttgtc cgccacaacg tggggcacct
gagcagaatc tacccggctg gatggagaac agactcctcc
aactacagcc ccgtggagat gtggaatggg ggctgccaga
tcgtggccct gaatttccag acacctgggc cagagatgga
cgtgtaccag ggccgcttcc aggacaacgg ggcctgtggg
tacgtgctga gcccgccctt cctgcgagac cccaacggca
cctttaaccc ccgcgccctg gctcaggggc cctggtgggc
acggaagcgg ctcaacatca gggtcatttc ggggcagcag
ctgccaaaag tcaacaagaa taagaattca attgtggacc
ccaaagtgac agtggagatc catggcgtga gccgggacgt
ggccagccgc cagactgctg tcatcaccaa caatggtttc
aacccatggt gggacacgga gtttgcgttt gaggtagttg
tgcctgacct tgccctcatc cgcttcttgg tggaagatta
tgatgcctcc tccaagaatg acttcattgg ccagagtacc
atccccttga acagcctcaa gcaaggatac cgccatgtcc
acctcatgtc taagaacggg gaccagcatc catcagccac
cctctttgtg aagatctccc tccaggacta g.
```

The amino acid sequence of PLC-δ1 (SEQ ID NO:11) is:

MDSGRDFLTLHGLQDDEDLQALLKGSQLLKVKSSSWRRERFYKLQEDCKT
IWQESRKVMRTPESQLFSIEDIQEVRMGHRTEGLEKFARDVPEDRCFSIV
FKDQRNTLDLIAPSPADAQHWVLGLHKIIHHSGSMDQRQKLQHWIHSCLR
KADKNKDNKMSFKELQNFLKELNIQVDDSYARKIFRECDHSQTDSLEDEE
IEAFYKMLTQRVEIDRTFAEAAGSGETLSVDQLVTFLQHQQREEAAGPAL

-continued

ALSLIERYEPSETAKAQRQMTKDGFLMYLLSADGSAFSLAHRRVYQDMGQ
PLSHYLVSSSHNTYLLEDQLAGPSSTEAYIRALCKGCRCLELDCWDGPNQ
EPIIYHGYTFTSKILFCDVLRAIRDYAFKASPYPVILSLENHCTLEQQRV
MARHLHAILGPMLLNRPLDGVTNSLPSPEQLKGKILLKGKKLGGLLPPGG
EGGPEATVVSDEDEAAEMEDEAVRSRVQHKPKEDKLRLAQELSDMVIYCK
SVHFGGFSSPGTPGQAFYEMASFSENRALRLLQESGNGFVRHNVGHLSRI
YPAGWRTDSSNYSPVEMWNGGCQIVALNFQTPGPEMDVYQGRFQDNGACG
YVLKPAFLRDPNGTFNPRALAQGPWWARKRLNIRVISGQQLPKVNKNKNS
IVDPKVTVEIHGVSRDVASRQTAVITNNGFNPWWDTEFAFEVVVPDLALI
RFLVEDYDASSKNDFIGQSTIPLNSLKQGYRHVHLMSKNGDQHPSATLFV
KISLQD.

Another embodiment is the conjugate of a PTD with phospholipase C delta 3 (PLC-δ3). Human PLC-δ3 is 789 amino acids in length.

The nucleotide sequence of PLC-δ3 (SEQ ID NO:12) is:

```
atgctgtgcg gccgctggag gcgttgccgc cgcccgcccg
aggagccccc ggtggccgcc caggtcgcag cccaagtcgc
ggcgccggtc gctctcccgt ccccgccgac tccctccgat
ggcggcacca agaggcccgg gctgcgggcg ctgaagaaga
tgggcctgac ggaggacgag gacgtgcgcg ccatgctgcg
gggctcccgg ctccgcaaga tccgctcgcg cacgtggcac
aaggagcggc tgtaccggct gcaggaggac ggcctgagcg
tgtggttcca gcggcgcatc ccgcgtgcgc catcgcagca
catcttcttc gtgcagcaca tcgaggcggt ccgcgagggc
caccagtccg agggcctgcg gcgcttcggg ggtgccttcg
cgccagcgcg ctgcctcacc atcgccttca agggccgccg
caagaacctg gacctggcg cgcccacggc tgaggaagcg
cagcgctggg tgcgcggtct gaccaagctc cgcgcgcgcc
tggacgccat gagccagcgc gagcggctag accactggat
ccactcctat ctgcaccggg ctgactccaa ccaggacagc
aagatgagct tcaaggagat caagagcctg ctgagaatgg
tcaacgtgga catgaacgac atgtacgcct acctcctctt
caaggagtgt gaccactcca caacgaccg tctagagggg
gctgagatcg aggagttcct gcggcggctg ctgaagcggc
cggagctgga ggagatcttc catcagtact cgggcgagga
ccgcgtgctg agtgcccctg agctgctgga gttcctggag
gaccaggcgc aggagggcgc cacactggcc cgcgcccagc
agctcattca gacctatgag ctcaacgaga cagccaagca
gcatgagctg atgacactgg atggcttcat gatgtacctg
ttgtcgccgg aggggggctgc cttggacaac cccacacgt
```

-continued

```
gtgtgttcca ggacatgaac cagcccttg cccactactt
catctcttcc tcccacaaca cctatctgac tgactccag
atcggggggc ccagcagcac cgaggcctat gttagggcct
ttgcccaggg atgccgctgc gtggagctgg actgctggga
ggggccagga ggggagcccg tcatctatca tggccatacc
ctcacctcca agattctctt ccgggacgtg gtccaagccg
tgcgcgacca tgccttcacg ctgtcccctt accctgtcat
cctatccctg gagaaccact gcgggctgga gcagcaggct
gccatggccc gccacctctg caccatcctg ggggacatgc
tggtgacaca ggcgctggac tccccaaatc ccgaggagct
gccatcccca gagcagctga agggccgggt cctggtgaag
ggaaagaagc tgcccgctgc tcggagcgag gatggccggg
ctctgtcgga tcgggaggag gaggaggagg atgacgagga
ggaagaagag gaggtggagg ctgcagcgca gaggcggctg
gccaagcaga tctccccgga gctgtcggcc ctggctgtgt
actgccacgc caccegcctg cggaccctgc accctgcccc
caacgcccca caaccctgcc aggtcagctc cctcagcgag
cgcaaagcca agaaactcat tcgggaggca gggaacagct
ttgtcaggca caatgccgc cagctgaccc gcgtgtaccc
gctggggctg cggatgaact cagccaacta cagtccccag
gagatgtgga actcgggctg tcagctggtg gccttgaact
tccagacgcc aggctacgag atggacctca atgccgggcg
cttcctagtc aatgggcagt gtggctacgt cctaaaacct
gcctgcctgc ggcaacctga ctcgacctttt gaccccgagt
acccaggacc tcccagaacc actctcagca tccaggtgct
gactgcacag cagctgccca agctgaatgc cgagaagcca
cactccattg tggacccect ggtgcgcatt gagatccatg
gggtgcccgc agactgtgcc cggcaggaga ctgactacgt
gctcaacaat ggcttcaacc ccgctgggg gcagaccctg
cagttccagc tgcgggctcc ggagctggca ctggtccggt
ttgtggtgga agattatgac gccacctccc ccaatgactt
tgtgggccag tttacactgc ctcttagcag cctaaagcaa
gggtaccgcc acatacacct gctttccaag gacggggcct
cactgtcacc agccacgctc ttcatccaaa tccgcatcca
gcgctcctga.
```

The amino acid sequence of PLC-δ3 (SEQ ID NO:13) is:

```
MLCGRWRRCRRPPEEPPVAAQVAAQVAAPVALPSPPTPSDGGTKRPGLRA
LKKMGLTEDEDVRAMLRGSRLRKIRSRTWHKERLYRLQEDGLSVWFQRRI
PRAPSQHIFFVQHIEAVREGHQSEGLRRFGGAFAPARCLTIAFKGRRKNL
DLAAPTAEEAQRWVRGLTKLRARLDAMSQRERLDHWIHSYLHRADSNQDS
```

```
KMSFKEIKSLLRMVNVDMNDMYAYLLFKECDHSNNDRLEGAEIEEFLRRL
LKRPELEEIFHQYSGEDRVLSAPELLEFLEDQGEEGATLARAQQLIQTYE
LNETAKQHELMTLDGFMMYLLSPEGAALDNTHTCVFQDMNQPLAHYFISS
SHNTYLTDSQIGGPSSTEAYVRAFAQGCRCVELDCWEGPGGEPVIYHGHT
LTSKILFRDVVQAVRDHAFTLSPYPVILSLENHCGLEQQAAMARHLCTIL
GDMLVTQALDSPNPEELPSPEQLKGRVLVKGKKLPAARSEDGRALSDREE
EEEDDEEEEEEVEAAAQRRLAKQISPELSALAVYCHATRLRTLHPAPNAP
QPCQVSSLSERKAKKLIREAGNSFVRHNARQLTRVYPLGLRMNSANYSPQ
EMWNSGCQLVALNFQTPGYEMDLNAGRFLVNGQCGYVLKPACLRQPDSTF
DPEYPGPPRTTLSIQVLTAQQLPKLNAEKPHSIVDPLVRIEIHGVPADCA
RQETDYVLNNGFNPRWGQTLQFQLRAPELALVRFVVEDYDATSPNDFVGQ
FTLPLSSLKQGYRHIHLLSKDGASLSPATLFIQIRIQRS.
```

An additional embodiment is the conjugate of a PTD with phospholipase C delta 4 (PLC-δ4). PLC-δ4 is also referred to as PLC-δ2. Human PLC-δ4 is 762 amino acids in length.

The nucleotide sequence of PLC-δ4 (SEQ ID NO:14) is:

```
atggcgtccc tgctgcaaga ccagctgacc actgatcagg
acttgctgct gatgcaggaa ggcatgccga tgcgcaaggt
gaggtccaaa agctggaaga agctaagata cttcagactt
cagaatgacg gcatgacagt ctggcatgca cggcaggcca
ggggcagtgc caagcccagc ttctcaatct ctgatgtgga
gacaatacgt aatggccatg attccgagtt gctgcgtagc
ctggcagagg agctcccct ggagcagggc ttcaccattg
tcttccatgg ccgccgctcc aacctggacc tgatggccaa
cagtgttgag gaggcccaga tatggatgcg agggctccag
ctgttggtgg atcttgtcac cagcatggac catcaggagc
gcctggacca atggctgagc gattggttc aacgtggaga
caaaaatcag gatggtaaga tgagtttcca agaagttcag
cggttattgc acctaatgaa tgtggaaatg gaccaagaat
atgccttcag tcttttttcag gcagcagaca cgtcccagtc
tggaaccctg gaaggagaag aattcgtaca gttctataag
gcattgacta aacgtgctga ggtgcaggaa ctgtttgaaa
gttttcagc tgatgggcag aagctgactc tgctggaatt
tttggatttc ctccaagagg agcagaagga gagagactgc
acctctgagc ttgctctgga actcattgac cgctatgaac
cttcagacag tggcaaactg cggcatgtgc tgagtatgga
tggcttcctc agctacctct gctctaagga tggagacatc
ttcaacccag cctgcctccc catctatcag gatatgactc
aacccctgaa ccactacttc atctgctctt ctcataacac
ctaccctagtg ggggaccagc tttgcggcca gagcagcgtc
```

```
gagggatata tacgggccct gaagcggggg tgccgctgcg
tggaggtgga tgtatgggat ggacctagcg gggaacctgt
cgtttaccac ggacacaccc tgacctcccg catcctgttc
aaagatgtcg tggccacagt agcacagtat gccttccaga
catcagacta cccagtcatc ttgtccctgg agaccactg
cagctgggag cagcagcaga ccatggcccg tcatctgact
gagatcctgg gggagcagct gctgagcacc accttggatg
gggtgctgcc cactcagctg ccctcgcctg aggagcttcg
gaggaagatc ctggtgaagg ggaagaagtt aacacttgag
gaagacctgg aatatgagga gaggaagca gaacctgagt
tggaagagtc agaattggcg ctggagtccc agtttgagac
tgagcctgag ccccaggagc agaaccttca gaataaggac
aaaaagaaga aatccaagcc catcttgtgt ccagccctct
cttccctggt tatctacttg aagtctgtct cattccgcag
cttcacacat tcaaaggagc actaccactt ctacgagata
tcatctttct ctgaaaccaa ggccaagcgc ctcatcaagg
aggctggcaa tgagtttgtg cagcacaata cttggcagtt
aagccgtgtg tatcccagcg gcctgaggac agactcttcc
aactacaacc cccaggaact ctggaatgca ggctgccaga
tggtggccat gaatatgcag actgcagggc ttgaaatgga
catctgtgat gggcatttcc gccagaatgg cggctgtggc
tatgtgctga agcagactt cctgcgtgat atccagagtt
ctttccaccc tgagaagccc atcagccctt tcaaagccca
gactctctta atccaggtga tcagcggtca gcaactcccc
aaagtggaca agaccaaaga gggtccatt gtggatccac
tggtgaaagt gcagatcttt ggcgttcgtc tagacacagc
acggcaggag accaactatg tggagaacaa tggttttaat
ccatactggg ggcagacact atgtttccgg gtgctggtgc
ctgaacttgc catgctgcgt tttgtggtaa tggattatga
ctggaaatcc cgaaatgact ttattggtca gtacaccctg
ccttggacct gcatgcaaca aggttaccgc cacattcacc
tgctgtccaa agatggcatc agcctccgcc cagcttccat
ctttgtgtat atctgcatcc aggaaggcct ggaggggat
gagtcctga.
```

The amino acid sequence of PLC-δ4 (SEQ ID NO:15) is:

```
MASLLQDQLTTDQDLLLMQEGMPMRKVRSKSWKKLRYFRLQNDGMTVWHA
RQARGSAKPSFSISDVETIRNGHDSELLRSLAEELPLEQGFTIVFHGRRS
NLDLMANSVEEAQIWMRGLQLLVDLVTSMDHQERLDQWLSDWFQRGDKNQ
DGKMSFQEVQRLLHLMNVEMDQEYAFSLFQAADTSQSGTLEGEEFVQFYK
ALTKRAEVQELFESFSADGQKLTLLEFLDFLQEEQKERDCTSELALELID
RYEPSDSGKLRHVLSMDGFLSYLCSKDGDIFNPACLPIYQDMTQPLNHYF
ICSSHNTYLVGDQLCGQSSVEGYIRALKRGCRCVEVDVWDGPSGEPVVYH
GHTLTSRILFKDVVATVAQYAFQTSDYPVILSLETHCSWEQQQTMARHLT
EILGEQLLSTTLDGVLPTQLPSPEELRRKILVKGKKLTLEEDLEYEEEEA
EPELEESELALESQFETEPEPQEQNLQNKDKKKKSKPILCPALSSLVIYL
KSVSFRSFTHSKEHYHFYEISSFSETKAKRLIKEAGNEFVQHNTWQLSRV
YPSGLRTDSSNYNPQELWNAGCQMVAMNMQTAGLEMDICDGHFRQNGGCG
YVLKPDFLRDIQSSFHPEKPISPFKAQTLLIQVISGQQLPKVDKTKEGSI
VDPLVKVQIFGVRLDTARQETNYVENNGFNPYWGQTLCFRVLVPELAMLR
FVVMDYDWKSRNDFIGQYTLPWTCMQQGYRHIHLLSKDGISLRPASIFVY
ICIQEGLEGDES.
```

Additional PLC-δ enzymes, including but not limited to, PLC-δ5, are also contemplated as part of the present invention. The nucleotide and amino acid sequence of PLC-δ5 can be found in U.S. Pat. No. 6,958,152, incorporated herein by reference.

Furthermore, additional PLC enzymes, including but not limited to, PLC-PI (beta1), PLC-β2 (beta2), PLC-β3 (beta3), PLC-β4 (beta4), PLC-γ1 (gamma1), PLC-γ2 (gamma2), PLC-ϵ1a (eta1a), PLC-ϵ1ba (eta1b), and PLC-ζ (zeta) are also contemplated as part of the present invention.

The amino acid sequence of PLC-β1 (SEQ ID NO:16) is:

```
MAGAQPGVHALQLKPVCVSDSLKKGTKFVKWDDDSTIVTPIILRTDPQGF
FFYWTDQNKETELLDLSLVKDARCGRHAKAPKDPKLRELLDVGNIGRLEQ
RMITVVYGPDLVNISHLNLVAFQEEVAKEWTNEVFSLATNLLAQNMSRDA
FLEKAYTKLKLQVTPEGRIPLKNIYRLFSADRKRVETALEACSLPSSRND
SIPQEDFTPEVYRVFLNNLCPRPEIDNIFSEFGAKSKPYLTVDQMMDFIN
LKQRDPRLNEILYPPLKQEQVQVLIEKYEPNNSLARKGQISVDGFMRYLS
GEENGVVSPEKLDLNEDMSQPLSHYFINSSHNTYLTAGQLAGNSSVEMYR
QVLLSGCRCVELDCWKGRTAEEEPVITHGFTMTTEISFKIEVIEAIAECA
FKTSPFPILLSFENHVDSPKQQAKMAEYCRLIFGDALLMEPLEKYPLESG
VPLPSPMDLMYKILVKNKKKSHKSSEGSGKKKLSEQASNTYSDSSSMFEP
SSPGAGEADTESDDDDDDDCKKSSMDEGTAGSEAMATEEMSNLVNYIQP
VKFESFEISKKRNKSFEMSSFVETKGLEQLTKSPVEFVEYNKMQLSRIYP
KGTRVDSSNYMPQLFWNAGCQMVALNFQTMDLAMQINMGMYEYNGKSGYR
LKPEFMRRPDKHFDPFTEGIVDGIVANTLSVKIISGQFLSDKKVGTYVEV
DMFGLPVDTRRKAFKTKTSQGNAVNPVWEEEPIVFKKVVLPTLACLRIAV
YEEGGKFIGHRILPVQAIRPGYHYICLRNERNQPLTLPAVFVYIEVKDYV
PDTYADVIEALSNPIRYVNLMEQRAKQLAALTLEDEEEVKKEADPGETPS
EAPSEARTTPAENGVNHTTTLTPKPPSQALHSQPAPGSVKAPAKTEDLIQ
SVLTEVEAQTIEELKQQKSFVKLQKKHYKEMKDLVKRHHKKTTDLIKEHT
TKYNEIQNDYLRRRAALEKSAKKDSKKKSEPSSPDHGSSTIEQDLAALDA
EMTQKLIDLKDKQQQQLLNLRQEQYYSEKYQKREHIKLLIQKLTDVAEEC
```

The amino acid sequence of PLC-β2 (SEQ ID NO:17) is:

MSLLNPVLLPPKVKAYLSQGERFIKWDDETTVASPVILRVDPKGYYLYWT
YQSKEMEFLDITSIRDTRFGKFAKMPKSQKLRDVFNMDFPDNSFLLKTLT
VVSGPDMVDLTFHNFVSYKENVGKAWAEDVLALVKHPLTANASRSTFLDK
ILVKLKMQLNSEGKIPVKNFFQMFPADRKRVEAALSACHLPKGKNDAINP
EDFPEPVYKSFLMSLCPRPEIDEIFTSYHAKAKPYMTKEHLTKFINQKQR
DSRLNSLLFPPARPDQVQGLIDKYEPSGINAQRGQLSPEGMVWFLCGPEN
SVLAQDKLLLHHDMTQPLNHYFINSSHNTYLTAGQFSGLSSAEMYRQVLL
SGCRCVELDCWKGKPPDEEPIITHGFTMTTDIFFKEAIEAIAESAFKTSP
YPIILSFENHVDSPRQQAKMAEYCRTIFGDMLLTEPLEKFPLKPGVPLPS
PEDLRGKILIKNKKNQFSGPTSSSKDTGGEAEGSSPPSAPAVWAGEEGTE
LEEEEVEEEEEESGNLDEEEIKKMQSDEGTAGLEVTAYEEMSSLVNYIQ
PTKFVSFEFSAQKNRSYVISSFTELKAYDLLSKASVQFVDYNKRQMSRIY
PKGTRMDSSNYMPQMFWNAGCQMVALNFQTMDLPMQQNMAVFEFNGQSGY
LLKHEFMRRPDKQFNPFSVDRIDVVVATTLSITVISGQFLSERSVRTYVE
VELFGLPGDPKRRYRTKLSPSTNSINPVWKEEPFVFEKILMPELASLRVA
VMEEGNKFLGHRIIPINALNSGYHHLCLHSESNMPLTMPALFIFLEMKDY
IPGAWADLTVALANPIKFFSAHDTKSVKLKEAMGGLPEKPFPLASPVASQ
VNGALAPTSNGSPAARAGAREEEAMKEAAEPRTASLEELRELKGVVKLQRR
HEKELRELERRGARRWEELLQRGAAQLAELGPPGVGGVGACKLGPGKGSR
KKRSLPREESAGAAPGEGPEGVDGRVRELKDRLELELLRQGEEQYECVLK
RKEQHVAEQISKMMELAREKQAAELKALKETSENDTKEMKKKLETKRLER
IQGMTKVTTDKMAQERLKREINNSHIQEVVQVIKQMTENLERHQEKLEEK
QAACLEQIREMEKQFQKEALAEYEARMKGLEAEVKESVRACLRTCFPSEA
KDKPERACECPPELCEQDPLIAKADAQESRL.

The amino acid sequence of PLC-β3 (SEQ ID NO: 18) is:

MAGAQPGVHALQLEPPTVVETLRRGSKFIKWDEETSSRNLVTLRVDPNGF
FLYWTGPNMEVDTLDISSIRDTRTGRYARLPKDPKIREVLGFGGPDARLE
EKLMTVVSGPDPVNTVFLNFMAVQDDTAKVWSEELFKLAMNILAQNASRN
TFLRKAYTKLKLQVNQDGRIPVKNILKMFSADKKRVETALESCGLKFNRS
ESIRPDEFSLEIFERFLNKLCLRPDIDKILLEIGAKGKPYLTLEQLMDFI
NQKQRDPRLNEVLYPPLRPSQARLLIEKYEPNQQFLERDQMSMEGFSRYL
GGEENGILPLEALDLSTDMTQPLSAYFINSSHNTYLTAGQLAGTSSVEMY
RQALLWGCRCVELDVWKGRPPEEEPFITHGFTMTTEVPLRDVLEAIAETA
FKTSPYPVILSFENHVDSAKQQAKMAEYCRSIFGDALLIEPLDKYPLAPG
VPLPSPQDLMGRILVKNKKRHRPSAGGPDSAGRKRPLEQSNSALSESSAA
TEPSSPQLGSPSSDSCPGLSNGEEVGLEKPSLEPQKSLGDEGLNRGPYVL
GPADREDEEEDEEEEEQTDPKKPTTDEGTASSEVNATEEMSTLVNYIEPV
KFKSFEAARKRNKCFEMSSFVETKAMEQLTKSPMEFVEYNKQQLSRIYPK
GTRVDSSNYMPQLFWNVGCQLVALNFQTLDVAMQLNAGVFEYNGRSGYLL
KPEFMRRPDKSFDPFTEVIVDGIVANALRVKVISGQFLSDRKVGIYVEVD
MFGLPVDTRRKYRTRTSQGNSFNPVWDEEPFDFPKVVLPTLASLRIAAFE
EGGKFVGHRILPVSAIRSGYHYVCLRNEANQPLCLPALLIYTEASDYIPD
DHQDYAEALINPIKHVSLMDQRARQLAALIGESEAQAGQETCQDTQSQQL
GSQPSSNPTPSPLDASPRRPPGPTTSPASTSLSSPGQRDDLIASILSEVA
PTPLDELRGHKALVKLRSRQERDLRELRKKHQRKAVTLTRRLLDGLAQAQ
AEGRCRLRPGALGGAADVEDTKEGEDEAKRYQEFQNRQVQSLLELREAQV
DAEAQRRLEHLRQALQRLREVVLDANTTQFKRLKEMNEREKKELQKILDR
KRHNSISEAKMRDKHKKEAELTEINRRHITESVNSIRRLEEAQKQRHDRL
VAGQQQVLQQLAEEEPKLLAQLAQECQEQRARLPQEIRRSLLGEMPEGLG
DGPLVACASNGHAPGSSGHLSGADSESQEENTQL.

The amino acid sequence of PLC-β4 (SEQ ID NO:19) is:

MAKPYEFNWQKEVPSFLQEGTVFDRYEEESFVFEPNCLFKVDEFGFFLTW
RSEGKEGQVLECSLINSIRSGAIPKDPKILAALEAVGKSENDLEGRIVCV
CSGTDLVNISFTYMVAENPEVTKQWVEGLRSIIHNFRANNVSPMTCLKKH
WMKLAFMTNTNGKIPVRSITRTFASGKTEKVIFQALKELGLPSGKNDEIE
PTAFSYEKFYELTQKICPRTDIEDLFKKINGDKTDYLTVDQLVSFLNEHQ
RDPRLNEILFPFYDAKRAMQIIEMYEPDEDLKKKGLISSDGFCRYLMSDE
NAPVFLDRLELYQEMDHPLAHYFISSSHNTYLTGRQFGGKSSVEMYRQVL
LAGCRCVELDCWDGKGEDQEPIITHGKAMCTDILFKDVIQAIKETAFVTS
EYPVILSFENHCSKYQQYKMSKYCEDLFGDLLLKQALESHPLEPGRALPS
PNDLKLRKILIKNKRLKPEVEKKQLEALRSMMEAGESASPANILEDDNEE
EIESADQEEEAHPEFKFGNELSADDLGHKEAVANSVKKGLVTVEDEQAWM
ASYKYVGATTNIHPYLSTMINYAQPVKFQGFHVAEERNIHYNMSSFNESV
GLGYLKTHAIEFVNYNKRQMSRIYPKGGRVDSSNYMPQIFWNAGCQMVSL
NYQTPDLAMQLNQGKFEYNGSCGYLLKPDFMRRPDRTFDPFSETPVDGVI
AATCSVQVISGQFLSDKKIGTYVEVDMYGLPTDTIRKEFRTRMVMNNGLN
PVYNEESFVFRKVILPDLAVLRIAVYDDNNKLIGQRILPLDGLQAGYRHI
SLRNEGNKPLSLPTIFCNIVLKTYVPDGFGDIVDALSDPKKFLSITEKRA
DQMRAMGIETSDIADVPSDTSKNDKKGKANTAKANVTPQSSSELRPTTTA
ALASGVEAKKGIELIPQVRIEDLKQMKAYLKHLKKQQKELNSLKKKHAKE
HSTMQKLHCTQVDKIVAQYDKEKSTHEKILEKAMKKKGGSNCLEMKKETE
IKIQTLTSDHKSKVKEIVAQHTKEWSEMINTHSAEEQEIRDLHLSQQCEL
LKKLLINAHEQQTQQLKLSHDRESKEMRAHQAKISMENSKAISQDKSIKN
KAERERRVRELNSSNTKKFLEERKRLAMKQSEKEMDQLKKVQLEHLEFLEK

QNEQLLKSCHAVSQTQGEGDAADGEIGSRDGPQTSNSSMKLQNAN

The amino acid sequence of PLC-γ1 (SEQ ID NO:20) is:

MAGAASPCANGCGPGAPSDAEVLHLCRSLEVGTVMTLFYSKKSQRPERKT
FQVKLETRQITWSRGADKIEGAIDIREIKEIRPGKTSRDFDRYQEDPAFR
PDQSHCFVILYGMEFRLKTLSLQATSEDEVNMWIKGLTWLMEDTLQAPTP
LQIERWLRKQFYSVDRNREDRISAKDLKNMLSQVNYRVPNMRFLRERLTD
LEQRSGDITYGQFAQLYRSLMYSAQKTMDLPFLEASTLRAGERPELCRVS
LPEFQQFLLDYQGELWAVDRLQVQEFMLSFLRDPLREIEEPYFFLDEFVT
FLFSKENSVWNSQLDAVCPDTMNNPLSHYWISSSHNTYLTGDQFSSESSL
EAYARCLRMGCRCIELDCWDGPDGMPVIYHGHTLTTKIKFSDVLHTIKEH
AFVASEYPVILSIEDHCSIAQQRNMAQYFKKVLGDTLLTKPVEISADGLP
SPNQLKRKILIKHKKLAEGSAYEEVPTSMMYSENDISNSIKNGILYLEDP
VNHEWYPHYFVLTSSKIYYSEETSSDQGNEDEEEPKEVSSSTELHSNEKW
FHGKLGAGRDGRHIAERLLTEYCIETGAPDGSFLVRESETFVGDYTLSFW
RNGKVQHCRIHSRQDAGTPKFFLTDNLVFDSLYDLITHYQQVPLRCNEFE
MRLSEPVPQTNAHESKEWYHASLTRAQAEHMLRVPRDGAFLVRKRNEPN
SYAISFRAEGKIKHCRVQQEGQTVMLGNSEFDSLVDLISYYEKHPLYRKM
KLRYPINEEALEKIGTAEPDYGALYEGRNPGFYVEANPMPTFKCAVKALF
DYKAQREDELTFIKSAIIQNVEKQEGGWWRGDYGGKKQLWFPSNYVEEMV
NPVALEPEREHLDENSPLGDLLRGVLDVPACQIAIRPEGKNNRLFVFSIS
MASVAHWSLDVAADSQEELQDWVKKIREVAQTADARLTEGKIMERRKKIA
LELSELVVYCRPVPFDEEKIGTERACYRDMSSFPETKAEKYVNKAKGKKF
LQYNRLQLSRIYPKGQRLDSSNYDPLPMWICGSQLVALNFQTPDKPMQMN
QALFMTGRHCGYVLQPSTMRDEAFDPFDKSSLRGLEPCAISIEVLGARHL
PKNGRGIVCPFVEIEVAGAEYDSTKQKTEFVVDNGLNPVWPAKPFHFQIS
NPEFAFLRFVVYEEDMFSDQNFLAQATFPVKGLKTGYRAVPLKNNYSEDL
ELASLLIKIDIFPAKENGDLSPFSGTSLRERGSDASGQLFHGRAREGSFE
SRYQQPFEDFRISQEHLADHFDSRERRAPR RTRVNGDNRL

The amino acid sequence of PLC-γ2 (SEQ ID NO:21) is:

MSTTVNVDSLAEYEKSQIKRALELGTVMTVFSFRKSTPERRTVQVIMETR
QVAWSKTADKIEGFLDIMEIKEIRPGKNSKDFERAKAVRQKEDCCFTILY
GTQFVLSTLSLAADSKEDAVNWLSGLKILHQEAMNASTPTIIESWLRKQI
YSVDQTRRNSISLRELKTILPLINFKVSSAKFLKDKFVEIGAHKDELSFE
QFHLFYKKLMFEQQKSILDEFKKDSSVFILGNTDRPDASAVYLRDFQRFL
IHEQQEHWAQDLNKVRERMTKFIDDTMRETAEPFLFVDEFLTYLFSRENS
IWDEKYDAVDMQDMNNPLSHYWISSSHNTYLTGDQLRSESSPEAYIRCLR
MGCRCIELDCWDGPDGKPVIYHGWTRTTKIKFDDVVQAIKDHAFVTSSFP
VILSIEEHCSVEQQRHMAKAFKEVFGDLLLTKPTEASADQLPSPSQLREK
IIIKHKKLGPRGDVDVNMEDKKDEHKQQGELYMWDSIDQKWTRHYCAIAD
AKLSFSDDIEQTMEEEVPQDIPPTELHFGEKWFHKKVEKRTSAEKLLQEY
CMETGGKDGTFLVRESETFPNDYTLSFWRSGRVQHCRIRSTMEGGTLKYY
LTDNLTFSSIYALIQHYRETHLRCAEFELRLTDPVPNPNPHESKPWYYDS
LSRGEAEDMLMRIPRDGAFLIRKREGSDSYAITFRARGKVKHCRINRDGR
HFVLGTSAYFESLVELVSYYEKHSLYRKMRLRYPVTPELLERYNMERDIN
SLYDVSRMYVDPSEINPSMPQRTVKALYDYKAKRSDELSFCRGALIHNVS
KEPGGWWKGDYGTRIQQYFPSNYVEDISTADFEELEKQIIEDNPLGSLCR
GILDLNTYNVVKAPQGKNQKSFVFILEPKQQGYPPVEFATDRVEELFEWF
QSIREITWKIDTKENNMKYWEKNQSIAIELSDLVVYCKPTSKTKDNLENP
DFREIRSFVETKADSIIRQKPVDLLKYNQKGLTRVYPKGQRVDSSNYDPF
RLWLCGSQMVALNFQTADKYMQMNHALFSLNGRTGYVLQPESMRTEKYDP
MPPESQRKILMTLTVKVLGARHLPKLGRSIACPFVEVEICGAEYDNNKFK
TTVVNDNGLSPIWAPTQEKVTFEIYDPNLAFLRFVVYEEDMFSDPNFLAH
ATYPIKAVKSGFRSVPLKNGYSEDIELASLLVFCEMRPVLESEEELYSSC
RQLRRRQEELNNQLFLYDTHQNLRNANRDALVKEFSVNENQLQLYQEKCN
KRLREKRVSNSKFYS

The amino acid sequence of PLC-ε1a (SEQ ID NO:22) is:

MADLEVYKNLSPEKVERCMSVMQSGTQMIKLKRGTKGLVRLFYLDEHRTR
LRWRPSRKSEKAKILIDSIYKVTEGRQSEIFHRQAEGNFDPSCCFTIYHG
NHMESLDLITSNPEEARTWITGLKYLMAGISDEDSLAKRQRTHDQWVKQT
FEEADKNGDGLLNIEEIHQLMHKLNVNLPRRKVRQMFQEADTDENQGTLT
FEEFCVFYKMMSLRRDLYLLLLSYSDKKDHLTVEELAQFLKVEQKMNNVT
TDYCLDIIKKFEVSEENKVKNVLGIEGFTNFMRSPACDIFNPLHHEVYQD
MDQPLCNYYIASSHNTYLTGDQLLSQSKVDMYARVLQEGCRCVEVDCWDG
PDGEPVVHHGYTLTSKILFRDVVETINKHAFVKNEFPVILSIENHCSIQQ
QRKIAQYLKGIFGDKLDLSSVDTGECKQLPSPQSLKGKILVKGKKLPYHL
GDDAEEGEVSDEDSADEIEDECKFKLHYSNGTTEHQVESFIRKKLESLLK
ESQIRDKEDPDSFTVRALLKATHEGLNAHLKQSPDVKESGKKSHGRSLMT
NFGKHKKTTKSRSKSYSTDDEEDTQQSTGKEGGQLYRLGRRRKTMKLCRE
LSDLVVYTNSVAAQDIVDDGTTGNVLSFSETRAHQVVQQKSEQFMIYNQK
QLTRIYPSAYRIDSSNFNPLPYWNAGCQLVALNYQSEGRMMQLNRAKFKA
NGNCGYVLKPQQMCKGTFNPFSGDPLPANPKKQLILKVISGQQLPKPPDS
MFGDRGEIIDPFVEVEIIGLPVDCCKDQTRVVDDNGFNPVWEETLTFTVH
MPEIALVRFLVWDHDPIGRDFVGQRTVTFSSLVPGYRHVYLEGLTEASIF
VHITINEIYGKWSPLILNPSYTILHFLGATKNRQLQGLKGLFNKNPRHSS
SENNSHYVRKRSIGDRILRRTASAPAKGRKKSKMGFQEMVEIKDSVSEAT
RDQDGVLRRTTRSLQARPVSMPVDRNLLGALSLPVSETAKDIEGKENSLV
QI

The amino acid sequence of PLC-ε1b (SEQ ID NO:23) is:

MADLEVYKNLSPEKVERCMSVMQSGTQMIKLKRGTKGLVRLFYLDEHRTR

LRWRPSRKSEKAKILIDSIYKVTEGRQSEIFHRQAEGNFDPSCCFTIYHG

NHMESLDLITSNPEEARTWITGLKYLMAGISDEDSLAKRQRTHDQWVKQT

FEEADKNGDGLLNIEEIHQLMHKLNVNLPRRKVRQMFQEADTDENQGTLT

FEEFCVFYKMMSLRRDLYLLLLSYSDKKDHLTVEELAQFLKVEQKMNNVT

TDYCLDIIKKFEVSEENKVKNVLGIEGFTNFMRSPACDIFNPLHHEVYQD

MDQPLCNYYIASSHNTYLTGDQLLSQSKVDMYARVLQEGCRCVEVDCWDG

PDGEPVVHHGYTLTSKILFRDVVETINKHAFVKNEFPVILSIENHCSIQQ

QRKIAQYLKGIFGDKLDLSSVDTGECKQLPSPQSLKGKILVKGKKLPYHL

GDDAEEGEVSDEDSADEIEDECKFKLHYSNGTTEHQVESFIRKKLESLLK

ESQIRDKEDPDSFTVRALLKATHEGLNAHLKQSPDVKESGKKSHGRSLMT

NFGKHKKTTKSRSKSYSTDDEEDTQQSTGKEGGQLYRLGRRRKTMKLCRE

LSDLVVYTNSVAAQDIVDDGTTGNVLSFSETRAHQVVQQKSEQFMIYNQK

QLTRIYPSAYRIDSSNFNPLPYWNAGCQLVALNYQSEGRMMQLNRAKFKA

NGNCGYVLKPQQMCKGTFNPFSGDPLPANPKKQLILKVISGQQLPKPPDS

MFGDRGEIIDPFVEVEIIGLPVDCCKDQTRVVDDNGFNPVWEETLTFTVH

MPEIALVRFLVWDHDPIGRDFVGQRTVTFSSLVPGYRHVYLEGLTEASIF

VHITINEIYGKWSPLILNPSYTILHFLGATKNRQLQGLKGLFNKNPRHSS

SENNSHYVRKRSIGDRILRRTASAPAKGRKKSKMGFQEMVEIKDSVSEAT

RDQDGVLRRTTRSLQARPVSMPVDRNLLGALSLPVSETAKDIEGKENSLA

EDKDGRRKGKASIKDPHFLNFNKKLSSSSSALLHKDTSQGDTIVSTAHMS

VTGEQLGMSSPRGGRTTSNATSNCQENPCPSKSLSPKQHLAPDPVVNPTQ

DLHGVKIKEKGNPEDFVEGKSILSGSVLSHSNLEIKNLEGNRGKGRAATS

FSLSDVSMLCSDIPDLHSTAILQESVISHLIDNVTLTNENEPGSSISALI

GQFDETNNQALTVVSHLHNTSVMSGHCPLPSLGLKMPIKHGFCKGKSKSS

FLCSSPELIALSSSETTKHATNTVYETTCTPISKTKPDDDLSSKAKTAAL

ESNLPGSPNTSRGWLPKSPTKGEDWETLKSCSPASSPDLTLEDVIADPTL

CFNSGESSLVEIDGESENLSLTTCEYRREGTSQLASPLKLKYNQGVVEHF

QRGLRNGYCKETLRPSVPEIFNNIQDVKTQSISYLAYQGAGFVHNHFSDS

DAKMFQTCVPQQSSAQDMHVPVPKQLAHLPLPALKLPSPCKSKSLGDLTS

EDIACNFESKYQCISKSFVTTGIRDKKGVTVKTKSLEPIDALTEQLRKLV

SFDQEDNCQVLYSKQDANQLPRALVRKLSSRSQSRVRNIASRAKEKQEAN

KQKVPNPSNGAGVVLRNKPSAPTPAVNRHSTGSYIAGYLKNTKGGGLEGR

GIPEGACTALHYGHVDQFCSDNSVLQTEPSSDDKPEIYFLLRL

The amino acid sequence of PLC-ζ (SEQ ID NO:24) is:

MEMRWFLSKIQDDFRGGKINLEKTQRLLEKLDIRCSYIHVKQIFKDNDRL

KQGRITIEEFRAIYRIITHREEIIEIFNTYSENRKILLASNLAQFLTQEQ

YAAEMSKAIAFEIIQKYEPIEEVRKAHQMSLEGFTRYMDSRECLLFKNEC

RKVYQDMTHPLNDYFISSSHNTYLVSDQLLGPSDLWGYVSALVKGCRCLE

IDCWDGAQNEPVVYHGYTLTSKLLFKTVIQAIHKYAFMTSDYPVVLSLEN

HCSTAQQEVMADNLQATFGESLLSDMLDDFPDTLPSPEALKFKILVKNKK

IGTLKETHERKGSDKRGDNQDKETGVKKLPGVMLFKKKKTRKLKIALALS

DLVIYTKAEKLFKSFQHSRLYQQFNENNSIGETQARKLSKLRVHEFIFHT

RKFITRIYPKATRADSSNFNPQEFWNIGCQMVALNFQTPGLPMDLQNGKF

LDNGGSGYILKPHFLRESKSYFNPSNIKEGMPITLTIRLISGIQLPLTHS

SSNKGDSLVIIEVFGVPNDQMKQQTRVIKKNAFSPRWNETFTFIIHVPEL

ALIRFVVEGQGLIAGNEFLGQYTLPLLCMNKGYRRIIPLFSRMGESLEPA

SLFVYVWYVR

The present invention also provides a conjugate of a PTD and a fragment, derivative or analogue of PL. Specifically, a conjugate of a PTD and a calcium binding domain of PL is contemplated. The calcium binding domain of PL, C2, is sensitive to $Ca^{2+}$ activation. The C2 domains of the PLC enzymes can be found at or near the following amino acids regions: amino acids 630 to 755 of SEQ ID NO:11 (PLC-δ1) (SEQ ID NO:25), amino acids 661 to 787 of SEQ ID NO:13 (PLC-δ3) (SEQ ID NO:26), amino acids 628 to 754 of SEQ ID NO:15 (PLC-δ4) (SEQ ID NO:27), amino acids 677 to 794 of SEQ ID NO:16 (PLC-β1) (SEQ ID NO:28), amino acids 679 to 797 of SEQ ID NO:17 (PLC-β2) (SEQ ID NO:29), amino acids 728 to 843 of SEQ ID NO:18 (PLC-β3) (SEQ ID NO: 30), amino acids 702 to 818 of SEQ ID NO:19 (PLC-β4) (SEQ ID NO:31), amino acids 1092 to 1212 of SEQ ID NO:20 (PLC-γ1) (SEQ ID NO:32), amino acids 1062 to 1187 of SEQ ID NO:21 (PLC-γ2) (SEQ ID NO:33), amino acids 734 to 855 of SEQ ID NO:22 (PLC-ε1a) (SEQ ID NO:34), amino acids 734 to 855 of SEQ ID NO:23 (PLC-ε1b) (SEQ ID NO:35), and amino acids 483 to 606 of SEQ ID NO:24 (PLC-ζ) (SEQ ID NO:36). Additional calcium-binding domains of PL, other than C2, are also contemplated.

The peptide conjugates of the invention can be prepared by fusing a PTD-encoding gene with a PL gene and expressing the fusion protein in vitro or in vivo using standard cloning techniques and routine methods known to those having ordinary skill in the art.

The PTD-PL conjugate can be linked to each other by a direct covalent bond, a peptide bond, or a linker. Particularly, the PTD-PL conjugate can be linked to each other by a linker containing a region that is cleaved specifically by a certain enzyme. In one embodiment, the linker DNA encodes a protease recognition sequence thereby allowing cleavage at the junction of the PTD and the PL. For example, the linker DNA may encode a caspase-3 recognition sequence (e.g., an amino acid sequence comprising DEVD (SEQ ID NO:37)). Linkers without a cleavage site (non-cleavage linkers) may also be used. The length of the linker is typically between 1 and 10 amino acids, preferably between 1 and 5 amino acids. The linker may contain the amino acids Gly, Gly-Gly or Gly-Gly-Gly.

The PTD-PL conjugate according to the present invention easily passes through the cellular membrane into cells due to the intracellular penetration and delivery effects of the PTD.

The use of PTD-PL mRNA for all of the above indications is also contemplated.

A further embodiment involves the use of inhibitors that prevent the degradation of PTD-PL when administered in vivo. In ischemic heart and hypoxic neonatal cardiomyocytes, PLC-δ1 is selectively degraded. Degradation of PLC- δ1 is completely inhibited by the calpain inhibitor, calpastatin, and the caspase inhibitor zVAD-fmk. Thus, an additional embodiment of the present invention is the use of a PTD-calpain- or PTD-caspase-inhibitor to prevent the degradation of PL, thereby rescuing intracellular $Ca^{2+}$ overload induced by ischemic conditions. Such a PTD-inhibitor can be administered alone or in combination with the PTD-PL fusion protein of the present invention and/or other compounds.

DEFINITIONS

For convenience, certain terms used in the specification, examples, and appended claims are collected here. Unless otherwise defined, all technical and scientific terms used herein have the same meaning as commonly understood by one of ordinary skill in the art to which this invention pertains.

As used herein, by the term "hypoxia" is meant insufficient levels of oxygen in blood or tissue (e.g., myocardial infarction). Hypoxia may be the result of a shortage in blood supply caused by, for example, an obstruction of a blood vessel.

As used herein, by the term "ischemia" is meant an inadequate flow or shortage of blood to a part of the body, caused by constriction, obstruction or blockage of the blood vessels supplying it. Ischemia leads to tissue hypoxia. Hypoxia or ischemic-related injury includes cardiac injury.

As used herein, by the term "reperfusion" is meant the restoration of the flow of blood to a previously ischemic tissue or organ that has had its blood supply cut off, as after a heart attack or stroke.

As used herein, by the term "necrosis" is meant the death of cells or tissues through injury or disease, particularly in a localized area of the body such as the myocardium.

As used herein, by the term "apoptosis" is meant programmed cell death.

As used herein, the term "cardiac injury" is intended to encompass any chronic or acute pathological event involving the heart and/or associated tissues (e.g., the pericardium, aorta and other associated blood vessels), including, but not limited to, ischemia-reperfusion injury, congestive heart failure, cardiac arrest, myocardial infarction, cardiotoxicity caused by compounds such as drugs (e.g., doxorubicin, herceptin, thioridazine and cisapride), cardiac damage due to parasitic infection, bacteria, fungi, rickettsiae, or viruses (e.g., syphilis, chronic *Trypanosoma cruzi* infection), fulminant cardiac amyloidosis, heart surgery, heart transplantation, and traumatic cardiac injury (e.g., penetrating or blunt cardiac injury, or aortic valve rupture).

As used herein, the term "neural injury" is intended to encompass any chronic or acute pathological event involving the brain, spinal column, nerves, and/or associated tissues, including, but not limited to, ischemia-reperfusion injury, neurotoxicity caused by compounds such as drugs, and neural damage due to parasitic infection.

As used herein, the term "polypeptide" is intended to encompass a singular "polypeptide" as well as plural "polypeptides," and comprises any chain or chains of two or more amino acids joined together by peptide bonds. Thus, as used herein, terms including, but not limited to "peptide," "dipeptide," "tripeptide," "protein," "amino acid chain," "oligopeptide," "oligomer," or any other term used to refer to a chain or chains of two or more amino acids, are included in the definition of a "polypeptide," and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids. The term "protein" is also intended to include fragments, analogues and derivatives of a protein wherein the fragment, analogue or derivative retains essentially the same biological activity or function as a reference protein.

The "fragment, derivative or analogue" of the protein may be (i) one in which one or more of the amino acid residues are substituted with a conserved or non-conserved amino acid residue (preferably, a conserved amino acid residue) and such substituted amino acid residue may or may not be one encoded by the genetic code; or (ii) one in which one or more of the amino acid residues includes a substituent group; or (iii) one in which the mature polypeptide is fused with another compound, such as a compound to increase the half life of the polypeptide (for example, polyethylene glycol); or (iv) one in which the additional amino acids are fused to the mature polypeptide, such as a leader or secretory sequence which is employed for purification of the polypeptide. Such fragments, derivatives and analogues are deemed to be within the scope of those skilled in the art from the teachings herein.

Particularly preferred are variants, analogues, derivatives and fragments having the amino acid sequence of the protein in which several, e.g., 5 to 10, 1 to 5, 1 to 3, 2, or 1 amino acid residues are substituted, deleted or added in any combination. Especially preferred among these are silent substitutions, additions and deletions, which do not alter the properties and activities of the protein of the present invention. Also especially preferred in this regard are conservative substitutions.

An example of a variant of the present invention is a fusion protein as defined above, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

The terms "fusion protein," "fusion polypeptide," "chimeric protein, and "chimeric polypeptide" as used herein are interchangeable and refer to polypeptides and proteins which comprise a polypeptide or protein of interest and a protein transduction domain (PTD).

The term PTD-PL "conjugate" as used herein refers to both the fusion of a PTD protein with a PL protein, as well as, the fusion of a PTD-encoding gene with a PL gene construct.

The terms "protein of interest", "desired polypeptide", "desired protein" or "target protein" as used herein are interchangeable and refer to a whole protein molecule or a portion thereof. The other portion of the polypeptide or protein is capable of inducing a cellular response.

As used herein, the term "therapeutic agent" refers to a molecule, such as a protein, lipid, carbohydrate, nucleic acid or chemical compound, which when delivered to a subject, treats, i.e., cures, ameliorates, or lessens the symptoms of, a given disease or condition (e.g., ischemia or hypoxia) in that subject, or alternatively, prolongs the life of the subject by slowing the progress of a terminal disease or condition.

As used herein, the term "therapeutic fusion polypeptide" refers to a polypeptide which when delivered to a subject, treats, i.e., cures, ameliorates, or lessens the symptoms of, a given disease or condition (e.g., ischemia or hypoxia) in that subject, or alternatively, prolongs the life of the subject by slowing the progress of a terminal disease or condition.

Polypeptides

The therapeutic polypeptides of the present invention are the phospholipase proteins (PLs), including but not limited to, the phospholipase C (PLC) polypeptides. PLCs are broadly classified into four kinds: $\beta$, $\gamma$, $\delta$ and $\epsilon$, and are present as a total of eleven isozymes. PLC-$\delta$1 plays a major role in ischemia and apoptosis by regulating the opening of mitochondrial permeability transition pores (mPTP), the targeting of proteases activated by calcium ions, and intracellular calcium homeostasis.

Also included as polypeptides of the present invention are fragments, derivatives, analogs, or variants of the foregoing polypeptides, and any combination thereof, which are used to prevent or treat, i.e., cure, ameliorate, lessen the severity of, or prevent or reduce ischemic or hypoxic conditions and/or neural injury.

Further embodiments of the invention include polypeptides, which comprise amino acid sequences at least 95% identical, and more preferably at least 96%, 97%, 98% or 99% identical, to any of the amino acid sequences of the polypeptides described above.

As a practical matter, whether any particular polypeptide is at least 95%, 96%, 97%, 98% or 99% identical to, for instance, the amino acid sequence shown in SEQ ID NO:11 can be determined conventionally using known computer programs such as the Bestfit program (Wisconsin Sequence Analysis Package, Version 8 for Unix, Genetics Computer Group, University Research Park 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acids in the reference sequence are allowed.

Polynucleotides

Additionally, the present invention relates to polynucleotides which encode fusion proteins or chimeric proteins, recombinant expression vectors, plasmids and other polynucleotide constructs (collectively referred to as "expression vectors") containing the same, microorganisms transformed with these expression vectors, and processes for obtaining these polynucleotides, and transformed cells using said vectors. Suitable host cells can be transformed with the expression vectors.

As used herein, the term "expression vector" refers to a construct made up of genetic material (i.e., nucleic acids). Typically, a expression vector contains an origin of replication which is functional in bacterial host cells, e.g., *Escherichia coli*, and selectable markers for detecting bacterial host cells comprising the expression vector. Expression vectors of the present invention contain a promoter sequence and include genetic elements as described herein arranged such that an inserted coding sequence can be transcribed and translated in eukaryotic cells. In certain embodiments described herein, an expression vector is a closed circular DNA molecule.

The term "expression" refers to the biological production of a product encoded by a coding sequence. In most cases, a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

The fusion proteins or chimeric proteins of this invention can be prepared by recombinant DNA methodology. In accordance with the present invention, a gene sequence coding for a desired protein is isolated, synthesized or otherwise obtained and operably linked to a DNA sequence coding for the PTD peptide. The hybrid gene containing the gene for a desired protein operably linked to a DNA sequence encoding a PTD peptide is referred to as a chimeric gene. Optionally, the gene sequence coding for a desired protein may be operably linked to the DNA sequence coding for the PTD peptide via a linker sequence.

The term "linker peptide" is intended to define any sequence of amino acid residues which preferably provide a hydrophilic region when contained in an expressed protein. Such a hydrophilic region may facilitate cleavage by an enzyme at the proteolytic cleavage site.

The chimeric gene is inserted into an expression vector which allows for the expression of the desired chimeric protein in a suitable transformed host. The expression vector provides the inserted chimeric gene with the necessary regulatory sequences to control expression in the suitable transformed host.

The nucleic acid construct may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

Regulatory elements that control expression of the fusion protein of the present invention include the promoter region, the 5' untranslated region, the signal sequence, the chimeric coding sequence, the 3' untranslated region, and the transcription termination site. Fusion proteins which are to be secreted from a host into the medium also contain the signal sequence.

Similarly, a variety of translation control elements are known to those of ordinary skill in the art. These include, but are not limited to ribosome binding sites, and translation initiation and termination codons.

Methods and materials for preparing recombinant vectors and transforming host cells using the same, replicating the vectors in host cells and expressing biologically active foreign polypeptides and proteins are described in Principles of Gene Manipulation, by Old and Primrose, 2nd edition (1981), and Sambrook et al., Molecular Cloning, 3rd edition, Cold Spring Harbor Laboratory (2001), both incorporated herein by reference.

As used herein, the term "DNA polynucleotide" may be a circular or linearized plasmid, or other linear DNA which may also be non-infectious and nonintegrating (i.e., does not integrate into the genome of vertebrate cells). A linearized plasmid is a plasmid that was previously circular but has been linearized, for example, by digestion with a restriction endonuclease. Linear DNA may be advantageous in certain situations as discussed, e.g., in Cherng, J. Y., et al., *J. Control. Release* 60:343-53 (1999), and Chen, Z. Y., et al., *Mol. Ther.* 3:403-10 (2001), both of which are incorporated herein by reference.

Further embodiments of the invention include vectors comprising chimeric genes, which comprise a nucleotide sequence at least 95% identical, and more preferably at least 96%, 97%, 98% or 99% identical, to any of the nucleotide sequences of the vectors comprising chimeric genes described above.

Other embodiments of the invention include chimeric genes, which comprise a nucleotide sequence at least 95% identical, and more preferably at least 96%, 97%, 98% or 99% identical, to any of the nucleotide sequences of the chimeric genes described above.

As a practical matter, whether any particular vector or chimeric gene is at least 95%, 96%, 97%, 98% or 99% identical to a nucleotide sequence according to the present invention, can be determined conventionally using known computer programs such as the Bestfit program (Wisconsin Sequence Analysis Package, Version 8 for Unix, Genetics Computer Group, University Research Park 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Codon Optimization

"Codon optimization" is defined as modifying a nucleic acid sequence for enhanced expression in the cells of the subject of interest, e.g., human, by replacing at least one, more than one, or a significant number, of codons of the native sequence with codons that are more frequently or most frequently used in the genes of that subject. Various species exhibit particular bias for certain codons of a particular amino acid.

In one aspect, the present invention relates to polynucleotide expression constructs or vectors, and host cells comprising nucleic acid fragments of codon-optimized coding regions which encode therapeutic polypeptides, and fragments, variants, or derivatives thereof, and various methods of using the polynucleotide expression constructs, vectors, host cells to treat or prevent disease in a subject.

As used herein the term "codon-optimized coding region" means a nucleic acid coding region that has been adapted for expression in the cells of a given subject by replacing at least one, or more than one, or a significant number, of codons with one or more codons that are more frequently used in the genes of that subject.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). Many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Consensus Sequences

The present invention is further directed to expression plasmids that contain chimeric genes which express therapeutic fusion proteins with specific consensus sequences, and fragments, derivatives and variants thereof. A "consensus sequence" is, e.g., an idealized sequence that represents the amino acids most often present at each position of two or more sequences which have been compared to each other. A consensus sequence is a theoretical representative amino acid sequence in which each amino acid is the one which occurs most frequently at that site in the different sequences which occur in nature. The term also refers to an actual sequence which approximates the theoretical consensus. A consensus sequence can be derived from sequences which have, e.g., shared functional or structural purposes. It can be defined by aligning as many known examples of a particular structural or functional domain as possible to maximize the homology. A sequence is generally accepted as a consensus when each particular amino acid is reasonably predominant at its position, and most of the sequences which form the basis of the comparison are related to the consensus by rather few substitutions, e.g., from 0 to about 100 substitutions. In general, the wild-type comparison sequences are at least about 50%, 75%, 80%, 90%, 95%, 96%, 97%, 98% or 99% identical to the consensus sequence. Accordingly, polypeptides of the invention are about 50%, 75%, 80%, 85%, 90%, 91%, 92%, 93%, 94%, 95%, 96%, 97%, 98%, 99% or 100% identical to the consensus sequence.

A "consensus amino acid" is an amino acid chosen to occupy a given position in the consensus protein. A system which is organized to select consensus amino acids can be a computer program, or a combination of one or more computer programs with "by hand" analysis and calculation. When a consensus amino acid is obtained for each position of the aligned amino acid sequences, then these consensus amino acids are "lined up" to obtain the amino acid sequence of the consensus protein.

Therapeutic Uses

Contemplated is the use of the therapeutic fusion proteins described above in the manufacture of a medicament for the alleviation and treatment of ischemic diseases or conditions and/or neural injury. Ischemic diseases or conditions leading to hypoxia in the heart and the brain can be effectively alleviated by administration of the PTD-PLC fusion protein.

Generally, the influx of calcium ions during an ischemic event results in the opening of mitochondrial pores thereby further increasing intracellular concentration of calcium and activation a number of cytoplasmic proteins, such as proteases and endonucleases. Calcium-activated proteases degrade proteins which normally regulate the intracellular calcium level, thereby reducing the reactivity of the proteins with calcium. This leads to myocardial hypertrophy, heart failure, apoptosis or necrosis. PLC-δ1 functions to inhibit the inflow of calcium, when an excess of calcium is present in the cytoplasm.

The therapeutic fusion proteins of the invention may be coadministered with one or more compounds or constructs. Other compounds include, but are not limited to, anti-platelet drugs, anti-coagulant drugs, or anti-thrombotic drugs. Other constructs include, but are not limited to, PTD-calpain or PTD-caspase inhibitors to prevent the degradation of PLC.

The therapeutic fusion proteins of the invention may be targeted to the following cells or cell types: cardiovascular cells, such as cardiac myocyte, ventricular myocyte, atrial myocyte, cardiac stem cell, endothelial cell, vascular smooth muscle cell, pacemaker cell, myofibroblast or fibroblast, and neural cells, such as neurons (also called nerve cell or neurocyte).

Methods and Administration

The present invention provides methods for delivery of a therapeutic fusion polypeptide, or a fragment, variant, or derivative thereof, in admixture with one or more pharmaceutically acceptable carriers or excipients. The therapeutic fusion polypeptide is provided as a recombinant protein, in particular, a fusion protein, or a purified subunit, which comprises administering to a subject one or more of the compositions described herein; such that upon administration of compositions such as those described herein, a therapeutic response is generated in a subject. The delivery can occur, for example, through the skin, nose, eye, into muscle, brain or heart, or by intravenous injection.

The term "subject" is intended to encompass living organisms such as humans, monkeys, cows, sheep, horses, pigs, cattle, goats, dogs, cats, mice, rats, cultured cells therefrom, and transgenic species thereof. In a preferred embodiment, the subject is a human.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

The present invention further provides a method for generating, enhancing or modulating a therapeutic response comprising administering to a human one or more of the compositions described herein. In this method, the compositions may include one or more polypeptides, or a fragment, variant, or derivative thereof, wherein the protein is provided as a recombinant protein, in particular, a fusion protein, or a purified subunit.

As used herein, a "therapeutic response" refers to the ability of a subject to elicit a positive reaction to a composition, as disclosed herein, when delivered to that subject.

As mentioned above, compositions of the present invention can be used to therapeutically treat and prevent disease or disease conditions. As defined herein, "treatment" refers to the use of one or more compositions of the present invention to prevent, cure, retard, or reduce the severity of a disease or disease symptoms in a subject, and/or result in no worsening of the disease.

The diseases or disease conditions caused by or leading to ischemia/hypoxia that are contemplated as part of this invention include, but are not limited to, calcium overload, cardiac hypoxia, cardiac hypoxia-reoxygenation, cardiac ischemia-reperfusion injury, ischemic heart disease, heart failure, heart hypertrophy, heart surgery, traumatic heart injury, coronary angioplasty, vascular defects or blockages (obstruction of blood flow), congenital heart disease, congestive heart failure, cardiac cell muscle regeneration, chemotherapeutic induced cardiomyopathy, myocardial infarction, cardiac arrest, cardiotoxicity, cardiac damage due to parasitic infection, fulminant cardiac amyloidosis, cardiac transplantation, or traumatic cardiac injury.

Additional diseases or disease conditions caused by or leading to ischemia/hypoxia that are contemplated as part of this invention include, but are not limited to, traumatic brain injury, neurological disease or injury, neural disease or injury (e.g., spinal cord), frost damage, ischemic or hemorrhagic stroke, intracranial bleedings (subarachnoid hemorrhage, thrombolytica-induced etc.), blood clots, hypoxia-induced apoptosis, and tissue damage following ischemia-reperfusion.

The term "prevention" refers to the use of one or more compositions of the present invention to generate a therapeutic responses in a subject. It is not required that any composition of the present invention totally cure or eliminate all disease symptoms.

In certain embodiments, one or more compositions of the present invention are delivered to a subject by methods described herein, thereby achieving an effective therapeutic response. More specifically, the compositions of the present invention may be administered to any tissue of a subject, including, but not limited to, skin, muscle, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage. The preferred tissues are heart and brain tissue.

Furthermore, the compositions of the present invention may be administered to any internal cavity of a subject, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention is administered to the lumen of a duct of a salivary gland or liver, the desired polypeptide is expressed in the salivary gland and the liver such that the polypeptide is delivered into the blood stream of the subject from each of the salivary gland or the liver. Certain modes for administration to secretory organs of a gastrointestinal system using the salivary gland, liver and pancreas to release a desired polypeptide into the bloodstream is disclosed in U.S. Pat. Nos. 5,837,693 and 6,004,944, both of which are incorporated herein by reference in their entireties.

According to the disclosed methods, compositions of the present invention

According to the disclosed methods, compositions of the present invention can be administered by injection, intravenous (i.v.), intramuscular (i.m.), subcutaneous (s.c.), or intrapulmonary routes. Other suitable routes of administration include, but are not limited to intratracheal instillation, transdermal, intraocular, intranasal, inhalation, intracavity, intraductal (e.g., into the pancreas) and intraparenchymal (i.e., into any tissue) administration. For intravenous administration, appropriate pharmaceutically acceptable carriers can be used, such as phosphate buffered saline, saline, or other materials used for administration of drugs intravenously. Transdermal delivery includes, but is not limited to intradermal (e.g., into the dermis or epidermis), transdermal (e.g., percutaneous) and transmucosal administration (i.e., into or through skin or mucosal tissue). Intracavity administration includes, but is not limited to administration into oral, vaginal, rectal, nasal, peritoneal, or intestinal cavities as well as, intrathecal (i.e., into the spinal canal), intraventricular (i.e., into the brain ventricles or the heart ventricles), intra-atrial (i.e., into the heart atrium) and sub arachnoid (i.e., into the sub arachnoid spaces of the brain) administration.

Any mode of administration can be used so long as the mode results in delivery or the expression of the desired peptide or protein, in the desired tissue, in an amount sufficient to generate a therapeutic response to a disease condition in a human in need of such a response.

Administration means of the present invention include needle injection (for example as a sterile aqueous dispersion, preferably isotonic), transdermal, catheter infusion, biolistic injectors, particle accelerators (e.g., "gene guns" or pneumatic "needleless" injectors) Med-E-Jet (Vahlsing, H., et al., *J. Immunol. Methods* 171:11-22 (1994)), Pigjet (Schrijver, R., et al., *Vaccine* 15:1908-1916 (1997)), Biojector (Davis, H., et al., *Vaccine* 12:1503-1509 (1994); Gramzinski, R., et al., *Mol. Med.* 4:109-118 (1998)), AdvantaJet (Linmayer, I., et al., *Diabetes Care* 9:294-297 (1986)), Medi-jector (Martins, J., and Roedl, E. J., *Occup. Med.* 21:821-824 (1979)), gelfoam sponge depots, other commercially available depot materials (e.g., hydrogels), osmotic pumps (e.g., Alza minipumps), oral or suppositorial solid pharmaceutical formulations, such as tablets, pills, soft and hard capsules, liquids, suspensions, syrups, granules and elixers, topical skin creams or gels, and decanting, use of polynucleotide coated suture (Qin, Y., et al., *Life Sciences* 65:2193-2203 (1999)) or topical applications during surgery.

Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir, L. M., et al., *Proc. Natl. Acad. Sci. USA* 96:4262-7 (1999); Hartikka, J., et al., *Mol. Ther.* 4:407-15 (2001); Mathiesen, I., *Gene Ther.* 6:508-14 (1999); Rizzuto G., et al., *Hum. Gen. Ther.* 11:1891-900 (2000). Each of the references cited in this paragraph is incorporated herein by reference in its entirety.

Determining an effective amount of one or more compositions of the present invention depends upon a number of factors including, for example, the fusion polypeptide, variants, or derivatives thereof being expressed or administered directly, the age, weight and sex of the subject, the precise condition requiring treatment and its severity, the route of administration, the in vivo half-life of the fusion polypeptide, the efficiency of uptake, and the area to be treated. Treatment can be repeated as necessary, based on clinical judgment, in view of patient response.

A "pharmaceutically effective amount" or a "therapeutically effective amount" is an amount sufficient to generate a therapeutic or clinical response to a disease condition. The terms "pharmaceutically effective amount" or a "therapeutically effective amount are interchangeable. Based on the above factors, determining the precise amount, number of doses, and timing of doses are within the ordinary skill in the art and will be readily determined by the attending physician or veterinarian.

For administration to mammals, and particularly humans, it is expected that the daily dosage of the active agent will be from 0.01 mg/kg body weight, typically around 1 mg/kg. The above dosages are exemplary of the average case. There can, of course, be instances where higher or lower dosages are merited, including picomolar and nanomolar concentrations, and such are within the scope of this invention.

The present invention also relates to compositions comprising the fusion polypeptide(s), as disclosed herein, and an additional pharmaceutically active agent. The fusion polypeptide(s) and associated pharmaceutically active agent may be employed in combination with pharmaceutically acceptable one or more carriers or excipients. Such carriers may include, but are not limited to, diluents (e.g., lactose, dextrose, sucrose, mannitol, sorbitol, cellulose and/or glycine), lubricants (e.g., silica, talc, stearic acid and polyethylene glycol), binders (e.g., magnesium aluminum silicate, starch paste, gelatin, tragacanth, methylcellulose, sodium carboxymethylcellulose and/or polyvinylpyrrolidone), and disintegrants, such as starches, agar, alginic acid, or its sodium salt, and/or absorbents, colorants, flavors, and sweeteners, saline, buffered saline, liposomes, water, glycerol, ethanol and combinations thereof.

Compositions of the present invention may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a human.

Compositions of the present invention can be formulated according to known methods. Suitable preparation methods are described, for example, in *Remington's Pharmaceutical Sciences*, 16th Edition, A. Osol, ed., Mack Publishing Co., Easton, Pa. (1980), and *Remington's Pharmaceutical Sciences*, 19th Edition, A. R. Gennaro, ed., Mack Publishing Co., Easton, Pa. (1995), both of which are incorporated herein by reference in their entireties. Although the composition may be administered as an aqueous solution, it can also be formulated as an emulsion, gel, solution, suspension, lyophilized form, or any other form known in the art.

The following examples are included for purposes of illustration only and are not intended to limit the scope of the present invention, which is defined by the appended claims. All references cited in the Examples are incorporated herein by reference in their entireties.

EXAMPLES

Example 1

Preparation of Expression Vector Containing PTD-PLC-δ1

In order to link a base sequence encoding HSP-70 with a base sequence encoding a peptide region from 848$^{th}$ amino acid tyrosine to 868$^{th}$ amino acid from the N-terminus of human transcription factor Hph-1 (GenBank Accession No: U63386), the primers having the following base sequences were synthesized: a base sequence corresponding to restriction enzyme BamHI for cloning into a pET28B(+) vector having a base sequence from 858$^{th}$ amino acid tyrosine to 868$^{th}$ amino acid arginine from the N-terminus of Hph-1; and a base sequence corresponding to restriction enzyme HindIII for cloning with sequences corresponding to the 5'-terminus of said base sequence and the 3'-terminus of PTD-PLC-δ1. PCR was performed using the above primers, a pRS vector (commercially available from Invitrogen) containing the whole gene of the PTD-PLC-δ1 protein, as a template, and pfu turbo DNA polymerase (Stratagene, cat. #600252-51).

The PCR reaction product was cut with restriction enzymes EcoRI and HindIII, and purified with the Quiaquick PCR purification kit (QIAGEN, cat. #28104). The purified product was cloned into the BamHI and HindIII sites of pET28B (+) purified using a gel extraction method, to prepare a recombinant expression vector. The prepared recombinant vector was named "pPTD-PLC-δ1."

Example 2

Preparation of *E. coli* Transformants and Expression and Purification of Fusion Protein

*E. coli* BL21-DE3 (ATCC No. 53863) was transformed with the expression vector pPTD-PLC-δ1 prepared in Example 1, by heat shock transformation, and the transformed *E. coli* strain was inoculated into 4 ml of LB medium and pre-cultured at 37° C. for 14 hours through stirring. Then, the pre-culture medium was inoculated into 250 ml of LB medium (10 g casein pancreatic digest, 5 g yeast extract, 10 g sodium chloride), and cultured at 37° C. for 3 hours. Then, 1 mM IPTG (isopropyl β-D-thiogalactopyranoside; Gibco-BRL cat. #15529-019) was added to the culture medium, and the mixture was cultured at 22° C. for 8 hours to induce the expression of a fusion protein. The culture medium was centrifuged at 4° C. and 6,000 rpm for 20 minutes, and the supernatant was removed, leaving pellets. The pellets were dissolved in 10 ml of buffer solution 1 (50 mM NaH$_2$PO$_4$, 300 mM NaCl, 10 mM imidazole, pH 8.0) and sonicated with an ultrasonic processor (Heat systems, ultrasonic processor XL) on ice at an intensity of 300 W for 6 seconds and then cooled. The sonication and cooling steps were repeated such that the total sonication time reached 8 minutes. The lysate was centrifuged at 4° C. and 12,000 rpm for 10 minutes, and the disrupted *E. coli* cells were removed and only a pure lysate was collected. To the collected lysate, 0.5 ml of 50% Ni$^{2+}$-NTA agarose slurry (Qiagen, cat #30230) was added, and the suspension was stirred at 4° C. at 200 rpm for 1 hour, such that the fusion protein and the Ni$^{2+}$-NTA agarose were bound to each other. The mixture was passed through a 0.8×4 cm chromatography column (BioRad, cat. #731-1550). The resulting material was washed two times with 4 ml of buffer solution 2 (20 mM Tris-HCl, 500 mM NaCl, 20 mM imidazole, pH 7.9), and treated with 1 ml of buffer solution 3 (50 mM NaH$_2$PO$_4$, 300 mM NaCl, 250 mM imidazole, pH 8.0) and 1 ml of buffer solution 4 (50 mM NaH$_2$PO$_4$, 300 mM NaCl, 500 mM imidazole, pH 8.0), thus obtaining a fusion protein fraction. The fraction was desalted with a PD-10 desalting column (Amersham-Pharmacia Biotech cat. #17-0851-01). The isolated and purified PTD-PLC-δ1 fusion protein was subjected to SDS-PAGE, and then analyzed by Coomassie blue staining, and the results are shown in FIG. 1.

Example 3

PTD-PLC-δ1 Prevents Ischemia in Myocardial Cells

The heart of each of 1-3-day-old white rats was separated and placed in PBS, and only the left ventricle was separated and then cut with micro dissecting scissors to a size of about 1 mm$^3$, to which 5 ml of collagenase II (0.8 mg/ml, 262 units/mg, Gibco BRL) was added. The suspension was left to stand in a 5% CO$_2$ incubator at 37° C. for 5 minutes, and the floated collagenase II was removed. Five ml of fresh collagenase II was added thereto and suspended, and the suspension was left to stand for an additional time of 5 minutes, and the supernatant was then transferred into a fresh tube. Five ml of a cell culture medium (10% FBS-containing α-MEM, Gibco BRL) was added thereto, the cell solution was centrifuged at 1200 rpm for 4 minutes, and the cells were collected. The above procedure was repeated 7-9 times until almost no tissue was remaining, and the cell suspensions separated as single cells were collected in one tube. The cells were cultured on a 100-mm tissue culture plate for 1-3 hours to allow only fibroblasts to adhere to the plate, and cells non-adhered to plate were collected, seeded at a concentration of 5×10$^5$ cells/ml and cultured. After 4-6 hours, it was replaced with fresh medium, 0.1 mM BrdU was then added thereto to inhibit the growth of fibroblasts and, at the same time, various concentrations (0 μM for a control group, and 0.1 μM, 0.5 μM and 1.0 μM concentrations for test groups) of the PTD-PLC-δ1 protein were added to the cultured myocardial cells. The cells were then cultured in low-oxygen conditions for 12 hours. The culturing in low-oxygen conditions was carried out in an airtight humidified chamber (Anaerobic Environment, ThermoForma, Marietta, Ohio, USA), which was maintained at 37° C. and continuously supplied with a mixed gas of 10% CO$_2$, 5% H$_2$ and 85% N$_2$. As medium in the culture step, a medium containing only 1% bovine fetal serum was used. The cultured cells were analyzed by Western blot using an anti-PTD-PLC-δ1 antibody.

The results show that the delivery effect of the PTD-PLC-δ1 protein increased in a concentration-dependent manner. It can be seen that the PTD-PLC-δ1 protein in the myocardial cells cultured under low-oxygen conditions for 12 hours remained with a concentration gradient of 0-500 nM, and the cell viability increased according to the concentration gradient of the remaining PTD-PLC-δ1 protein (see FIG. 2A). Also, the cell viability increased according to the concentration gradient of the remaining PTD-PLC-δ1 protein (see FIG. 2B).

Example 4

PTD-PLC-δ1 Inhibits Calcium Overload in Ischemic Myocardial Cells

The measurement of the concentration of free Ca$^{2+}$ in the cytoplasm was performed by confocal microscope analysis. To myocardial cells under low-oxygen conditions, the purified PTD-PLC-δ1 was added at a concentration of 1 μM, and the cells were then cultured for 12 hours and measured for the concentration of calcium. For this purpose, on a glass thin section coated with laminin (5 g/cm$^2$), the myocardial cells of newly born white rats were cultured in 0.1 mM BrdU-containing cell culture medium (10% FBS-containing-MEM, Gibco BRL) for one day. After completion of the culture, the cells were washed with a modified Tyrode's solution consisting of 0.265 g/l CaCl$_2$, 0.214 g/l MgCl$_2$, 0.2 g/l KCl, 8.0 g/l NaCl, 1 g/l glucose, 0.05 g/l NaH$_2$PO$_4$, and 1.0 g/l NaHCO$_3$. The modified Tyrode's solution was loaded with 2 μM fluo-4 acetoxymethyl ester (Fluo-4 AM, Molecular Probes, Eugene, Oreg.) in a dark room at room temperature for 20 minutes. The fluorescent images were acquired with an argon laser confocal microscope (Leica, Solms, Germany). The fluorochromes were excited using the argon laser turned at 488 nm, and the emission of fluorescence was collected through a 510-560 nm band pass filter. Also, the relative change in intracellular free Ca$^{2+}$ was determined by the measurement of fluorescent intensity.

The results show that an overload of calcium in the myocardial cells cultured under low-oxygen conditions for 12 hours was about 3 times higher than in a control group incubated under oxygen conditions. However, when the myocardial cells under low-oxygen conditions were treated with 100 nM of the PTD-PLC-δ1 protein, the intracellular calcium overload was restored to a level approximately equal to that of the control group (see FIG. 3).

Example 5

Effect of PTD-PLC-δ1 on Treatment of Cardiac Ischemic Area in Myocardial Infarct Animal Model Myocardial infarct in white rats was induced by reperfusion after left anterior descending coronary artery ligation. Under general anesthesia, 8-week-old Sprague-Dawley male rats (weighing about 205 g each) were intubated with an endotracheal tube and then ventilated with positive pressure (180 ml/min), and the ventilation was maintained with oxygen-containing (2 L/min) indoor air using a Harvard ventilator. The rat heart was exposed by left thoracotomy, and the left anterior descending coronary artery was ligated with 5-0 silk suture, followed by standing for 1 hour. After the left anterior descending coronary artery was ligated for 1 hour, 100 nM PTD-PLC-δ1 was intravenously injected into the rat and, at the same time, the ligation was released.

In one group (n=3), to determine the amount of PLC-δ1 in the cardiac ischemic area, the reperfusion was performed for 3 hours, and the residual amount of PLC-δ1 protein in the tissue was analyzed. In another group (n=3), to determine the effect of PTD-PLC-δ1 on the survival of myocardial cells in the ischemic area, the reperfusion was continued for 2 weeks following the release of the ligation. Upon release of the ligation, the animals were bred in a breeding room in its normal environment for 2 weeks, after which the heart was isolated.

The isolated heart was perfused with 10% (v/v) neutrally buffered formaldehyde, fixed in the formaldehyde, transversely cut into four sections having the same thickness, and then embedded in paraffin according to a general method. The 2-μm thick sections were placed on a gelatin-coated glass slide to enable dyes to work on the continuous section of the transplanted tissue area. After paraffin removal and rehydration, the sections were stained with haematoxylin and eosin in order to observe cytological details, such as nuclei, cytoplasm, and connective tissues.

The analysis of the amount of PLC-δ1 revealed that in the kidney and liver, the test group injected with PTD-PLC-δ1 was no different than the control group. However, in the heart, the injected PTD-PLC-δ1 protein was present in a significant amount, and the phosphorylation of protein kinase C was greatly increased (see FIG. 4).

The analysis of the effect of PTD-PLC-δ1 on the survival of myocardial cells revealed that the survival rate of the myocardial cells in the group injected intravenously with PTD-PLC-δ1 was significantly higher than that of the control group (see FIG. 5).

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

What is claimed is:

1. A method of preventing ischemia-reperfusion injury in a subject suffering from hypothermia, comprising pre-treating the subject with a therapeutically effective amount of a fusion polypeptide comprising a protein transduction domain and a human phospholipase C delta-1 polypeptide;

wherein the protein transduction domain comprises an amino acid sequence that is any one of SEQ ID NOs:1-9; and wherein the protein transduction domain delivers a polypeptide into a cell.

2. The method of claim 1, wherein the human phospholipase C delta-1 polypeptide increases cell viability in low-oxygen conditions.

3. A method of treating ischemia-reperfusion injury in a subject suffering from hypothermia, comprising pre-treating the subject with a therapeutically effective amount of a fusion polypeptide comprising a protein transduction domain and a human phospholipase C delta-1 polypeptide;

wherein the protein transduction domain comprises an amino acid sequence that is any one of SEQ ID NOs: 1-9; and wherein the protein transduction domain delivers a polypeptide into a cell.

4. The method of claim 3, wherein the human phospholipase C delta-1 polypeptide increases cell viability in low-oxygen conditions.

5. The method of claim 4, wherein the human phospholipase C delta-1 polypeptide comprises an amino acid sequence that is at least 95% identical to SEQ ID NO:11.

6. The method of claim 5, wherein the human phospholipase C delta-1 polypeptide comprises an amino acid sequence that is at least 96% identical to SEQ ID NO:11.

7. The method of claim 6, wherein the human phospholipase C delta-1 polypeptide comprises an amino acid sequence that is at least 97% identical to SEQ ID NO:11.

8. The method of claim 7, wherein the human phospholipase C delta-1 polypeptide comprises an amino acid sequence that is at least 98% identical to SEQ ID NO:11.

9. A method of treating ischemia-reperfusion injury in a subject suffering from hypothermia, comprising pre-treating the subject with a therapeutically effective amount of a fusion polypeptide comprising a protein transduction domain and a human phospholipase C delta-1 polypeptide;
wherein the protein transduction domain comprises an amino acid sequence that is any one of SEQ ID NOs: 1-9;
wherein the protein transduction domain delivers a polypeptide into a cell; and
wherein the human phospholipase C delta-1 polypeptide comprises an amino acid sequence that is at least 99% identical to SEQ ID NO:11.

10. The method of claim 9, wherein the human phospholipase C delta-1 polypeptide increases cell viability in low-oxygen conditions.

11. The method of claim 9, wherein the human phospholipase C delta-1 polypeptide comprises the amino acid sequence of SEQ ID NO:11.

12. The method of claim 3, wherein the human phospholipase C delta-1 polypeptide consists of the amino acid sequence of SEQ ID NO:11.

13. The method of claim 3, wherein the human phospholipase C delta-1 polypeptide comprises a calcium binding domain that consists of the amino acid sequence of SEQ ID NO:25.

14. The method of claim 5, wherein the human phospholipase C delta-1 polypeptide comprises a calcium binding domain that consists of the amino acid sequence of SEQ ID NO:25.

15. The method of claim 6, wherein the human phospholipase C delta-1 polypeptide comprises a calcium binding domain that consists of the amino acid sequence of SEQ ID NO:25.

16. The method of claim 7, wherein the human phospholipase C delta-1 polypeptide comprises a calcium binding domain that consists of the amino acid sequence of SEQ ID NO:25.

17. The method of claim 8, wherein the human phospholipase C delta-1 polypeptide comprises a calcium binding domain that consists of the amino acid sequence of SEQ ID NO:25.

18. The method of claim 3, wherein the protein transduction domain and the human phospholipase C delta-1 polypeptide are linked to each other by a linker, wherein the linker comprises the amino acid sequence of SEQ ID NO:37.

19. The method of claim 3, wherein the protein transduction domain and the human phospholipase C delta-1 polypeptide are linked to each other by a linker, wherein the linker comprises Gly-Gly-Gly.

20. A method of treating ischemia-reperfusion injury in a subject suffering from hypothermia, comprising pre-treating the subject with a therapeutically effective amount of a fusion polypeptide comprising a protein transduction domain and a human phospholipase C delta-1 polypeptide;
wherein the protein transduction domain comprises an amino acid sequence that is identical to any one of SEQ ID NOs:1-9 except for no more than 2 amino acid substitutions,
wherein the protein transduction domain delivers a polypeptide into a cell.

21. The method of claim 20, wherein the human phospholipase C delta-1 polypeptide increases cell viability in low-oxygen conditions.

22. The method of claim 20, wherein the protein transduction domain comprises a sequence that is identical to the sequence of any one of SEQ ID NOs: 1-9 except for no more than 1 amino acid substitution.

23. The method of claim 20, wherein the protein transduction domain comprises an amino acid sequence that is identical to SEQ ID NO:1 except for no more than 2 amino acid substitutions.

24. The method of claim 23, wherein the protein transduction domain comprises an amino acid sequence that is identical to SEQ ID NO:1 except for no more than 1 amino acid substitution.

25. A method of reducing ischemia-reperfusion injury in a subject suffering from hypothermia, comprising pre-treating the subject with a therapeutically effective amount of a fusion polypeptide comprising a protein transduction domain and a human phospholipase C delta-1 polypeptide;
wherein the protein transduction domain comprises an amino acid sequence that is any one of SEQ ID NOs:1-9;
wherein the protein transduction domain delivers a polypeptide into a cell.

26. The method of claim 25, wherein the human phospholipase C delta-1 polypeptide increases cell viability in low-oxygen conditions.

* * * * *